US009848603B2

(12) United States Patent
Anderson et al.

(10) Patent No.: US 9,848,603 B2
(45) Date of Patent: Dec. 26, 2017

(54) METHODS FOR PROTECTING PLANTS WITH ANTIFUNGAL COMPOSITIONS

(71) Applicant: Hexima Limited, Melbourne (AU)

(72) Inventors: Marilyn Anderson, Keilor (AU); Robyn Heath, Northcote (AU); James McKenna, Pascoe Vale South (AU); Nicole Van Der Weerden, Coburg (AU)

(73) Assignee: Hexima Limited, Melbourne (AU)

( * ) Notice: Subject to any disclaimer, the term of this patent is extended or adjusted under 35 U.S.C. 154(b) by 0 days.

(21) Appl. No.: 14/710,482

(22) Filed: May 12, 2015

(65) Prior Publication Data

US 2015/0237860 A1 Aug. 27, 2015

Related U.S. Application Data

(63) Continuation of application No. 12/362,657, filed on Jan. 30, 2009, now abandoned.

(60) Provisional application No. 61/085,682, filed on Aug. 1, 2008, provisional application No. 61/025,655, filed on Feb. 1, 2008.

(51) Int. Cl.
| | |
|---|---|
| *C12N 15/82* | (2006.01) |
| *A01N 43/88* | (2006.01) |
| *A01N 43/36* | (2006.01) |
| *A01N 43/54* | (2006.01) |
| *A01N 65/00* | (2009.01) |
| *A01N 65/38* | (2009.01) |
| *A01N 37/46* | (2006.01) |
| *A01N 43/40* | (2006.01) |
| *A01N 43/647* | (2006.01) |
| *A01N 43/653* | (2006.01) |

(52) U.S. Cl.
CPC ............ *A01N 43/88* (2013.01); *A01N 37/46* (2013.01); *A01N 43/36* (2013.01); *A01N 43/40* (2013.01); *A01N 43/54* (2013.01); *A01N 43/647* (2013.01); *A01N 43/653* (2013.01); *A01N 65/00* (2013.01); *A01N 65/38* (2013.01); *C12N 15/8282* (2013.01)

(58) Field of Classification Search
None
See application file for complete search history.

(56) References Cited

U.S. PATENT DOCUMENTS

| | | | |
|---|---|---|---|
| 4,767,777 A | 8/1988 | Bass et al. | |
| 5,482,928 A | 1/1996 | De Bolle et al. | |
| 5,538,525 A | 7/1996 | Broekaert et al. | |
| 5,689,043 A | 11/1997 | Broekaert et al. | |
| 5,895,751 A * | 4/1999 | Hattori | C12Q 1/18 435/21 |
| 6,031,153 A | 2/2000 | Ryals et al. | |
| 6,121,436 A | 9/2000 | Liang et al. | |
| 6,147,281 A | 11/2000 | Garcia-Olmedo et al. | |
| 6,215,048 B1 | 4/2001 | Liang et al. | |
| 6,316,407 B1 | 11/2001 | Liang et al. | |
| 6,329,504 B1 | 12/2001 | Liang et al. | |
| 6,512,166 B1 | 1/2003 | Harman et al. | |
| 6,605,698 B1 | 8/2003 | van Amerongen et al. | |
| 6,653,280 B2 | 11/2003 | Liang et al. | |
| 6,677,503 B1 | 1/2004 | Bidney et al. | |
| 6,770,750 B2 | 8/2004 | Oh et al. | |
| 6,806,074 B2 | 10/2004 | Anderson et al. | |
| 6,855,865 B2 | 2/2005 | Famodu et al. | |
| 6,864,068 B2 | 3/2005 | Rees et al. | |
| 6,911,577 B2 | 6/2005 | Simmons et al. | |
| 6,916,970 B2 | 7/2005 | Liang et al. | |
| 6,946,278 B2 | 9/2005 | Anderson et al. | |
| 6,955,916 B2 | 10/2005 | Anderson et al. | |
| 7,041,877 B2 | 5/2006 | Anderson et al. | |
| 7,238,781 B2 | 7/2007 | Famodu et al. | |
| 7,297,840 B2 | 11/2007 | Anderson et al. | |
| 7,309,596 B2 | 12/2007 | Anderson et al. | |

(Continued)

FOREIGN PATENT DOCUMENTS

| | | |
|---|---|---|
| WO | 93/04586 | 3/1993 |
| WO | 97/37024 | 10/1997 |
| WO | 98/00023 | 1/1998 |
| WO | 00/11175 | 3/2000 |
| WO | 00/11196 | 3/2000 |

(Continued)

OTHER PUBLICATIONS

Abad et al. (Jul. 21, 1996) "Antifungal Activity of Tobacco Osmotin has Specificity and Involves Plasma Membrane Permeabilization," *Plant Sci.* 118(1):11-23.

Alcouloumre, et al. (Dec. 1993) "Fungal Properties of Defensin NP-1 and Activity Against *Crytococcus neoformans* In Vitro," *Antimicrob. Agents Chemother.* 37(12):2628-2632.

Alexander et al. (Aug. 1993) "Increased Tolerance to Two Oomycete Pathogens in Transgenic Tobacco Expressing Pathogenesis-Related Protein 1a,"*Proc. Nat. Acad. Sci. USA* 90:7327-7331.

(Continued)

*Primary Examiner* — Medina A Ibrahim
(74) *Attorney, Agent, or Firm* — Knobbe, Martens, Olson & Bear, LLP

(57) ABSTRACT

A system for reducing the incidence or severity of fungal infection of a plant, comprising a chemical fungicide component, which may be provided by foliar or root (soil or liquid nutrient) application, together with an antifungal plant defensin not in nature expressed in the plant being protected or expressed in lower amounts or in different tissues, provides synergistic improvement in protection against infection by a plant pathogenic fungus which is susceptible to the defensin and the fungicide. The fungicide can be a strobilurin or a triazole, and the defensin can be selected from a wide range of known defensins, for example, NaD1 and others, or it can be a chimeric defensin engineered for low toxicity to the plant. The defensin can be provided as a protein formulation, optionally together with the fungicide, or it can be provided by recombinant expression in the plant to be protected from fungal infection.

19 Claims, 34 Drawing Sheets

(56) References Cited

U.S. PATENT DOCUMENTS

| | | | |
|---|---|---|---|
| 7,410,796 | B2 | 8/2008 | Anderson et al. |
| 7,462,695 | B2 | 12/2008 | Dunse et al. |
| 7,544,861 | B2 | 6/2009 | Anderson et al. |
| 7,592,433 | B1 | 9/2009 | Craik et al. |
| 8,252,898 | B2 | 8/2012 | Anderson et al. |
| 8,722,968 | B2 | 5/2014 | Anderson et al. |
| 2002/0144306 | A1 | 10/2002 | Liang et al. |
| 2003/0217382 | A1 | 11/2003 | Anderson et al. |
| 2004/0064850 | A1 | 4/2004 | Liang et al. |
| 2004/0073971 | A1 | 4/2004 | Bidney et al. |
| 2004/0111761 | A1 | 6/2004 | Bidney et al. |
| 2005/0058689 | A1 | 3/2005 | McDaniel |
| 2005/0273881 | A1 | 12/2005 | Simmons et al. |
| 2006/0150276 | A1 | 7/2006 | Anderson et al. |
| 2007/0197474 | A1 | 8/2007 | Clinton et al. |
| 2007/0277263 | A1 | 11/2007 | Anderson et al. |
| 2008/0134367 | A1 | 6/2008 | Anderson et al. |
| 2009/0069545 | A1 | 3/2009 | Anderson et al. |
| 2009/0083880 | A1 | 3/2009 | Anderson et al. |
| 2009/0188010 | A1 | 7/2009 | Dunse et al. |
| 2009/0197809 | A1 | 8/2009 | Anderson et al. |
| 2010/0068762 | A1 | 3/2010 | Craik et al. |
| 2010/0095408 | A1 | 4/2010 | Heath et al. |
| 2010/0218280 | A1 | 8/2010 | Anderson et al. |
| 2013/0263326 | A1 | 10/2013 | Heath et al. |
| 2013/0267459 | A1 | 10/2013 | Heath et al. |
| 2013/0269059 | A1 | 10/2013 | Heath et al. |
| 2014/0130209 | A1 | 5/2014 | Van der Weerden et al. |
| 2014/0208461 | A1 | 7/2014 | Anderson et al. |
| 2014/0259231 | A1 | 9/2014 | Anderson et al. |
| 2015/0067917 | A1 | 3/2015 | Heath et al. |
| 2015/0283204 | A1 | 10/2015 | Van der Weerden et al. |

FOREIGN PATENT DOCUMENTS

| | | |
|---|---|---|
| WO | 00/68405 | 11/2000 |
| WO | 00/78983 | 12/2000 |
| WO | 01/09174 | 2/2001 |
| WO | 01/09175 | 2/2001 |
| WO | 04/001012 | 12/2003 |
| WO | 2004/054366 | 7/2004 |
| WO | 2004/072239 | 8/2004 |
| WO | 2007/110686 | 10/2007 |
| WO | 2009/094719 | 8/2009 |

OTHER PUBLICATIONS

Aluru, et al., "Capsicum chinese putative gamma-thionin precursor, mRNA, complete cds", GenBank Nucleotide Accession No. AF128239.1, Jul. 6, 1999.

Bartlett et al. (2002) "The Strobilurin Fungicides," *Pest Manag. Sci.* 58:649-662.

Beck et al. (1993) "Environmental Release Permits," *Bio/Technology* 11:1524-1528.

Broekaert et al. (1990) "An Automated Quantitative Assay for Fungal Growth Inhibition," *FEMS Microbiol. Lett.* 69:55-59.

De Samblanx et al. (Jan. 10, 1997) "Mutational Analysis of a Plant Defensin from Radish (*Raphanus sativus* L.) Reveals Two Adjacent Sites Important for Antifungal Activity," *J. Biol. Chem.* 272(2):1171-1179.

De Vos et al. (Mar. 1985) "Three-Dimensional Structure of Thaumatin I, an Intensely Sweet Protein," *Proc. Nat. Acad. Sci. USA* 82:1406-1409.

Del Sorbo et al. (2000) "Fungal Transporters Involved in Efflux of Natural Toxic Compounds and Fungicides," *Fungal Genet. Biol.* 30:1-15.

Dow AgroSciences, Laredo and PropiMax Fungicide information Sheet, 2007.

Ekengren et al. (Nov. 1999) "*Drosophila* cacropin as an Antifungal Agent," *Insect Biochem. Mol. Biol.* 29(11):965-972.

Epand et al. (2006) Role of Membrane Lipids in the Mechanism of Bacterial Species Selective Toxicity by Two α/β-Antimicrobial Peptides *Biochim. Biophys. Acta* 1758:1343-1350.

Görlach et al. (Apr. 1996) "Benzothiadiazole, a Novel Class of Inducers of Systemic Acquired Resistance, Activates Gene Expression and Disease in Wheat," *Plant Cell* 8:629-643.

Graham et al. (Jul. 2004) "Computational Identification and Characterization of Novel Genes from Legumes," *Plant Physiol.* 135:1179-1197.

Greco et al. (1995) "The Search for Synergy: a Critical Review from a Response Surface Perspective," *Pharmacol. Rev.* 47:331-385.

Gu, et al., "A Flower-Specific cDNA Encoding a Novel Thionin in Tobacco," *Mol. Gen. Genet.* 1992, 234:89-96, Springer-Verlag.

Halcygen Pharmaceuticals Press Release, Jul. 5, 2007, "Halcygen Anti-Fungal Drug Passes Clinical Test—to Enter Phase III Trial in 2007/2008."

Janssen et al. (2003) "Structure of *Petunia hybrida* Defensin 1, a Novel Plant Defensin with Five Disulfide Bonds," Biochemistry 42(27):8214-8222.

Johnson et al. (2005) "Maturation of the Floral Defensin of *Nicotiana alata*," ASPB/ComBio 2005, Adelaide, Sep. 25-29, 2005 (Joint meeting).

Johnson et al. (2006) "The C-Terminal Propeptide Governs Vacuolar Deposition of the *Nicotiana alata* Floral Defensin" Lorne 2006, Feb. 5-9, 2006.

Kim et al. (Aug. 2001) "Internalization of Tenecin 3 by a Fungal Cellular Process is Essential for its Fungicidal Effect on *Candida albicans*," *Eur. J. Biochem.* 268(16):4449-4458.

Klis et al. (2002) "Dynamics of Cell Wall Structure in *Saccharomyces cerevisiae*," *FEMS Microbiol. Rev.* 26:239-256.

Ladokhin et al. (2001) "Detergent-Like Permeabilization of Anionic Lipid Vesicles by Melittin," *Biochim. Biophys. Acta* 1514:253-260.

Ladokhin et al. (Apr. 1997) "Sizing Membrane Pores in Lipid Vesicles by Leakage of Co-Encapsulated Markers: Pore Formation by Melittin," *Biophys. J.* 72:1762-1766.

Lay et al. (2005) "Defensins—Components of the Innate Immune System in Plants," *Curr. Prot. Pept. Sci.* 6:85-101.

Lay et al. (2003) "The Three-Dimensional Solution Structure of NaD1, a New Floral Defensin from *Nicotiana alata* and its Application to a Homology Model of the Crop Defense Protein alfAFP," J Mol Biol 325:175-188.

Lay et al. (Mar. 2003) "Isolation and Properties of Floral Defensins from Ornamental Tobacco and Petunia," *Plant Physiol.* 131:1283-1293.

Leiter et al. (Jun. 2005) "Antifungal Protein PAF Severely Affects the Integrity of the Plasma Membrane of *Aspergillus nidulans* and Induces an Apoptosis-Like Phenotype," *Antimicrob. Agents Chemother.* 49(6):2445-2453.

Lobo et al. (Jan. 6, 2007) "Antifungal *Pisum sativum* Defensin 1 Interacts with *Neurospora crassa* Cyclin F Related to the Cell Cycle," *Biochemistry* 46(4):987-996.

Lou, et al., "Nitrogen Supply Influences Herbivore-Induced Direct and Indirect Defenses and Transcriptional Responses in *Nicotiana attenuata*," *Plant Physiol.* 135:496-506, May 2004, American Society of Plant Biologists.

Marton et al. (2010) "Nontransgenic Genome Modification in Plant Cells," Plant Physiology 154:1079-1087.

Matsuzaki (1999) "Why and How are Peptide-Lipid Interactions Utilized for Self-Defense? Magainins and Tachyplesins as Archetypes," *Biochem. Biophys. Acta* 1462:1-10.

Matsuzaki et al. (1995) "Molecular Basis of Membrane Selectivity of an Antimicrobial Peptide, Magainin 2," *Biochemistry* 34(10):3423-3429.

McKenna et al. (2004) "The Potential of the Antifungal Protein NaD1 for Control of Fusarium Wilt and Verticillium Wilt," 12th Australian Cotton Conference, Aug. 10-12, 2004, 1 page.

Meyer et al. (1996) "Fruit-Specific Expression of a Defensin-Type Gene Family in Bell Pepper" *Plant Physiol.* 112:615-622.

Nilsson et al. (Aug. 25, 1989) "Short Cytoplasmic Sequences Serve as Retention Signals for Transmembrane Proteins in the Endoplasmic Reticulum," *Cell* 58:707-718.

Oberparleiter et al. (Nov. 2003) "Active Internalization of the *Penicillium chrysogenum* Antifungal Protein PAF in Sensitive Aspergilli," *Antimicrob. Agents Chemother.* 47(11):3598-3601.

(56) References Cited

OTHER PUBLICATIONS

Park et al. (2002) "Characterization of a Stamen-Specific cDNA Encoding a Novel Plant Defensin in Chinese Cabbage," *Plant Molecular Biology* 50:59-69.
Pelegrini et al. (2005) "Plant γ-Thionins: Novel Insights on the Mechanism of Action of a Multi-Functional Class of Defense Proteins," *Int. J. Biochem. Cell Biol.* 37:2239-2253.
Potter et al. (1993) "Regulation of a Hevein-Like Gene in *Arabidopsis*," *Mol. Plant Microbe. Interact.* 6:680-685.
Ramamoorthy et al. (Nov. 2007) "Glucosylceramide Synthase is Essential for Alfalfa Defensin-Mediated Growth Inhibition but not for Pathogenicity of *Fusarium graminearum*," *Mol. Microbiol.* 66(3):771-786.
Reimann et al. (Jn.2005) "Inhibition of Efflux Transporter-Mediated Fungicide Resistance in *Pyrenophora tritici-repentis* by a Derivative of 4'-Hydroxyflavone and Enhancement of Fungacide Activity," *Appl. Environ. Microbiol.* 71(6):3269-3275.
Richer (1987) "Synergism—A Patent View," *Pest. Sci.* 19:309-315.
Rogers et al. (1998) "Gene Transfer in Plants: Production of Transformed Plants Using Ti Plasmid Vectors," *Methods for Plant Mol. Biol.* :423-436.
Ryals et al. (1996) "Systemic Acquired Resistance," *The Plant Cell* 8:1809-1819.
Salzman et al. (2004) "Inorganic Cations Mediate Plant PR5 Protein Antifungal Activity Through Fungal *Mnn1*- and *Mnn4*-Regulated Cell Surface Glycans," *Mol. 69Plant Microbe Interact.* 17(0):780-788.
Silverstein et al. (Jun. 2005) "Genome Organization of More Than 300 Defensin-Like Genes in Arabidopsis," *Plant Physiol.* 138:600-610.
Stotz et al. (2009) "Plant Defensins: Defense, Development and Application," *Plant Signaling & Behavior* 4(11):1010-1012.
Tamura et al. (2007) "MEGA4: Molecular Evolutionary Genetics Analysis (MEGA) Software Version 4.0," *Mol. Biol. Evol.* 24:1596-1599.
Theis et al. (2004) "Antifungal Proteins: Targets, Mechanisms and Prospective Applications," *Cell Mol. Life Sci.* 61:437-455.
Theis et al. (Feb. 2003) "The Antifungal Protein from *Aspergillus giganteus* Causes Membrane Permeabilization," *Antimicrob. Agents Chemother.* 47(2):588-593.
Thevissen et al. (2005) "Fungal Sphingolipids as Targets for the Development of Selective Antifungal Therapeutics," *Curr. Drug Targets* 6:923-928.

Thevissen et al. (Feb. 6, 2004) "Defensins from Insects and Plants Interact with Fungal Glucosylceramides," *J. Biol. Chem.* 279(6):3900-3905.
Thevissen et al. (Aug. 15, 2000) "A Gene Encoding a Shingolipid Biosynthesis Enzyme Determines the Sensitivity of *Saccharomyces cerevisiae* to an Antifungal Plant Defensin from Dahlia (*Dahlia merckii*)," *Proc. Nat. Acad. Sci. USA* 97(17):9531-9536.
Thevissen et al. (2000) "Specific Binding Sites for an Antifungal Plant Defensin from Dahlia (*Dahlia merckii*) on Fungal Cells are Required for Antifungal Activity," *Mol. Plant. Microbe. Interact.* 13(1):54-61.
Van Der Weerden et al. (2004) "Permeabilization of Fungal Membranes by a Floral Defensin," ComBio 2004 Perth, Sep. 26-30, 2004, 1 page.
Van Der Weerden et al. (2005) "Defensin Gets Under Fungal 'Skin'," MPG2005, Melbourne, 1 page.
Van Der Weerden et al. (2005) "A Fluorescence Approach to Studying the Interaction of Defensin with Fungi," ComBio2005 Adelaide, Sep. 25-29, 2005, 1 page.
Van Der Weerden et al. (May 2007) "Defining the molecular interaction of plant defensins with fungal pathogen," 10th IUBMB Confernece & 36th Annual Meeting of SBBq, abstract publication.
Van Der Weerden et al. (May 23, 2008) "The Plant Defensin, NaD1, Enters the Cytolplasm of *Fusarium oxysporum* Hyphae," *J. Biol. Chem.* 283(21):14445-14452.
Veldhuis, et al., "Cellular DNA Content of Marine Phytoplankton Using Two New Fluorochromes: Taxonomic and Ecological Implications", *J. Phycol.* 1997, 33:527-541, Bigelow Laboratory for Ocean Sciences.
Williams et al. (1979) "Screening for Resistance to Blackleg of Crucifiers in the Seedling Stage," *Proceedings of Ecucarpia Cruciferae Conference*, Wageningen, The Netherlands, pp. 164-170.
International Search Report, Corresponding to International Application No. PCT/AU2009/000106, dated Mar. 20, 2009.
International Preliminary Report on Patentability, for corresponding WO application No. PCT/AU2009/000106, dated Mar. 20, 2009.
Prosecution history for related U.S. Appl. No. 12/708,421, filed Feb. 18, 2010 (downloaded Nov. 8, 2011), last document dated Jul. 26, 2011, 31 pp.
Prosecution history for related U.S. Appl. No. 12/535,443, filed Aug. 4, 2009 (downloaded Nov. 8, 2011), last document dated Sep. 6, 2011, 34 pp.
Office Action, dated May 23, 2012, for related U.S. Appl. No. 12/535,443, filed Aug. 4, 2009, 11 pp.
U.S. Appl. No. 15/296,952, filed Oct. 18, 2016.

* cited by examiner

| Fungicide | Concentration (ug/mL) | NaD1 (0.5 uM) | |
|---|---|---|---|
| | | Ee | Io |
| Triazole | | | |
| Propiconazole | 0.06 | 26 | 86 |
| | 0.25 | 35 | 95 |
| Tebuconazole | 0.06 | 53 | 99 |
| | 0.25 | 65 | 98 |
| Flusilazole | 0.06 | 38 | 83 |
| | 0.25 | 56 | 77 |
| Strobilurin | | | |
| Azoxystrobin | 2 | 75 | 88 |
| | 4 | 76 | 94 |
| Picoxystrobin | 2 | 75 | 95 |
| | 4 | 75 | 96 |

| Fungicide | Concentration (ug/mL) | NaD1 (0.5 uM) | |
|---|---|---|---|
| | | Ee | Io |
| Strobilurin | | | |
| Azoxystrobin | 0.25 | 48 | 72 |
| | 1.0 | 65 | 93 |
| Picoxystrobin | 0.125 | 51 | 79 |
| | 0.25 | 60 | 86 |
| Fluoxastrobin | 0.125 | 15 | 41 |
| | 0.25 | 48 | 87 |
| Triazole | | | |
| Propiconazole | 1 | 56 | 75 |
| | 4 | 59 | 95 |

FIGURE 3A

| Line | Fungicide | Mortality | Average disease score |
|---|---|---|---|
| Non-transgenic Coker 315 | - | 15% | 0.9 |
| Non-transgenic Coker 315 | + | 19% | 1.1 |
| Line 35.125.1 | - | 8% | 0.7 |
| Line 35.125.1 | + | 0 | 0.1 |

FIGURE 3B

| Line | Fungicide | Mortality | Average disease score |
|---|---|---|---|
| Non-transgenic Coker 315 | - | 18% | 1.7 |
| Non-transgenic Coker 315 | + | 13% | 1.6 |
| Line 35.125.1 | - | 7% | 1.2 |
| Line 35.125.1 | + | 0 | 1.0 |

FIGURE 3G

| Fungicide | Ee | Io |
|---|---|---|
| Jockey | 9% | 22% |
| Dynasty | 1% | 21% |
| Redigo | 4% | 17% |
| HEC5725 | 8% | 15% |

| Fungicide | Concentration (ug/mL) | NaD1 (0.5 uM) | |
|---|---|---|---|
| | | Ee | Io |
| Triazole | | | |
| Propiconazole | 0.03 | 57 | 93 |
| | 0.06 | 61 | 93 |
| Tebuconazole | 0.03 | 24 | 48 |
| | 0.06 | 38 | 81 |
| Flusilazole | 0.03 | 49 | 92 |
| | 0.06 | 69 | 93 |

FIGURE 5A

| Line | Fungicide (Dynasty) | Germination (%) | Survival (%) | Uninfected plants (%) | Verticillium rank |
|---|---|---|---|---|---|
| Non-transgenic Coker 315 | - | 60 | 65 | 1.0 | nd |
| Line 35.125.1 | - | 63 | 62 | 3.6 | nd |
| Non-transgenic Coker 315 | + | 80 | 58 | 0.4 | 10 |
| Line 35.125.1 | + | 80 | 63 | 5.1 | 101 |
| Sicala V2 | + | 72 | 81 | 3.1 | 100 |

FIGURE 5B

| Line | Fungicide (Dynasty) | Yield (bolls) (kilograms per hectare) | Yield (lint)* (kilograms per hectare) |
|---|---|---|---|
| Non-transgenic Coker 315 | - | 1562 | 688[a] |
| Line 35.125.1 | - | 1812 | 811[a] |
| Non-transgenic Coker 315 | + | 1261 | 543[a] |
| Line 35.125.1 | + | 2646 | 1184[b] |
| Sicala V2 | + | 4117 | 1828[c] |

* Means follows by the same letter are not significantly different (Student-Newman-Keuls test, $p<0.05$)

FIGURE 6C

| Fungicide | Concentration (ug/mL) | NaD1 (0.5 uM) | |
|---|---|---|---|
| | | Ee | Io |
| Triazole | | | |
| fluquinaconazole | 0.25 | 42 | 63 |
| | 0.5 | 61 | 74 |
| prothioconazole | 0.25 | -21 | 27 |
| | 1.0 | 16 | 70 |

FIGURE 8C

| Protein | Source | Cultivar name | Common name | Tissue | Mass (kDa) |
|---|---|---|---|---|---|
| NaD1 | *Nicotiana alata* | | Ornamental tobacco | Flowers | 5296 |
| NaD2 | *Nicotiana alata* | | Ornamental tobacco | Flowers | 5256 |
| NaD4 | *Nicotiana alata* | | Ornamental tobacco | Flowers | ND |
| Tom def 1 | *Solanum lycopersicum cerasiforme* | Tommy toe | Cherry tomato | Flowers | 5253 |
| Tom def 2 | *Solanum lycopersicum cerasiforme* | Tommy toe | Cherry tomato | Flowers | 5426 |
| Tom def 3 | *Solanum lycopersicum cerasiforme* | Tommy toe | Cherry tomato | Flowers | 5409 |
| FBC1 | *Vicia faba* | Cairo | Faba bean | Seeds | 5233 |
| SFSH4 | *Helianthus annuus* | Hysun38 | Sunflower | Seeds | 4472 |

| Defensin | Concentration (µM) | Tebuconazole (0.6 mg/L) | |
|---|---|---|---|
| | | Ee | Io |
| NaD1 | 0.4 | 40 | 67 |
| NaD2 | 3.3 | 65 | 67 |
| NaD4 | 1.5 | 26 | 50 |
| Tom def 1 | 5.0 | 49 | 47 |
| Tom def 2 | 5.0 | 9 | 5 |
| Tom def 3 | 0.4 | 17 | 39 |
| SFSH4 | 5.0 | 21 | 20 |
| FBC1 | 5.0 | 40 | 42 |

FIGURE 8N

| Defensin | Relative Permeability Index | Antifungal Activity (IC50, µM) | Synergy |
|---|---|---|---|
| NaD1 | 1 | 0.5 | + |
| NaD2 | <0.05 | 4 | - |
| NaD4 | 0.5 | 1.1 | + |
| Tom def 1 | <0.05 | 4 | - |
| Tom def 2 | 0.4 | 0.85 | - |
| Tom def 3 | 1.1 | 0.45 | + |
| FBC1 | <0.05 | 7 | - |
| SFSH4 | 0.12 | 3 | - |

SEQUENCE LISTING

<160> NUMBER OF SEQ ID NOS: 1

<210> SEQ ID NO 1
<211> LENGTH: 47
<212> TYPE: PRT
<213> ORGANISM: Nicotiana alata

<400> SEQUENCE: 1

```
Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45
```

METHODS FOR PROTECTING PLANTS WITH ANTIFUNGAL COMPOSITIONS

CROSS REFERENCE TO RELATED APPLICATIONS

This application is a continuation of co-pending U.S. patent application Ser. No. 12/362,657, filed Jan. 30, 2009, which claims the benefit of U.S. Provisional Application No. 61/025,655, filed Feb. 1, 2008 and from U.S. Provisional Application No. 61/085,682, filed Aug. 1, 2008. Each of these applications is incorporated by reference in its entirety herein.

ACKNOWLEDGEMENT OF FEDERAL FUNDING

Not applicable.

FIELD

The present invention relates to strategies for the protection of plants from infection or infestation by pathogenic agents, especially fungi, as well as from disease conditions associated therewith.

BACKGROUND

References are cited herein to indicate state of the art and are not to be taken as acknowledgement of specific relevance to patentability of the invention.

Bibliographic details of the publications referred to by author are provided at the end of the specification.

Crop losses due to infection by fungal pathogens are a major problem in the agricultural industry and each year, millions of dollars are spent on the application of fungicides to curb these losses (Oerke, 2003). Nature is a rich source of antimicrobial peptides, many of which exhibit antifungal activity.

Antimicrobial peptides that have evolved to protect organisms from pathogens. Their specificity appears to depend largely on the organism from which they originate, probably due to evolutionary pressure placed on these organisms by various pathogens. As such, peptides isolated from mammalian species generally exhibit a higher degree of activity toward bacterial pathogens compared to fungal pathogens, presumably due to the higher risk of infection from bacteria. In contrast, plant antimicrobial peptides generally display higher antifungal activity due to the higher risk of fungal infection faced by plants.

Plant defensins represent one class of antimicrobial peptide (reviewed by Lay and Anderson (2005)). There is a wide variety of defensins with differing spatial and temporal patterns of expression and spectra of activity. These include RsAFP1 and RsAFP2 from radish, Ah-AMP4 from *Aesculus hippocatanum*, and AlfAFP from alfalfa, pI39 and pI230 from pea, and DmAMP1 from dahlia as well as ZmESR6, PhD2, PhD1, BSD1, RsAFP4, WT1, RsFP3, AhAMP1, CtAMP1, HsAFP1, HvAMP1, PsD1, AX2, AX1, SoD2, VaD1, gD1, NaD2, J1-2, SD2 and EGAD1, and preferably floral defensins such as NaD1 and NaD4 from *Nicotiana alata* and Tomdef2 and Tomdef3 from *Lycopersicum cerasiforme*.

The mechanisms underlying the specificity of these peptides remain unknown, although interactions with the cell surface are presumed to be involved. Since membrane permeabilization is a common activity of many antimicrobial peptides and the membrane composition of various cell types is highly variable, the presence of specific lipids is postulated in some cases to be responsible for peptide susceptibility. In particular, the plasma membrane of bacterial cells contains negatively charged phospholipids in the outer layer while mammalian cells do not (Matsuzaki, 1999). These negatively charged lipids could interact with positively charged antimicrobial peptides. In support of this hypothesis, in vitro studies have demonstrated that the presence of negatively charged lipids is important for the membrane permeabilizing activity of a number of antimicrobial peptides (Matsuzaki et al, 1995; Matsuzaki, 1999; Ladokhin and White, 2001; Epand et al, 2006).

Membrane permeabilization has been suggested as a mechanism for some plant defensins, although the mechanism of permeabilization has not been investigated. In the case of the plant defensins RsAFP2 and DmAMP1, permeabilization is proposed to involve a specific receptor on the cell surface. The presence of specific sphingolipids in the plasma membrane is also required for the activity of these defensins, possibly as binding sites (Thevissen et al, 2000a, b; Thevissen et al, 2004; Thevissen et al, 2005, Ramamoorthy et al, 2007).

Chemical fungicides are quite commonly used in agricultural and horticultural settings. Strobilurins and triazoles are particularly important for use in these industries.

Strobilurins include strobilurins A through H, azoxystrobin, kresoxim-methyl, picoxystrobin, fluoxastrobin, oryzastrobin, dimoxystrobin, pyraclostrobin, metominostrobin, and trifloxystrobin. For a review of the fungicidal strobilurins, see Bartlett et al (2002). As a class, the strobilurins are part of the $Q_o1$ (Quinone outside inhibitors) cross-resistance group, and they inhibit sensitive organisms by binding cytochrome b and inhibiting electron transport and ATP synthesis.

The triazole fungicides are characterized as demethylase inhibitors, and they interfere with sterol synthesis in sensitive fungi. Triazole fungicides are described in U.S. Pat. No. 4,767,777, for example.

There is a need in the art for improved economies of agricultural production and improvement of crop yields. Fungal disease is a significant source of yield loss and current strategies for fungus control are both expensive and potentially damaging to the environment. There is a need for new systems for protecting agronomic and ornamental plants from disease, especially fungal disease. Disclosed herein is a system for reducing economic loss resulting from damage to crops and ornamental plants caused by pathogenic agents, such as fungal agents. In addition to significantly reducing plant damage, the cost of production can be reduced by decreased use of chemical pesticides.

SUMMARY

The present invention provides, inter alia, a system for protecting a plant from a fungal infestation or infection and/or for reducing the incidence or severity of disease associated with the pathogen. In an embodiment the pathogen is a fungal agent and the disease is a fungal disease. The system encompasses at a minimum, two components, a plant defensin which is not in nature expressed by the plant, and a chemical agent, in particular a chemical fungicide. A surprising property of the system is the property of synergism observable in the combination of an anti-fungal defensin and a chemical fungicide as described herein. As one example among many disclosed herein, there is synergistic inhibition of *Fusarium graminearum* and *Fusarium*

*oxysporum* (Fov) by a combination of at least one plant defensin, for example NaD1 or an antifungal variant thereof, and at least one of various chemical fungicides including, but not limited to, a strobilurin and triazole. Any fungus individually susceptible to inhibition by each of the components of the system can be more effectively controlled by using the combination than by either component used by itself, despite using a lower concentration of the chemical fungicide in the combination approach.

A fungus is "susceptible to inhibition" by each of the individual components of the system if it can be shown that each component individually exerts an inhibitory activity against the fungus, or the components in combination exert a combined inhibitory effect that is synergistic.

In certain studies described herein, the effect of a component of the system on permeability of fungal cells is measured. A substance whose location can be identified, whether inside or outside of a fungal cell, is employed. The substance is sometimes referred to herein as a "permeability indicator compound". A permeability indicator compound is one whose presence either inside or outside of a cell, can be detectably measured by virtue of possessing a detectable property such as fluorescence, radio-label, immunological characteristic or the like. Also, a permeability indicator compound is one which under normal conditions remains extracellular, and would not be detected intracellularly unless cell permeability had been altered from the normal physiological condition of the cell. In principle, an indicator of permeability could be one normally retained intracellularly, only leaking out under abnormal conditions, but the former type of indicator is the more common. Examples of permeability indicator compounds include fluorescent dyes that bind to nucleic acids such as SYTOX® Green or propidium iodide. Other examples include FITC-labeled dextrans or an immuno-gold labeled antibody, whose locus can be seen by microscopy. Fluorescently tagged defensin itself can be used as a permeability indicator compound. The term "detectable amount" is intended to convey that differences in amount of the permeability indicator compound can be semi-quantitatively assessed, sufficient for comparison purposes. For the purpose of comparing the possible effect of a plant defensin on fungal cell permeability, the plant defensin NaD1 is used as a basis for comparison. As described herein, the effect of a given defensin on the permeability of a fungal cell can be quantified as a "relative permeability index" by the use of a permeability indicator compound.

Embodiments of the present invention include those where the defensin is any defensin with fungicidal and/or fungistatic activity against at least one plant pathogenic fungus. Examples of such antifungal defensins include, without limitation RsAFP1 and RsAFP2 from radish, Ah-AMP4 from *Aesculus hippocatanum*, and AlfAFP from alfalfa, pI39 and pI230 from pea, and DmAMP1 from dahlia as well as ZmESR6, PhD2, PhD1, BSD1, RsAFP4, WT1, RsFP3, AhAMP1, CtAMP1, HsAFP1, HvAMP1, PsD1, AX2, AX1, SoD2, VaD1, gD1, NaD2, J1-2, SD2 and EGAD1, and preferably floral defensins such as NaD1 and NaD4 from *Nicotiana alata* and Tomdef2 and Tomdef3 from *Lycopersicum cerasiforme*. Chimeric defensin molecules and/or defensin variants which retain antifungal activity can also be employed in the present system for plant protection.

Compounds useful in embodiments of the present invention include but are not limited to wholly or locally systemic (local penetrant) antifungal compounds from the following classes: strobilurins, triazoles, anilinopyrimidines, valinamide carbamates, benzimidazoles, thiophanates, acylalanines, carbamates, ethyl phosphonates, dicarboximides and carboxamides. Examples of useful strobilurins include without limitation, azoxystrobin, kresoxim-methyl, picoxystrobin, fluoxastrobin, oryzastrobin, dimoxystrobin, pyraclostrobin, metominostrobin, trifloxystrobin, enestrobin. Examples of useful triazoles include without limitation, azaconazole, biteranol, bromuconazole, cyproconazole, difenoconazole, diniconazole, epoxyconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconaxole, triadmefon, triadimenol, triticonazole. Examples of useful anilnopyrimidines include without limitation, pyrimethanil, cyprodinil, mepanipyrim. Examples of useful valinamide carbamates include without limitation, iprovalicarb, benthiavalicarb and valiphenal.

Examples of useful benzimidazoles include without limitation, benomyl, carbendazim, fuberidazole, thiabendazole. Examples of useful thiophanates include without limitation, thiophanate, thiophanate-methyl. Examples of useful acylalanines include without limitation, metalaxyl-M, benalaxyl, metalaxyl, furalaxyl. Examples of useful carbamates include without limitation, propamocarb, iodocarb, prothiocarb. Examples of useful ethyl phosphonates include without limitation, fosetyl-A1. Examples of useful dicarboximides include without limitation, chlozolinate, iprodione, procymidone, viclozolin. Examples of useful carboxamides include without limitation, benodanil, mepronil, flutolanil, fenfuram, thifluzamide, boscalid, oxycarboxin, carboxin, penthioopyrad and furametpyr.

Plants which can be protected from fungal infection by the system of the present invention include those which are susceptible to a fungus which is sensitive to a chemical fungicide, especially a strobilurin or a triazole, and a plant defensin which can be expressed as a transgene in that plant or to which a composition comprising the defensin can be applied. Preferably the plant can be a monocotyledonous plant, especially a plant from the Poaceae family, as well as grains, such as maize, barley, wheat, rice and the like, or a dicotyledonous plant, especially from the families Solanaceae, Brassicaceae, Malvaceae, and Fabaceae.

Infection and damage from many fungal pathogens, especially those which are filamentous fungi, can be controlled in many plant species using the present system. Examples of controllable fungal and oomycete pathogens include, but are not limited to, *Fusarium, Verticillium, Pythium, Rhizoctonia, Sclerotinia, Leptosphaeria, Phytophthora, Colletotrichum, Diplodia, Cercospora, Aspergillus, Macrophomina, Phialophora, Diaporthe, Thielaviopsis, Alternaria, Phoma*, Phymatotrichopsis and rust and smut fungi, such as *Puccinia, Phakopsora* and *Ustilago*. Important applications include, without being limiting, the synergistic combinations of a chemical fungicide compound and an antifungal defensin used, e.g., to protect canola from black leg, corn or wheat (or other grains) from *Fusarium graminearum*, and cotton from *Fusarium oxysporum*. The present invention further provides a use of a first component and a second component on a plant, each of said first and second components being an inhibitor of a given susceptible fungus, the first component being a plant defensin which is not in nature expressed by said first mentioned plant, the second component being a chemical fungicide in the inhibition of the fungus when combined in a contact with the fungus on said plant.

BRIEF DESCRIPTION OF THE FIGURES

FIGS. 1A through 1E are graphical representations showing the effect of combinations of the defensin NaD1 and fungicides on the growth of *Fusarium graminearum* in vitro. Fungal growth was measured by the increase in optical density at 595 nm (A595) achieved at 44, 45 or 68 hours after inoculation of the growth medium, (vertical axis) and is plotted against fungicide concentration (mg/L) on the horizontal axis. The solid line connects sample results obtained in the presence of 0 µM NaD1; the Dashed, Dotted and Dot-Dash lines represent various concentrations of NaD1 as indicated on the graphs. Error bars indicate 95% confidence intervals. FIG. 1A. Combination of NaD1 and propiconazole. Growth at 44 hours. FIG. 1B. Combination of NaD1 and tebuconazole. Growth at 44 hours. FIG. 1C. Combination of NaD1 and flusilazole. Growth at 44 hours. FIG. 1D. Combination of NaD1 and azoxystrobin. Growth at 45 hours. FIG. 1E. Combination of NaD1 and picoxystrobin. Growth at 45 hours. FIG. 1F provides a comparison of the expected effect from an additive response (Ee) with the observed response (Io) in the fungal bioassays illustrated in FIGS. 1A-E. FIG. 1G. Combination of NaD1 and propiconazole. Growth at 45 hours. FIG. 1H. Combination of NaD1 and propiconazole. Growth at 68 hours.

FIGS. 2A through 2F and FIGS. 2H through I show the effect of combinations of the defensin NaD1 and fungicides on the growth of *Fusarium oxysporum* f. sp. *vasinfectum* (Fov), in vitro. Fungal growth was measured by the increase in optical density at 595 nm (A595) achieved at 45, 45.5, 47 or 48 hours after inoculation of the growth medium, (vertical axis) and is plotted against fungicide concentration (mg/L) on the horizontal axis. The solid line connects sample results obtained in the presence of 0 µM NaD1; the Dashed, Dotted and Dot-Dash lines represent various concentrations of NaD1 as indicated on the graphs. Error bars indicate 95% confidence intervals. FIG. 2A. Combination of NaD1 and azoxystrobin. Growth after 47 hours. Azoxystrobin concentrations 0-1 mg/L. FIG. 2B. Combination of NaD1 and azoxystrobin. Growth after 47 hours. Azoxystrobin concentrations 0-4 mg/L. FIG. 2C. Combination of NaD1 and picoxystrobin. Growth after 48 hours. Picoxystrobin concentrations 0-1 mg/L. FIG. 2D. Combination of NaD1 and fluoxastrobin. Growth after 45.5 hours. Fluoxastrobin concentrations 0-1 mg/L. FIG. 2E. Combination of NaD1 and propiconazole. Growth after 45 hours. Propiconazole concentrations 0-4 mg/L. FIG. 2F. Combination of NaD1 and propiconazole. Growth after 47 hours Propiconazole concentrations 0-1 mg/L. FIG. 2G. Comparison of the expected effect from an additive response (Ee) with the observed response (Io) in the fungal bioassays illustrated in FIGS. 2A-F. FIG. 2H. Combination of NaD1 and picoxystrobin. Growth after 47 hours. Picoxystrobin concentrations 0-0.125 mg/L. FIG. 2I. Combination of NaD1 and picoxystrobin. Growth after 47 hours. Picoxystrobin concentrations 0-1 mg/L.

FIGS. 3A and B are tabulated representations showing the effect of the combination of fluoxastrobin and NaD1 in a transgenic cotton plant upon infection by *Fusarium oxysporum* f sp. *vasinfectum* (Fov). FIG. 3A, Glasshouse bioassay and FIG. 3B, Growth cabinet bioassay assessing the combination of fluoxastrobin and the NaD1 defensin on infection of cotton with *Fusarium oxysporum* f. sp. *vasinfectum* (Fov). Seeds of non-transgenic Coker 315 and transgenic Coker 315 expressing NaD1 (line 35.125.1, U.S. patent application Ser. No. 12/105,956) with and without fluoxastrobin seed coat. Results represent percentage mortality and average disease score after 8 weeks for the glasshouse test and 5 weeks for the growth cabinet test. Forty eight and thirty seeds were used for the glasshouse and growth cabinet tests respectively. FIGS. 3C-3F illustrate the results obtained in a field trial bioassay to assess the effect of the combination of a transgene expressing the defensin NaD1 in cotton (transgenic line 35.125.1) and seed coating with various chemical fungicides upon infection by *Fusarium oxysporum* f. sp. *vasinfectum* (Fov). Results represent percentage mortality from 14 to 57 days post-germination. About 1100-1400 germinated seeds were obtained and monitored for each treatment. Error bars represent 95% confidence levels. Seeds of non-transgenic Coker 315 and transgenic Coker expressing NaD1 (line 35.125.1) with and without seed coats of FIG. 3C Jockey®, FIG. 3D Dynasty®, FIG. 3E Redigo® and FIG. 3F HEC5725 respectively. FIG. 3G. Comparison of the expected improved survival from an additive response (Ee) with the observed improved survival (Io) in the field bioassays illustrated in FIGS. 3C-F.

FIGS. 4A through 4C are graphical representations showing the effect of combinations of the defensin NaD1 and fungicides on the growth of *Verticillium dahliae* in vitro. Fungal growth was measured by the increase in optical density at 595 nm (A595) achieved at 118 hours after inoculation of the growth medium, (vertical axis) and is plotted against fungicide concentration (mg/L) on the horizontal axis. The solid line connects sample results obtained in the presence of 0 µM NaD1; the Dashed, Dotted and Dot-Dash lines represent various concentrations of NaD1 as indicated on the graphs. Error bars indicate 95% confidence intervals. FIG. 4A. Combination of NaD1 and propiconazole. FIG. 4B. Combination of NaD1 and tebuconazole. FIG. 4C. Combination of NaD1 and flusilazole. FIG. 4D. Comparison of the expected effect from an additive response (Ee) with the observed response (Io) in the fungal bioassays illustrated in FIGS. 4A-C.

FIGS. 5A and 5B provide tabulated representations showing the effect of the combination of the seed coat Dynasty® (Registered Trademark) (Syngenta) and NaD1 in a transgenic cotton plant on infection by *Verticillium dahliae* in the field. FIG. 5A. Results of field trial assessing seeds of non-transgenic Coker 315 and transgenic Coker 315 expressing NaD1 (line 35.125.1, U.S. patent application Ser. No. 12/105,956) with and without Dynasty® (Registered Trademark) seed coat and the industry standard Sicala V2 with Dynasty® (Registered Trademark) seed coat. Results represent percentage germination after 4 weeks, percentage survival of germinated plants after 18 weeks and percentage uninfected plants at the end of the trial (30 weeks). *Verticillium* rank was determined at harvest. Five hundred seeds were used for each treatment. FIG. 5B. The yield of cotton bolls and lint from the plants described in FIG. 5A.

FIGS. 6A and 6B are graphical representations showing the effect of combinations of the defensin NaD1 and fungicides on the growth of *Leptosphaeria maculans* in vitro. Fungal growth was measured by the increase in optical density at 595 nm (A595) achieved at 96 hours after inoculation of the growth medium (vertical axis) and is plotted against fungicide concentration (mg/L) on the horizontal axis. *L. maculans* spores were pre-germinated for 48 hours in liquid V8 medium before the addition of combinations of NaD1 and fungicide. The solid line connects sample results obtained in the presence of 0 µM NaD1; the Dashed, Dotted and Dot-Dash lines represent various concentrations of NaD1 as indicated on the graphs. Error bars indicate 95% confidence intervals. FIG. 6A. Combination of NaD1 and prothioconazole. FIG. 6B. Combination of NaD1 and fluquinconazole. FIG. 6C. Comparison of the expected effect from an additive response (Ee) with the observed response (Io) in the fungal bioassays illustrated in FIGS. 6A-6B. Certain values are negative (i.e. more growth than the control) because "0 uM NaD1, 0.25 mg/L prothioconazole" has more growth than "0 uM NaD1, 0 mg/L prothioconazole" as does "0.5 uM NaD1, 0 mg/L prothioconazole".

FIG. 7A is a graphical representation of the NaD1 level as determined by ELISA in the leaves of the T3 generation of line CAT13.26 transformed with pHEX3. Purified NaD1 from *Nicotiana alata* was used as the standard.

FIGS. 7B and 7C are bar graphs showing the results of the glasshouse bioassay with transgenic canola infected with *Leptosphaeria maculans*. Thirty seeds of non-transgenic RI64 and transgenic RI64 expressing NaD1 (CAT13.26) were grown in the glasshouse for 10 days. The cotyledons were then inoculated with spores of *Leptosphaeria maculans* and the area of the lesion measured at Day 10 (FIG. 7B) and Day 17 (FIG. 7C).

FIG. 8A is a RP-HPLC elution profile of proteins from tomato flowers. Proteins that had bound to SP-Sepharose were collected and separated on an analytical Zorbax 300SB-C8 RP-HPLC column using an Agilent Technologies 1200 series system and a 40 min linear gradient (0-100% Buffer B). Eluted proteins were detected by absorbance at 215 nm.

Figure 8A:
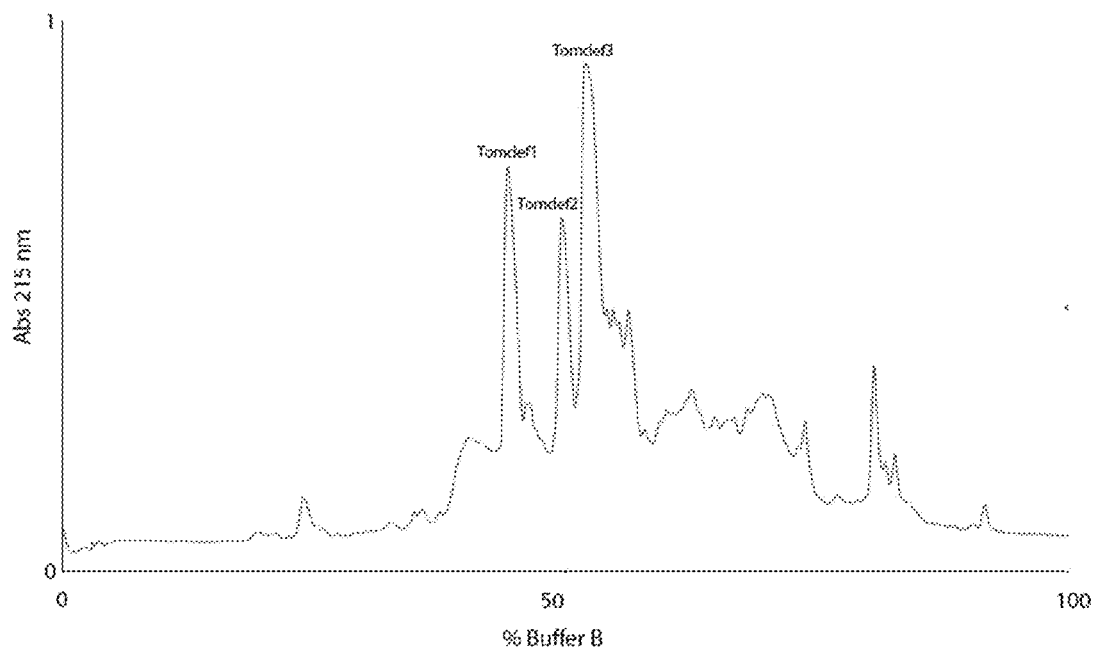
FIG. 8B is a RP-HPLC elution profile of proteins from *N. alata* flowers. Proteins that had bound to SP-Sepharose were fractioned further on a preparative Vydac C8 RP-HPLC column using a Beckman Coulter System Gold and a 40 min linear gradient (0-100% Buffer B).
FIG. 8C is a table listing the plant source and mass of the seed and floral defensins that were tested.
FIG. 8D is a graphical representation of SYTOX green uptake into *F. graminearum* hyphae induced by various concentrations of NaD1.
FIG. 8E is a graphical representation of ATP release from *F. graminearum* hyphae induced by various concentrations of NaD1.
Figure 8B:
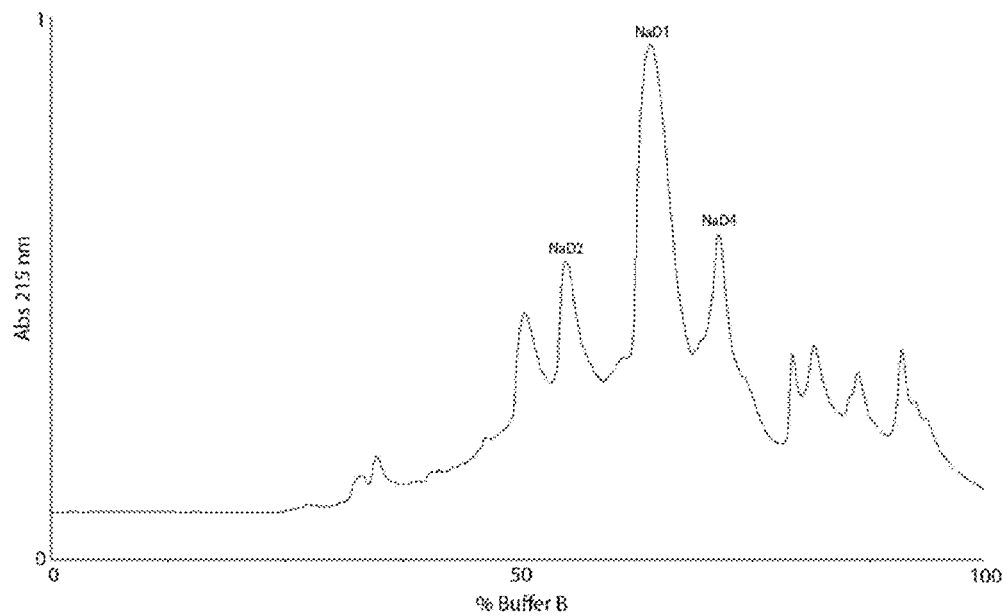
Figure 8D:
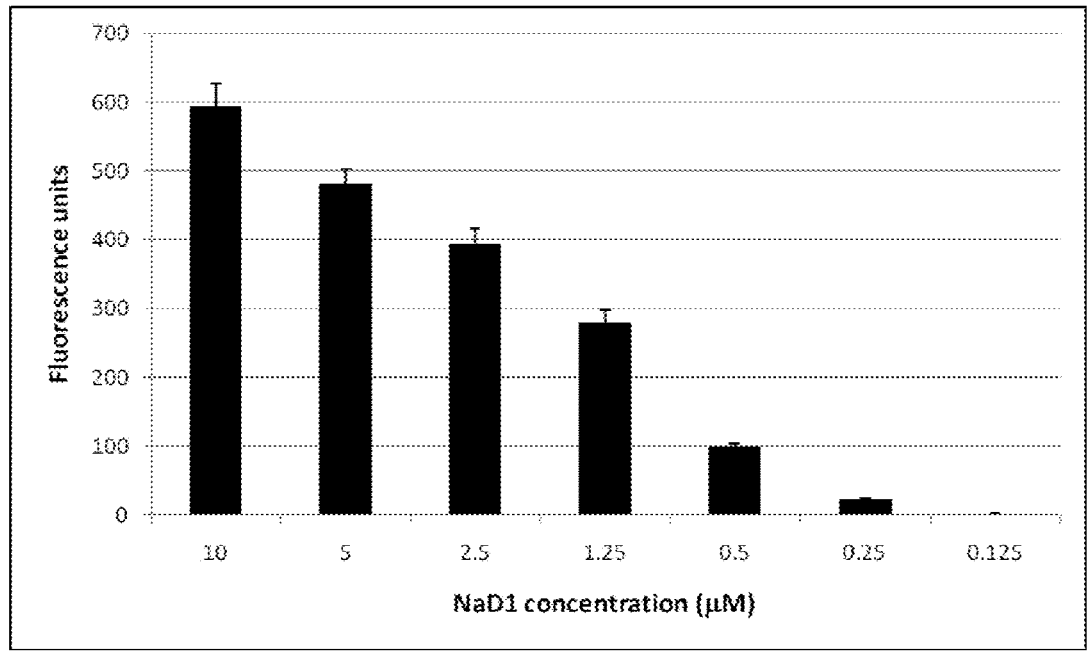
Figure 8E:
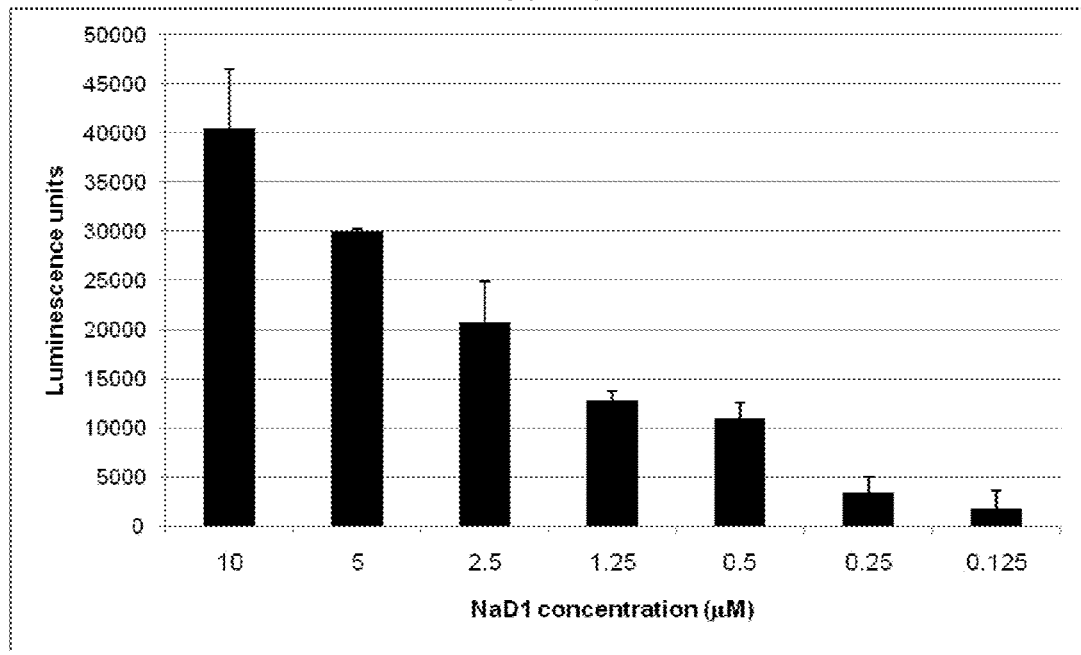
Figure 8F:
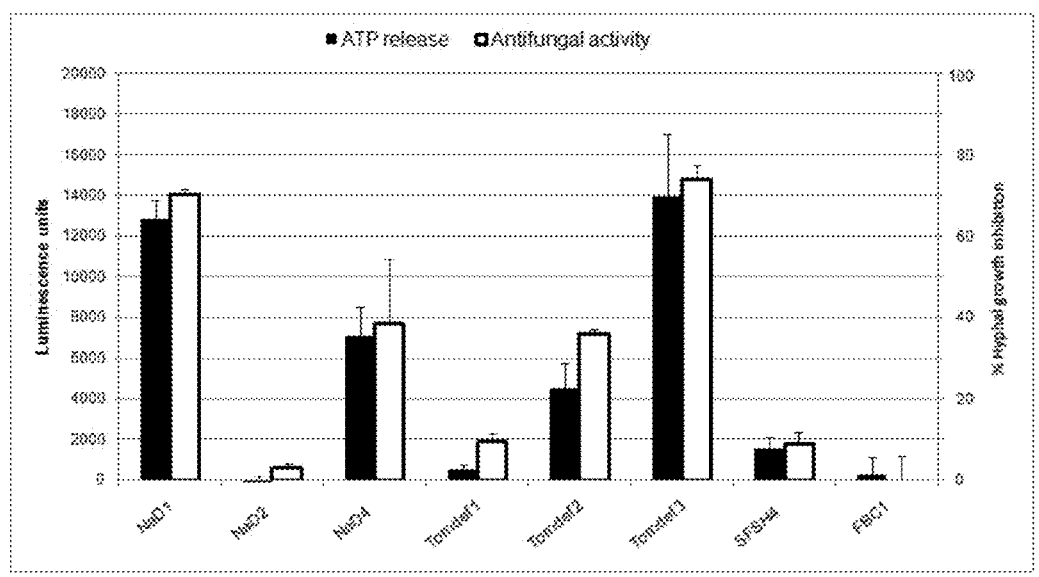
Figure 8G:
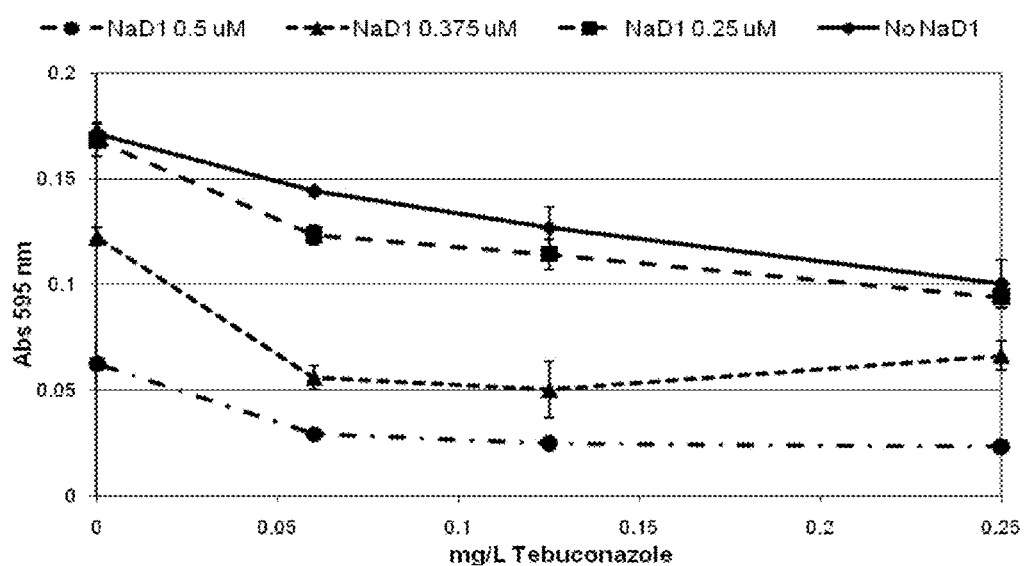
Figure 8H:
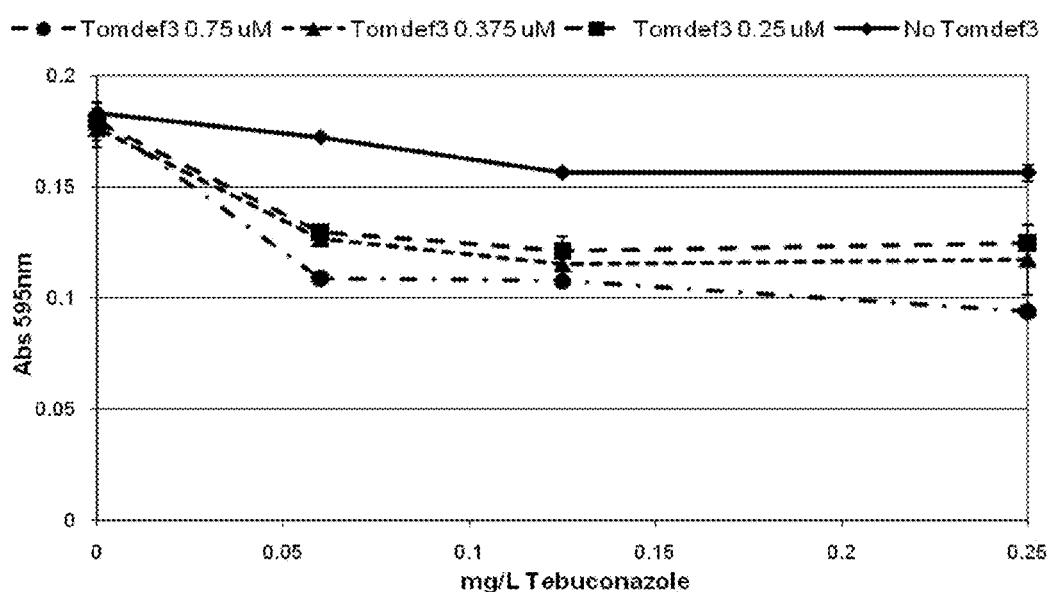
Figure 8I:
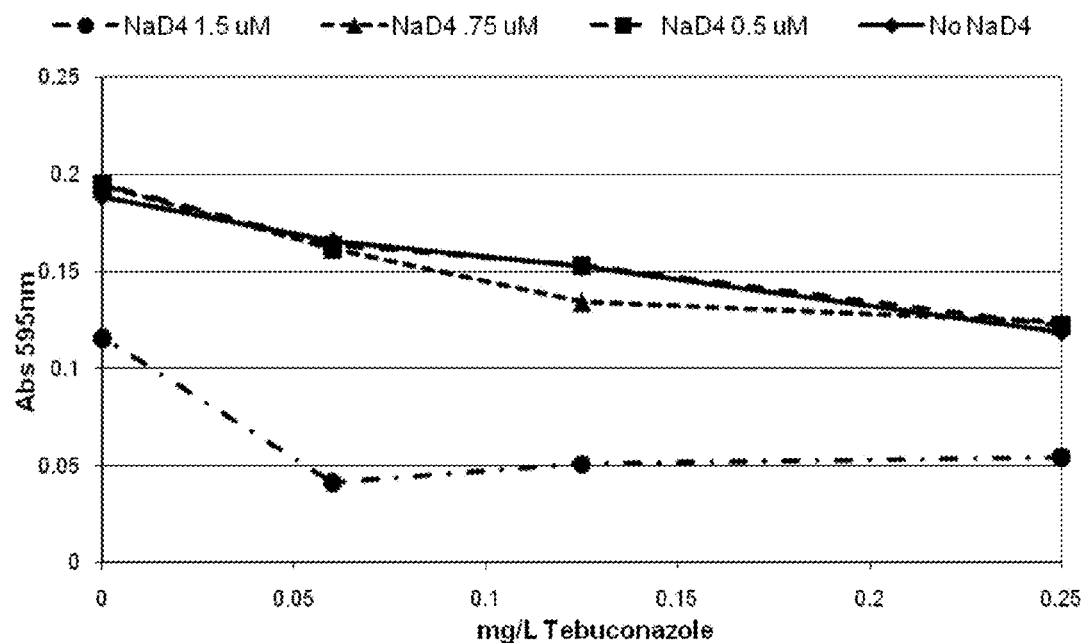
Figure 8J:
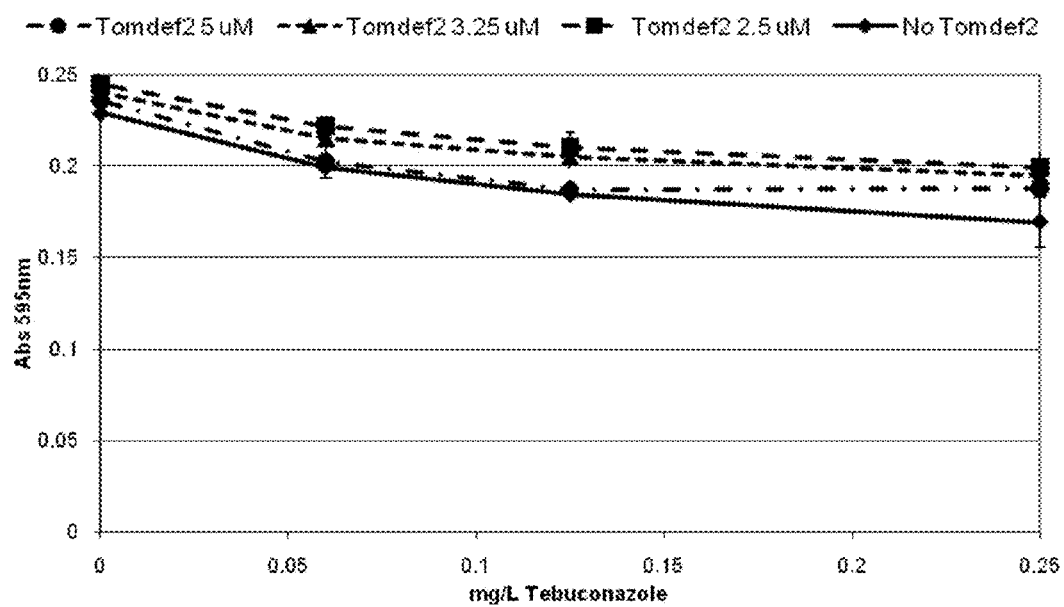
Figure 8K:
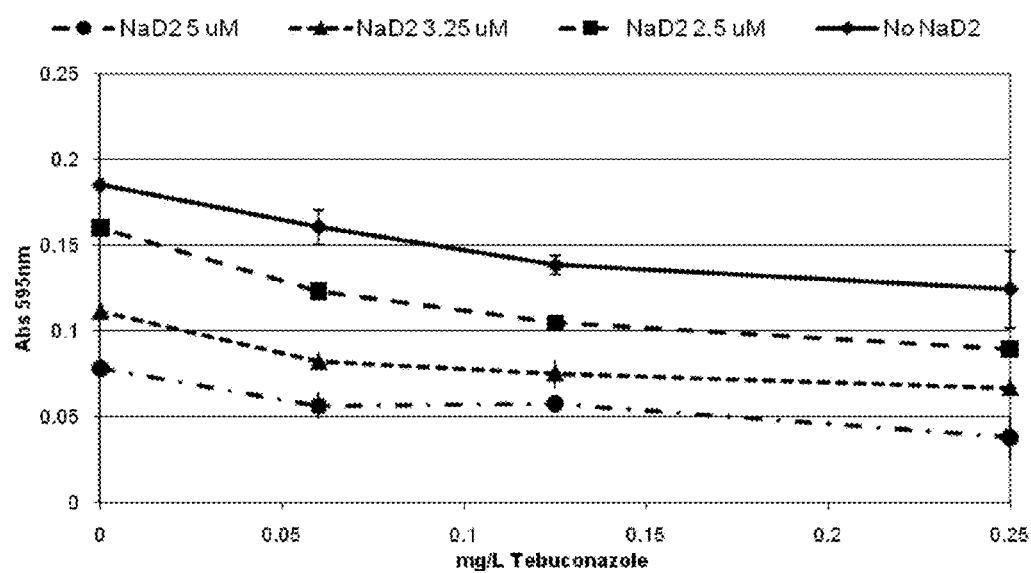

FIG. 8F is a graphical representation of the relative membrane permeabilizing activity as well as the relative antifungal activity of each of the defensins on *F. graminearum* hyphae. Relative permeabilization (column graph, left axis) was estimated from the relative ATP release induced after the addition of the various defensins. Fungal growth (line axis, right axis) was measured by the increase in optical density at 595 nm (Abs 595 nm) achieved at 24 h after inoculation of the growth medium. See FIG. 8C for identification of the defensins.

FIGS. 8G-8L are graphical representations showing the effect of various defensins in combination with fungicides on the growth of *F. graminearum*. Fungal growth was measured by the increase in optical density at 595 nm (Abs 595 nm) achieved at 24 h after inoculation of the growth medium, (vertical axis) and is plotted against fungicide concentration (mg/L) on the horizontal axis. The solid line connects sample results obtained in the absence of NaD1; the Dashed, Dotted and Dot-Dash lines represent various concentrations of NaD1 as indicated on the graphs. Error bars indicate standard error of the mean.

Figures 8L, 8M:
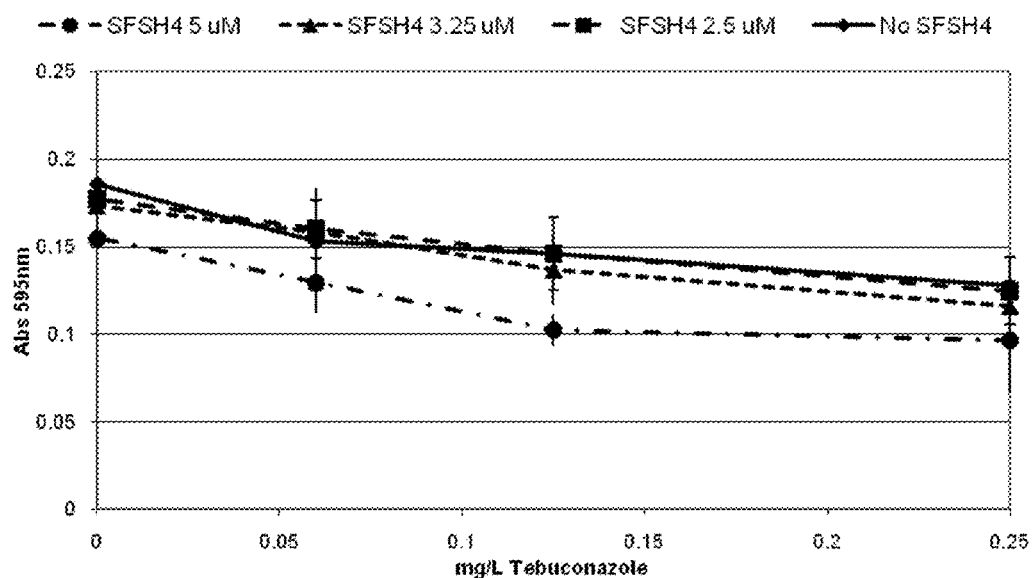

FIG. 8M is a comparison of the expected effect from an additive response (Ee) with the observed response (Io) in the fungal bioassays illustrated in FIGS. 8G-8L.

FIG. 8N is a table showing the relative permeability index of the defensins listed in FIG. 8C as well as their relative antifungal activity on *F. graminearum* and relative synergy with the fungicide tebuconazole. Permeability index (PI) was defined as the relative amount of luminescence units obtained in 10 min with 1 µM defensins compared to the luminescence obtained with 1 µM NaD1 which was given a PI of 1.

Figure 9A:
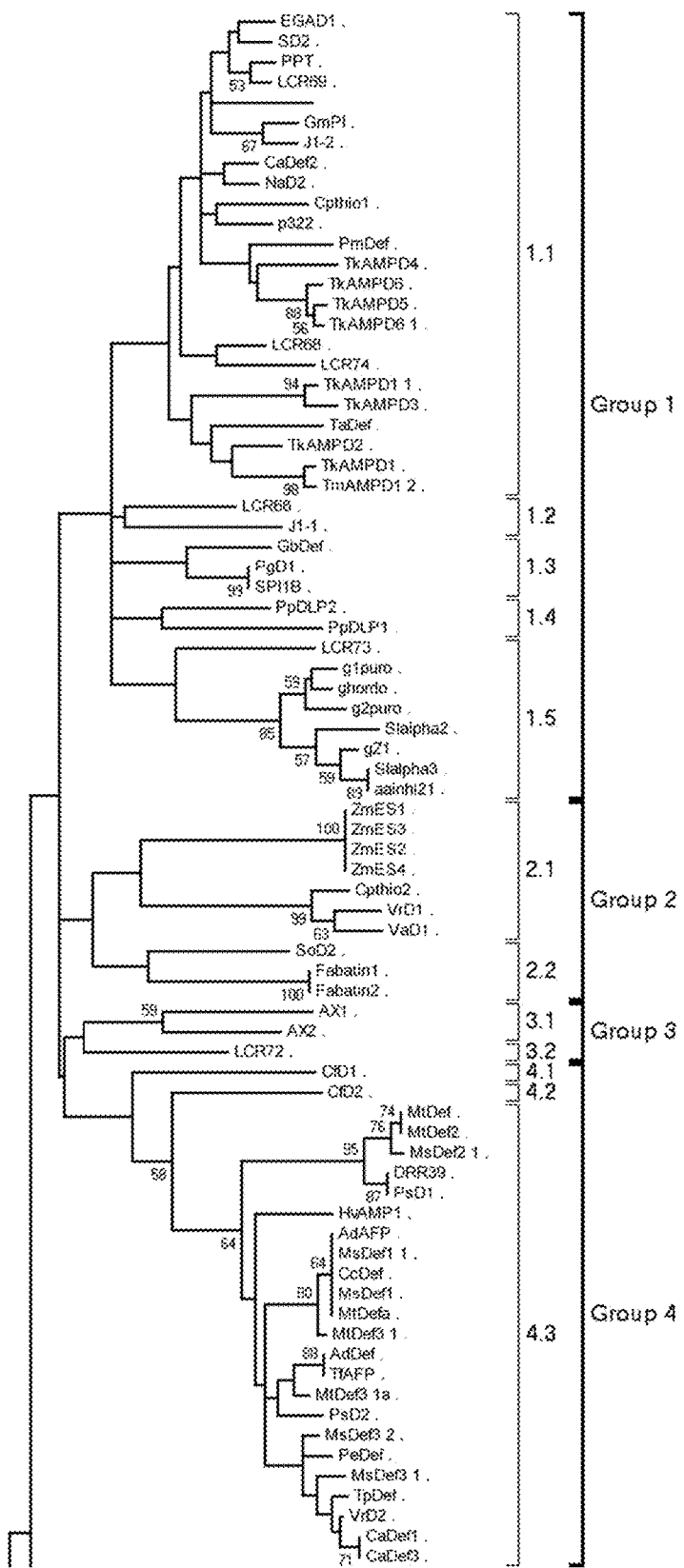
Figure 9B:
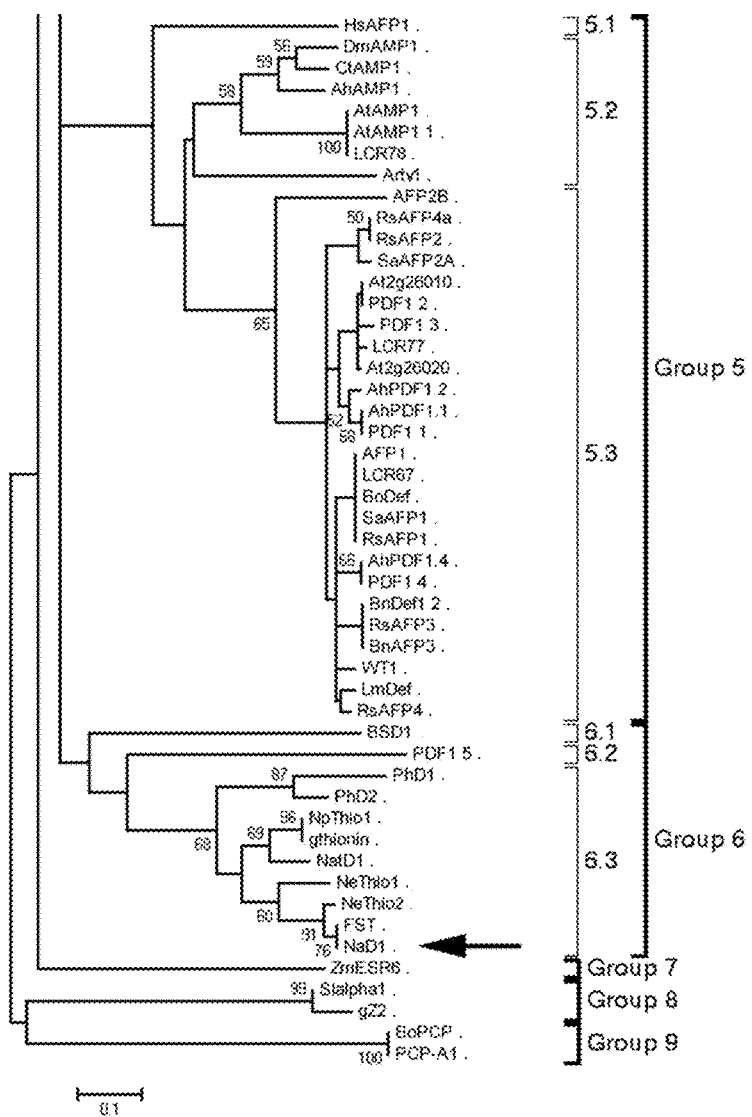

FIGS. 9A and 9B show a proposed classification of plant defensins. The neighbour-joining phylogenetic tree of plant defensin mature domains was constructed using MEGA 4.0. Bootstrap replicates greater than 50% are indicated. Defensins were separated into groups and subgroups (indicated on right) based on branch length. Branch scale=substitutions per residue. NaD1 is indicated by an arrow.

Figure 10:
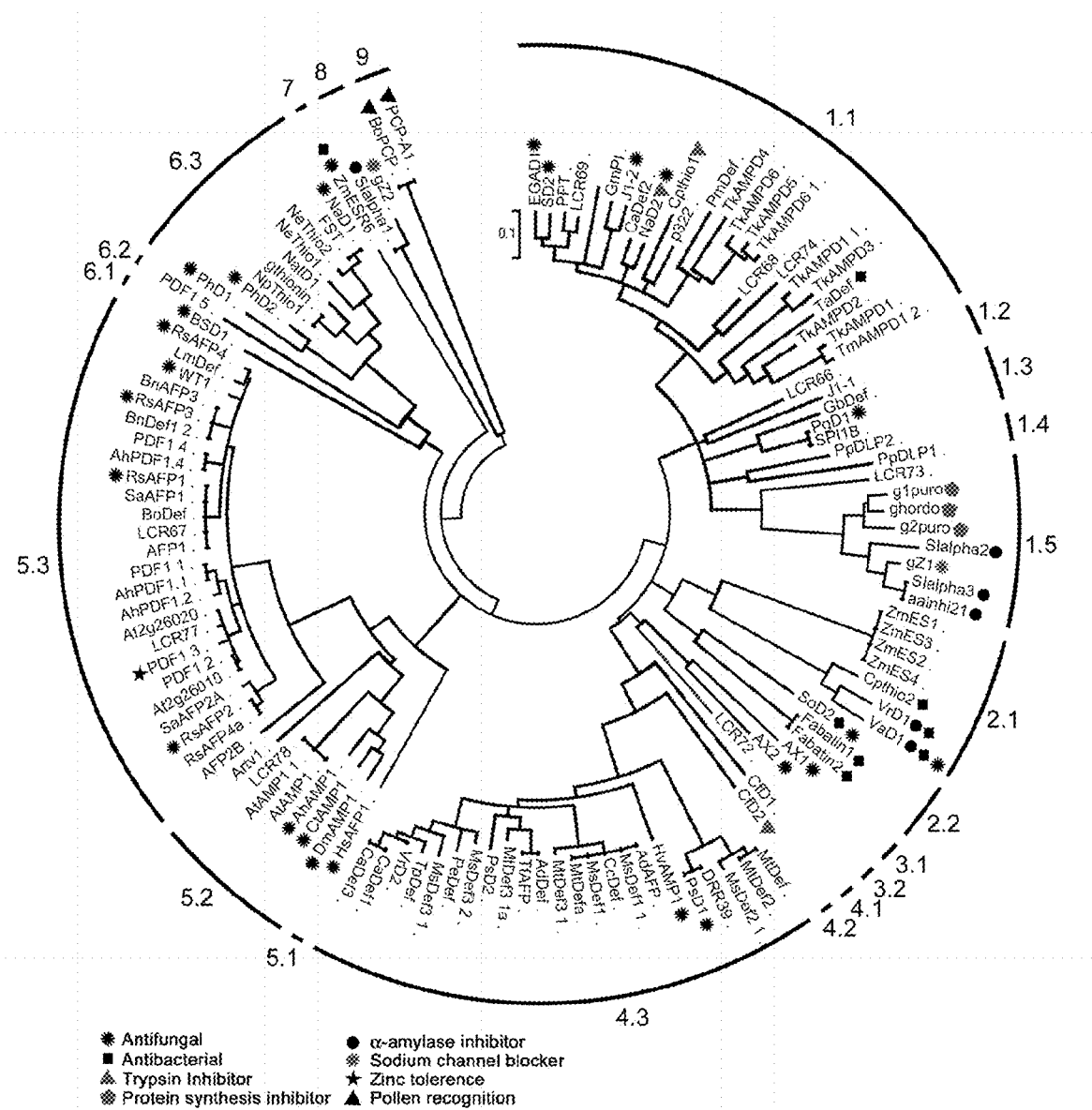

FIG. 10 shows a plant defensin phylogenetic tree indicating known functions of individual peptides. This is a circular view of the phylogenetic tree constructed in FIGS. 9A-9B. Branches representing different groups are indicated on the outer circle. Known functions of individual peptides are indicated by individual shapes (see legend).

DETAILED DESCRIPTION

Various terms are used according to their generally accepted meanings. For clarity, the following terms are further explained below.

Figure 1A:
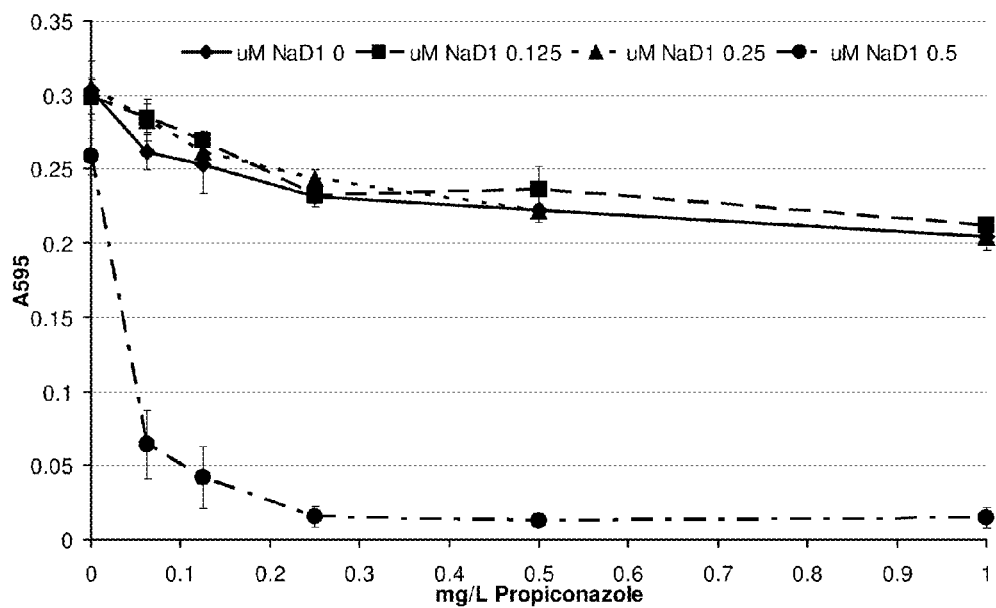
Figure 1B:
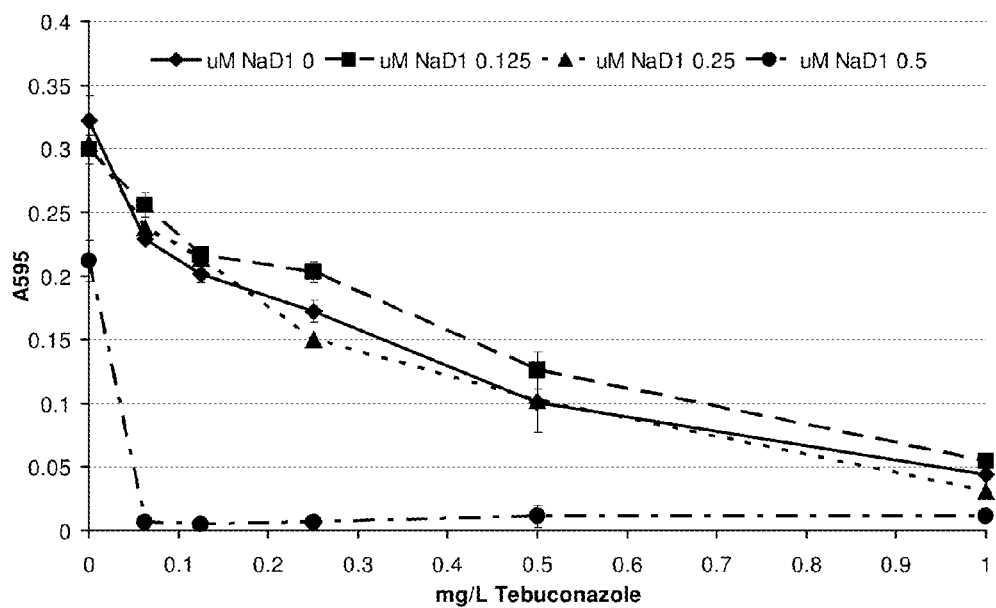
Figure 1C:
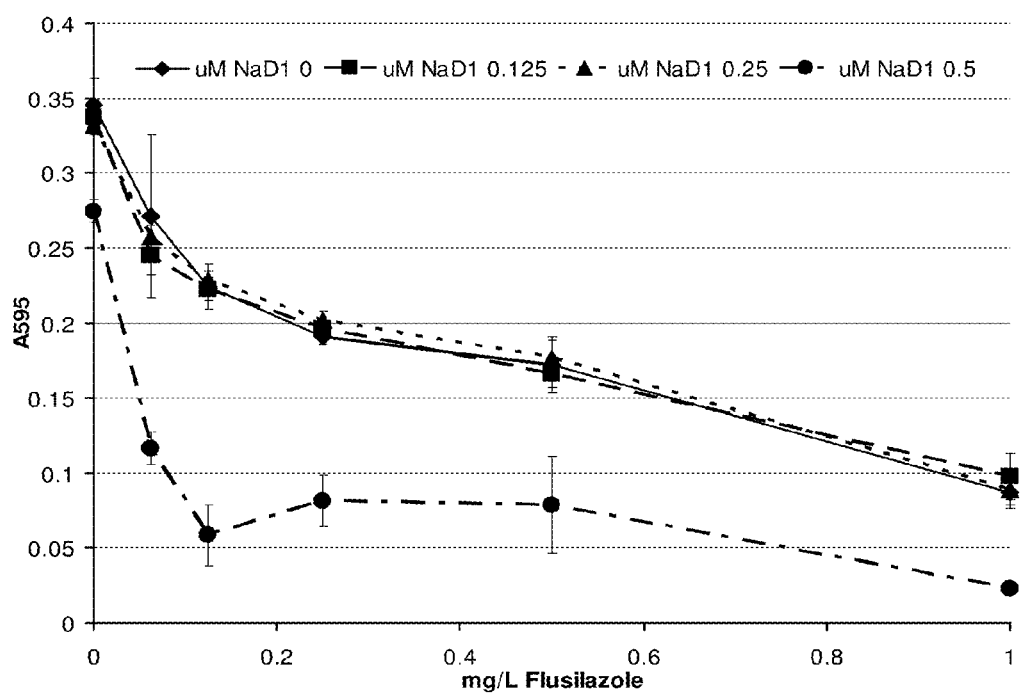
Figure 1D:
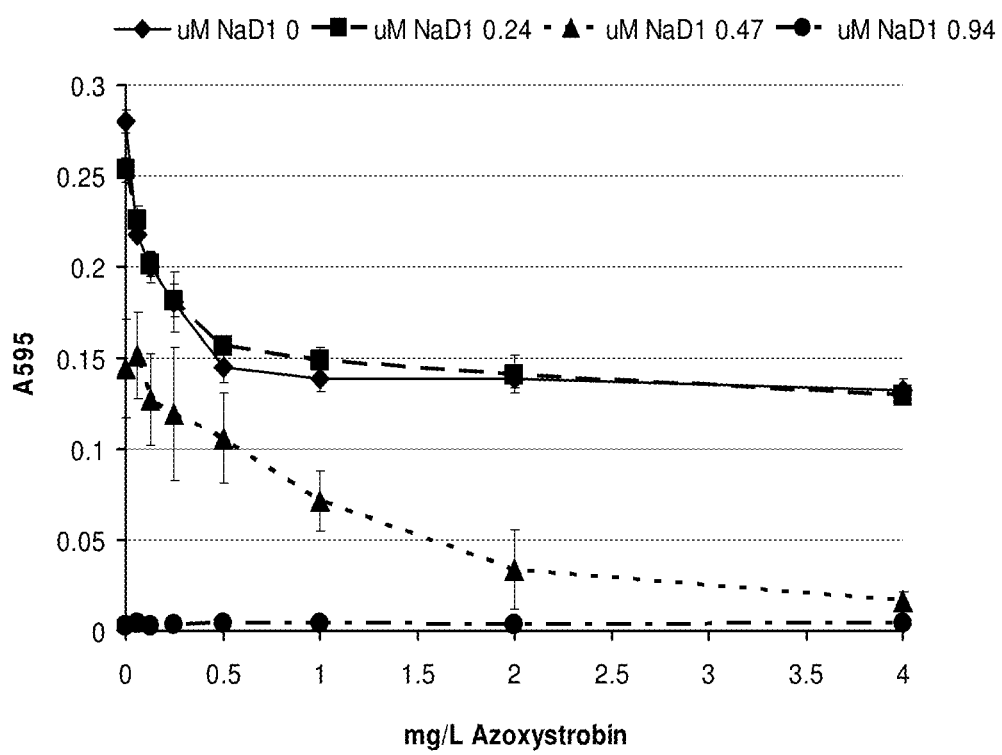
Figures 1E, 1F:
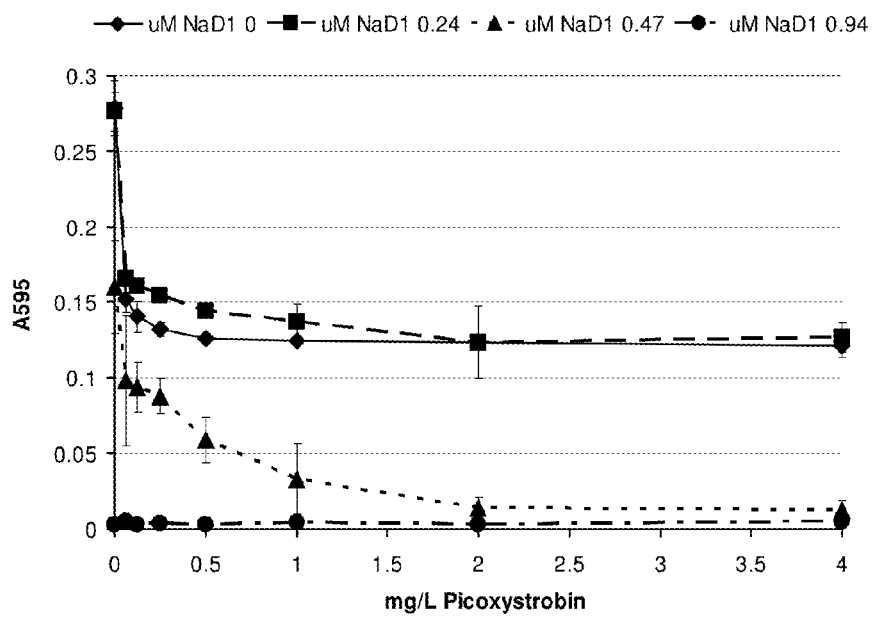
Figure 1G:
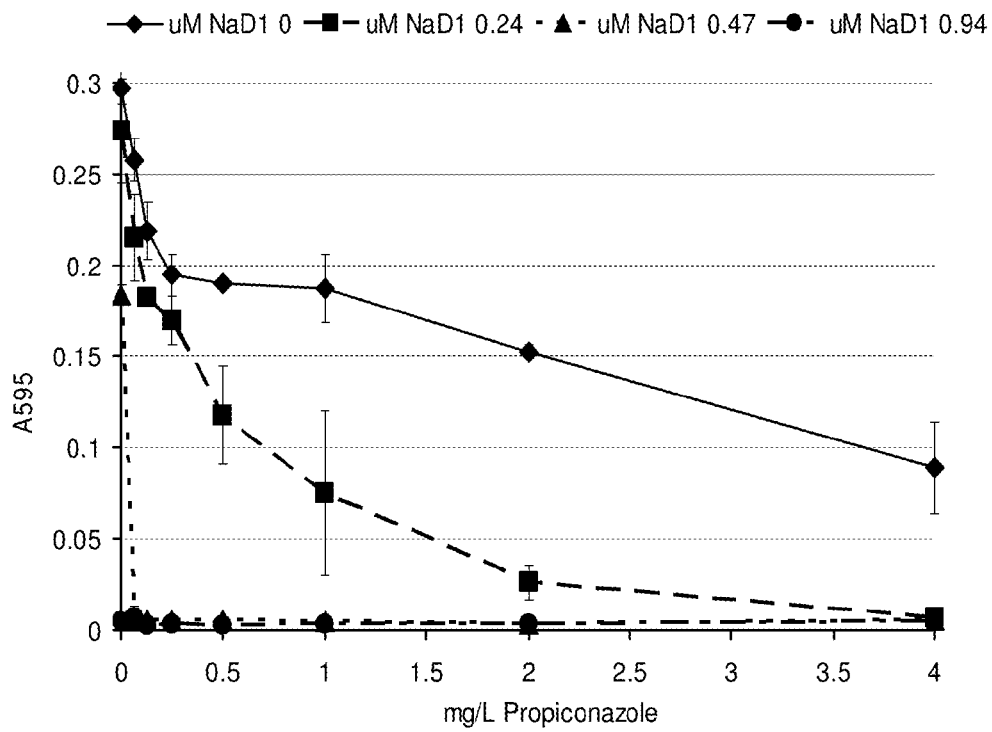
Figure 1H:
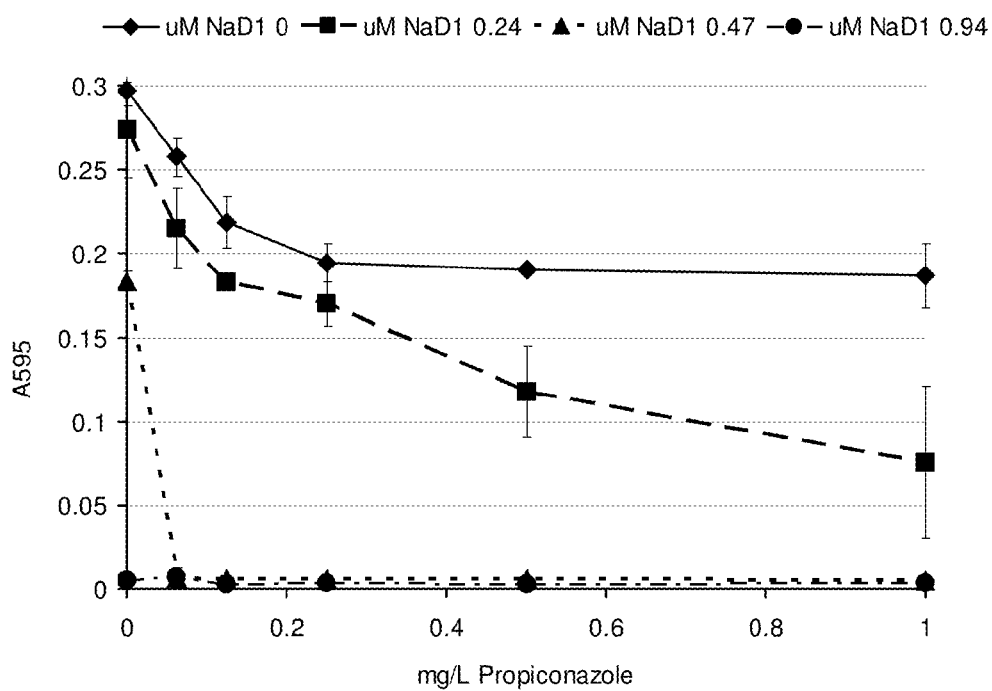

A "susceptible fungus" is a fungal strain that can be inhibited separately by each component of the invention or by a combination of both components. In some instances, inhibition by one of the components alone may not be detectable given the assay system employed, but will be found to contribute significantly to toxicity when combined with the other component. See, e.g. FIG. 1G, when toxicity of 0.24 µM NaD1 with *Fusarium graminearum* is very low in the absence of fungicide, but which is significantly enhanced when combined with 1 mg/L propiconazole. The foregoing example also demonstrates the synergy observable when a defensin and fungicide are applied in combination. Any fungal strain that can be inhibited by NaD1, for example, can be a susceptible fungus if that fungus can also be inhibited by a strobilurin, a triazole, or other fungicide. NaD1 has been shown to inhibit growth of a representative array of filamentous fungi, including but not limited to *Fusarium oxysporum* f. sp. *vasinfectum* (Fov), *Fusarium graminearum, Fusarium oxysporum* f. sp. *dianthi, Fusarium oxysporum* f. sp. *lycopersici, Fusarium solani, Fusarium pseudograminearum, Cochliobolus heterostrophus, Alternaria brassicola* and *Gaeumannomyces graminis* var. *tritici, Thielaviopsis basicola, Verticillium dahliae, Aspergillus nidulans, Sclerotinia sclerotiorum, Botrytis cinerea* and *Leptosphaeria maculans*. Related defensins have been shown to be active in inhibiting *F. graminearum*, including preferably floral defensins, for example without limitation NaD4, Tomdef2 and Tomdef3. Accordingly, a large number of synergistic combinations of plant defensins and chemical fungicides are available for plant protection against many fungal diseases, especially those caused by filamentous fungi.

In some instances, the inhibitory effect of a given fungicide or defensin may be below the limit of detection for a given assay, under the test conditions employed. Greco et al, 1995 has defined different categories of synergy, according to whether one, both or neither of the two components has measurable activity when assayed in the absence of the other component. The definition adopted herein includes all such situations provided that the combined effect of the two components acting together is capable of being greater than the sum of the individual components acting alone. It will be understood that a synergistic combination of two or more components may yield greater than additive activity only under certain conditions, e.g., when one or more of the components is present at a lower concentration than is maximal for individual efficacy. A combination of components is deemed synergistic, as the term is intended herein, if there exists a set of conditions, including but not limited to concentrations, where the combined effect of the components acting together is greater than the sum of the individual components acting alone. In an embodiment there is a system for protecting crop plants from fungal disease, comprising a first component and a second component, each of said first and second components being an inhibitor of a given susceptible fungus, the combination being synergistic. Richer (1987) has described quantitative approaches for demonstrating and evaluating synergy. Described therein is Limpel's formula for comparing an observed level of inhibition (lo) in the combined presence of two inhibitory components, X and Y, with an expected additive effect (Ee) resulting from each of X or Y acting separately at the same respective concentrations as used to measure their combined effect. Additive percent inhibition, Ee, is calculated as X+Y−XY/100 where X and Y are expressed as percent inhibition. Synergism exists where lo>Ee. Values of Ee and lo have been calculated from data disclosed herein based on the foregoing expression. Alternative approaches can be used in certain circumstances, as described by Richer (1987). Limpel's formula has also been employed by Harman et al, U.S. Pat. No. 6,512,166, to demonstrate synergy.

Fungal inhibition includes both fungicidal and fungistatic activity, as measured by reduction of fungal growth (or loss of viability) compared to a control. Fungal growth can be measured by many different methods known in the art. A commonly used method of measuring growth of a filamentous fungus entails germinating spores in a suitable growth medium, incubating for a time sufficient to achieve measurable growth, and measuring increased optical density in the culture after a specified incubation time. The optical density is increased with increased growth. Typically, fungal growth is necessary for pathogenesis. Therefore inhibition of fungal growth provides a suitable indicator for protection from fungal disease, i.e., the greater the inhibition, the more effective the protection.

"Preventing infection", in the present context, means that the plants treated with the system of the present invention avoid pathogen infection or disease symptoms or both, or exhibit reduced or minimized or less frequent pathogen infection or disease symptoms or both, that are the natural outcome of the plant-pathogen interactions when compared to plants neither treated with the chemical fungicide nor expressing the defensin transgene or treated with the defensin. That is to say, pathogenic fungi are prevented or reduced from causing disease and/or the associated disease symptoms. Infection and/or symptoms are reduced at least about 10%, 20%, 30%, 40%, 50, 60%, 70% or 80% or greater as compared to a plant not so treated with the system taught herein. In an alternative scenario, the system of the present invention results in reduced sporulation of the plant pathogenic fungus which is sensitive to both the chemical fungicide and the defensin, thus reducing the reproduction of the fungus and spread of disease.

Plant protection (disease resistance or reduction) can be evaluated by methods known in the art. See, Potter et al, (1993); Gorlach et al, (1996); Alexander et al, (1993). The skilled artisan will recognize that methods for determining plant infection and disease by a plant pathogen depends on the pathogen and plant being tested.

The term "plant defensin" has been well-defined in the literature (see, e.g. Lay and Anderson (2005)). The plant defensins are small, cysteine-rich proteins having typically 45-54 amino acids. The cysteine residues form a characteristic, definitive pattern of disulfide bonds. NaD1 is a plant defensin isolated from floral tissue of Nicotiana alata. The amino acid and coding sequences of NaD1 are disclosed in U.S. Pat. No. 7,041,877, which is incorporated by reference herein. Other antifungal defensins are well known to the art, including, but not limited to, RsAFP1 and RsAFP2 from radish, Ah-AMP4 from Aesculus hippocatanum, and AlfAFP from alfalfa, pI39 and pI230 from pea, and DmAMP1 from dahlia as well as ZmESR6, PhD2, PhD1, BSD1, RsAFP4, WT1, RsFP3, AhAMP1, CtAMP1, HsAFP1, HvAMP1, PsD1, AX2, AX1, SoD2, VaD1, gD1, NaD2, J1-2, SD2 and EGAD1, and preferably floral defensins such as NaD1 and NaD4 from Nicotiana alata and Tomdef2 and Tomdef3 from Lycopersicum cerasiforme. Functions of domains of plant defensins are discussed in U.S. patent application Ser. No. 12/105,956, filed Apr. 18, 2008, and incorporated by reference herein. The C-terminal tail of NaD1 or another defensin having a C-terminal tail, can be incorporated via recombinant DNA technology into the structure of other defensins so as to reduce (potential) toxicity to the plant expressing the transgene. In addition, the C-terminal tail of another defensin or a vacuolar targeting sequence from another plant protein can be substituted for that of NaD1.

The term "chemical fungicide" is used herein to include inorganic and organic chemical compounds used as fungicides to protect plants from fungus disease. Many useful fungicides are set forth above.

A synergistic effect occurs where two or more components produce a combined result that is greater than the sum of the individual results of each component acting alone. As described herein, synergistic fungal growth inhibition measured in the combined presence of at least one plant defensin and at least one chemical fungicide is greater than the summed inhibition measured in the presence of each component, defensin and fungicide, individually, under otherwise identical conditions. It will be understood that it is not necessary that a greater than additive effect be observed with every combination of concentrations of the two components in order to be deemed synergistic. The synergistic effect of two components can be observed under certain concentration combinations, but not in others. For example, if entry into the cell limits fungicide activity, the presence of defensin can result in synergy, especially if the concentration of fungicide applied alone is sub-maximal with respect to inhibition. By the same token, synergy can be masked if one or both components is present at such a high level as to result in maximum observable inhibition. The general system for a defensin fungicide combination is therefore termed "synergistic" because the potential for synergy exists even if synergy is not observed under all conditions. The synergy between a plant defensin and a chemical fungicide provides greater fungal inhibition than can be obtained by either component acting alone, for at least some dosages. In some cases a fungicide that is not measurably effective against a particular pathogen becomes effective in the presence of defensin. Therefore, this invention provides for increased protection of plants from fungal disease with reduced dependence on chemical fungicide. The advantages include decreased input cost to growers, a broader spectrum of activity against plant pathogens and reduced potential for environmental damage. In addition, the selection pressure for development of fungicide-resistant fungal strains is greatly reduced, which allows for an extended commercial life as well as reduced proliferation of resistant fungal strains and reduced likelihood of emergence of multiple-resistant strains.

Methods for using the system of the present invention can be adapted to individual combinations of plant to be protected and fungal strain(s) to be inhibited, as well understood in the art. The mechanism of infection of the fungus, the part or parts of the plant that are susceptible to fungal attack, and the growth stage of the plant when fungal disease is likely to occur, are important factors to be considered. For example, if leaves of a mature plant or fruits are the main loci of fungal growth, application of fungicide as a foliar (surface) spray can be the preferred means of delivery of the chemical fungicide. In the case of fungal disease in cotton caused by Fov, the most significant damage occurs in young seedlings. In that instance, the fungicide component is preferably incorporated into the soil or other growth medium, coated on seeds or sprayed on emergent seedlings. From contacting of the plant with a chemical fungicide, there may be systemic transport of the fungicide throughout the plant.

Effective rates of application of the fungicidal composition can be influenced by many factors, including the environment and should be determined under actual use conditions. Preferably, the rate of application is from about 0.1 lb per acre to about 10 lb per acre of chemical fungicide. The fungicide of interest can be applied to the plants to be protected or treated in the form of a composition with carriers, surfactants, adjuvants or other application-promoting chemicals customarily employed in formulation technology. Suitable carriers, surfactants and the like can be solid or liquid and are the substances ordinarily employed in formulation technology, for example, natural or regenerated mineral substances, solvents, dispersants, wetting agents, tackifiers, thickeners, binders and/or fertilizers.

The fungicidal composition can be applied to the above-ground parts of the plants to be protected from fungal attack, especially to the leaves (foliar application). The frequency and the rate of application depend on the biological and climatic conditions of the pathogen. The compositions can also penetrate the plants through the roots via the soil or via the water (systemic action) if the locus of the plant is impregnated with a liquid formulation or one which dissolves in water (rice culture, for example) or if the composition are introduced in solid form into the soil, for example, in the form of granules (soil application). In order to treat seed, the compositions can be applied to tubers or seeds (coating) either by impregnating the tubers or seeds by impregnating with a liquid formulation or by coating with a combined wet or dry formulation. Other strategies for applications are also well known to the art.

In one aspect of the present invention, a system is provided for the protection of a plant from fungal disease, and that prevention or treatment results in decreased need for fungicide treatment of plants or plant parts, thus lowering costs of material, labor, and environmental pollution, or prolonging shelf-life of products (e.g. fruit, seed, and the like) of such plants. The term "plant" includes whole plants and parts thereof, including, but not limited to, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. The plants that can be protected using the system of the invention include higher and lower plants, including angiosperms (monocotyledonous and dicotyledonous plants), gymnosperms, ferns, horsetails, psilophytes, lycophytes, bryophytes, and multicellular algae. Plants for use in the system of the present invention can include any vascular plant, for example monocotyledons or dicotyledons or gymnosperms, including, but not limited to, alfalfa, apple, *Arabidopsis*, banana, barley, canola, castor bean, *chrysanthemum*, clover, cocoa, coffee, cotton, cottonseed, corn (maize), *crambe*, cranberry, cucumber, dendrobium, dio-scorea, *eucalyptus*, fescue, flax, *gladiolus*, liliacea, linseed, millet, muskmelon, mustard, oat, oil palm, oilseed rape, *papaya*, peanut, pineapple, ornamental plants, *Phaseolus*, potato, rapeseed, rice, rye, ryegrass, safflower, sesame, *sorghum*, soybean, sugarbeet, sugarcane, sunflower, strawberry, tobacco, tomato, turfgrass, wheat and vegetable crops such as lettuce, celery, broccoli, cauliflower, cucurbits, onions (including garlic, shallots, leeks, and chives); fruit and nut trees, such as apple, pear, peach, orange, grapefruit, lemon, lime, almond, pecan, walnut, hazelnut; vines, such as grapes, kiwi, hops; fruit shrubs and brambles, such as raspberry, blackberry, gooseberry; forest trees, such as ash, pine, fir, maple, oak, chestnut, popular; with alfalfa, canola, castor bean, corn, cotton, *crambe*, flax, linseed, mustard, oil palm, oilseed rape, peanut, potato, rice, safflower, sesame, soybean, sugarbeet, sunflower, tobacco, tomato, and wheat preferred. More particularly, plants for use in the methods of the present invention include any crop plant, for example, forage crop, oilseed crop, grain crop, fruit crop, vegetable crop, fiber crop, spice crop, nut crop, turf crop, sugar crop, beverage crop, and forest crop. The crop plant can be soybean, wheat, corn, cotton, alfalfa, sugarbeet, rice, potato, tomato, onion, a legume, or a pea plant.

A "transgenic plant" refers to a plant, or seed thereof, that contains genetic material not found (i.e. "exogenous") in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of the polypeptide. The expression cassette can be introduced into a plant by transformation or by breeding after transformation of a parent plant. The term transgenic plant encompasses progeny plants (and seeds) containing the expression vector or cassette.

The plant or plant part for use in the present system includes plants at any stage of plant development. Preferably, the application occurs during the stages of germination, seedling growth, vegetative growth, and reproductive growth. More preferably, applications of the present invention occur during vegetative and reproductive growth stages. The stages of vegetative and reproductive growth are also referred to herein as "adult" or "mature" plants.

While the present disclosure provides a system for protecting plants from fungal infection using a chemical fungicide and an antifungal defensin and the synergistic action thereof, it is understood that additional materials can be added to the applied composition to achieve even more benefit with respect to the health of the plant, for example, by incorporating an insecticidal or a nematicidal compound, or by utilizing more than one defensin and/or more than one chemical fungicide.

The defensin component is preferably supplied by the plant that is to be protected, although surface sprays or seed coatings can be utilized in certain instances. In certain embodiments, the plant is genetically modified to express the desired defensin using methods well-known in the art. In the example of cotton to be protected from disease caused by Fov, a cotton variety normally susceptible to Fov infection has been genetically transformed to express the defensin NaD1. The transgenic cotton variety expressing NaD1 has been shown to be significantly protected from the pathological effects of Fov infection in field trials, compared to the untransformed parent variety (U.S. application Ser. No. 12/105,956, filed Apr. 18, 2008, incorporated herein by reference to the extent there is no inconsistency with the present disclosure). The results establish that Fov is susceptible to NaD1 and that the amount of a defensin, such as NaD1, that can be expressed by transgenic plants is sufficient to contribute to a synergistic effect when combined with application of a chemical fungicide as described herein.

Purified defensin protein can, if desired, be directly combined with chemical fungicide as a mixture, provided they can be formulated together or sequentially by separate application means. In a further embodiment, defensin can be provided by transgenic "nurse" plants grown alongside the plants to be protected.

Membrane permeabilization has been reported for some plant defensins, although the mechanism of permeabilization has not been investigated. In the case of the plant defensins RsAFP2 and DmAMP1, permeabilization is believed to involve a specific receptor on the cell surface. The presence of specific sphingolipids in the plasma membrane are also required for the activity of these defensins, possibly as binding sites (Thevissen et al, 2000a, b; Thevissen et al, 2004; Thevissen et al, 2005).

NaD1 was tested in vitro for antifungal activity against the filamentous fungi *Fusarium oxysporum* (Fov), *Verticillium dahliae, Thielaviopsis basicola, Aspergillus nidulans* and *Leptosphaeria maculans*. At 1 µM, NaD1 retarded the growth of Fov and *L. maculans* by 50% while *V. dahliae, T. basicola,* and *A. nidulans* were all inhibited by approximately 65%. At 5 µM NaD1, the growth of all five species was inhibited by more than 80%. These five fungal species are all members of the ascomycete phylum and are distributed among three classes in the subphylum pezizomycotiria. These fungi are agronomically important fungal pathogens. All filamentous fungi tested thus far are sensitive to inhibition by NaD1. Antifungal activity against *F. graminearum* was demonstrated herein for NaD4, tomdef2 and Tomdef3.

Under the conditions tested, NaD1 had no effect on the growth of the yeasts *Saccharomyces cerevisiae, Candida albicans* and *Pichia pastoris*, or the Gram-negative and Gram-positive bacterial strains tested. The effect of NaD1 on yeast was repeated under the same conditions wherein the plant defensins RsAFP2 and DmAMP1 inhibited the growth of *C. albicans* and *S. cerevisiae* respectively. Even under these conditions, NaD1 did not inhibit the growth of any yeasts of the phylum Ascomycetes, subphylum Saccharomycetes. In addition, NaD1 was not toxic to human HeLa cells or to *Spodoptera frugiperda* Sf-21 insect cells.

TABLE 1

Growth inhibitory effects of NaD1 on various cell types

| Cell type | NaD1 $IC_{50}$ (µM) |
|---|---|
| *Fusarium oxysporum* f. sp. *vasinfectum* | 1.0 |
| *Leptosphaeria maculans* | 0.80 |
| *Aspergillus nidulans* | 0.80 |
| *Verticillium dahliae* | 0.75 |
| *Thielaviopsis basicola* | 0.80 |
| *Candida albicans* | >10 |
| *Saccharomyces cerevisiae* | >10 |
| *Pichia pastoris* | >10 |
| *Staphylococcus aureus* | >10 |
| *Bacillus cereus* | >10 |
| *Escherichia coli* | >10 |
| *Pseudomonas aeruginosa* | >10 |
| HeLa cells | >10 |
| *Spodoptera frugiperda* (Sf21) | >10 |

The importance of the four disulfide bonds in NaD1 was investigated by reducing and alkylating the cysteine residues. Reduced and alkylated NaD1 ($NaD1_{R\&A}$) was completely inactive in the growth inhibitory assays with Fov, even at a concentration ten-fold higher than the $IC_{50}$ for NaD1.

The activities of many antimicrobial peptides are attenuated by the presence of cations, particularly divalent cations, in the media; therefore the effect of NaD1 (10 µM) on the growth of Fov was measured in the presence of the divalent cations $Ca^{2+}$ and $Mg^{2+}$ to determine their effect on NaD1 activity. Both cations decreased the antifungal activity of NaD1 in a concentration-dependent manner. Complete inactivation of NaD1 was observed at <2 mM $CaCl_2$, whereas 50 mM $MgCl_2$ was required to achieve the same effect, indicating that $Ca^{2+}$ was greater than 20 times more antagonistic. This indicates the effect is not simply related to charge and that blocking of specific interactions may be involved. By contrast, the activity of the tobacco protein osmotin is enhanced by the presence of $Ca^{2+}$, presumably by facilitating an interaction with phosphomannans on the fungal cell surface (Salzman et al, 2004).

Osmotin is a member of the thaumatin-like ("TL") family of antifungal proteins. The structures of several of these ~22 kDa proteins have been solved. They consist of a conserved fold with three domains; Domain I is an eleven strand flattened β-sandwich that forms the core of the molecule, from which a number of disulphide loops extend (Domains II and III) (de Vos et al, 1985). Thus the size and structure of osmotins is very different to the defensins.

Osmotin is known to permeabilize the membranes of susceptible fungi (Abad et al, 1996). It is unlikely that this permeabilization results from direct interaction of the protein with the membrane because TL proteins do not exhibit any of the structural characteristics of membrane permeabilizing peptides.

The relatively large size of osmotin (~22 kDa) compared to defensins (~4.7 kDa) suggests that access of osmotin to the fungal membrane is restricted by the glucan and chitin polysaccharides in the fungal cell wall. Thus, U.S. Pat. No. 6,512,166 teaches that "fungal cell wall degrading chitinolytic or glucanolytic enzymes enhance the antifungal activity of osmotin".

In contrast, defensins have ready access to the membranes in fungal hyphae and thus treatment with glucanolytic enzymes does not enhance the antifungal activity of defensins.

Another embodiment of the invention is a method for identifying a defensin which enhances antifungal activity of a chemical fungicide, without the need to carry out antifungal activity assays. The method entails measuring the ability of a defensin to permit entry into a fungal cell of a permeability indicator compound. A suitable permeabilization indicator compound is one whose location, whether intracellular or extracellular, can be detected. Under normal conditions, the indicator compound remains extracellular and does not freely pass through the cell wall and membrane. In the presence of certain defensins, such as NaD1, NaD4, Tomdef2 and Tomdef3, the indicator compound can be detected inside the cell of a given fungus. If a defensin being tested (a test defensin) is found to increase permeability of a given fungus by increasing the intracellular amount of the indicator compound, when present with the fungus, that defensin is thereby identified as one that enhances antifungal activity of a chemical fungicide, when the defensin and fungicide are combined in the presence of the fungus, as shown in Example 8.

A standard criterion for a permeability indicator compound suitable for use in the invention is provided by the use of SYTOX® (Registered Trademark) green (Invitrogen Corp. Carlsbad, Calif., USA) as an indicator for increased fungal cell permeability observed in the presence of NaD1, as described below. The method of identifying a defensin that enhances chemical fungicide efficacy is not limited to the use of SYTOX® green, but can be carried out with any use of any permeability indicator compound that yields similar permeability data when tested with NaD1. A relative permeability index (RPI) is herein defined wherein the degree of permeabilization of a fungal strain induced by a defined concentration of a given defensin is addressed, relative to a value of 1.0 for NaD1 at the same concentration. See Example 8 and FIG. 8N.

The described method is carried out using methods described below, or with adaptations that would be understood by one skilled in the art as being equivalent. The steps of the method include: combining a fungus with a permeability indicator compound in the presence of, and separately, as a control, in the absence of, a test defensin; then comparing any detectable intracellular amounts of the permeability indicator compound in the fungus in the presence and in the absence of the test defensin. If the effect of presence of the test defensin is such that an increased amount of intracellular indicator compound is detected in the fungus, compared to the control, the test defensin is identified as one which can enhance the efficacy of a chemical fungicide when the defensin and the fungicide are combined in the presence of the fungus. A plant defensin identified by the method just described will be understood to be useful as a defensin component of the system for protecting a plant from fungus disease as disclosed herein, whether or not the defensin is known to have anti-fungal activity.

Permeabilization of Fov hyphal membranes by NaD1 was measured using the fluorescent dye SYTOX® green. SYTOX® green fluorescence increases more than 1000 fold upon binding to nucleic acids, but the dye only enters cells when the plasma membrane is compromised. Hyphae were treated with 0.1, 2 or 10 µM NaD1 or 10 µM NaD1$_{R\&A}$ (reduced and alkylated) in the presence of SYTOX® green. NaD1 permeabilized hyphae, and this permeabilization correlated with growth inhibition, except at the lowest concentration of NaD1 (0.1 µM) where a small amount of SYTOX® green uptake occurred, but no growth inhibition was observed. Permeabilization was not observed in hyphae treated with NaD1$_{R\&A}$, nor with untreated hyphae, consistent with the lack of growth inhibition.

At a very low, non-inhibitory concentration of NaD1 (0.1 µM), SYTOX® green entered some, but not all hyphae, reflecting NaD1-mediated permeabilization. The nuclei of the hyphal cells that had taken up SYTOX® green appeared intact, and the cytoplasm appeared unaltered. At higher, inhibitory concentrations of NaD1, the SYTOX® green entered most hyphae and formed a diffuse pattern of fluorescence across the cell. The nuclei were no longer intact, and the cytoplasm of all permeabilized hyphae appeared granular after NaD1 treatment.

To determine whether NaD1 formed an opening of a distinct size or merely destabilized the plasma membrane, NaD1-treated hyphae were incubated with FITC-labeled dextrans (Sigma-Aldrich) of either 4 kDa (average globular diameter of 14 Å) or 10 kDa (average globular diameter of 23 Å). FITC-dextrans of 4 kDa entered hyphae at the same NaD1 concentration that led to SYTOX green uptake (MW ~650 Da), while 10 kDa FITC-dextrans were excluded even at very high concentrations of NaD1. To examine whether the opening formed by NaD1 was transient or relatively stable, the assay was conducted in two ways. FITC-dextrans were either added at the same time as NaD1 or after removal of unbound NaD1 by extensive washing. The 4 kDa FITC-dextran was able to enter under both conditions.

NaD1 permeabilized the plasma membrane of susceptible hyphae in a dose-dependent manner that correlated with growth inhibition; however, at non-inhibitory concentrations of NaD1, some permeabilization was still detected. At these low concentrations, the cytoplasm of permeabilized hyphae appeared normal under the light microscope and SYTOX® green was localized to the nuclei. At higher, inhibitory concentrations of NaD1, permeabilized hyphae exhibited significant cytoplasmic granulation and the SYTOX® green fluorescence pattern was much more diffuse across the cell indicating that the nuclei were no longer intact. Without wishing to be bound by theory, it is believed that NaD1-induced permeabilization of fungal membranes is required for growth inhibition, although it may not be sufficient to induce cell death.

The fluidity of the fatty-acyl chains of membrane lipids decreases as the temperature decreases, leading to an overall increase in membrane stability. It is postulated that this makes insertion of peptides into bilayers more difficult, thus decreasing the amount of peptide-induced permeabilization that occurs through direct lipid interaction. This led to an assessment of the effect of temperature on NaD1-induced permeabilization. At 10° C. NaD1 induced substantial uptake of SYTOX® green, although this was less that that observed at 25° C. At 4° C., only a small degree of permeabilization could be seen and this was reduced even further at 0° C.

Without intending to be bound by any theory or mechanism of operation, it is postulated that NaD1 appears to act through either barrel-stave or toroidal pore formation. The consistency of uptake of the 4 kDa but not the 10 kDa dextrans over a number of NaD1 concentrations differs from other pore-forming antimicrobial peptides such as melittin, which cause a concentration-dependent increase in the size of dextrans that are released from artificial liposomes (Ladokhin et al, 1997), indicating an increase in pore size. The predicted size of the NaD1 pore is large enough to allow NaD1 itself to pass through into the cell.

The rate of permeabilization of Fov hyphae by various concentrations of NaD1 was monitored by measuring SYTOX® green uptake over time. At all concentrations, permeabilization was only observed after a lag time of around 20 min, and fluorescence began to plateau after 90 min. The rate of permeabilization was partially concentration-dependent, increasing progressively with NaD1 concentrations up to 3 µM. At concentrations above 3 µM (up to 50 µM), there was very little difference in the kinetics of permeabilization. This was reflected in the Vmax (maximum rate of fluorescence increase) data which show a steady state of uptake at low concentrations (below those required for significant growth inhibition), followed by a linear increase in fluorescence up to 6.25 µM NaD1. Above this concentration, the reaction rate did not change significantly, indicating the process is saturable.

The apparent loss of organelles after exposure to NaD1 indicated cells were undergoing cell death. To examine this further, the production of reactive oxygen species (ROS) was investigated in hyphae treated with NaD1. The non-fluorescent molecule dihydrorhodamine 123 (DHR123) was pre-loaded into hyphae which were then treated with NaD1 (0.1, 2 and 10 µM) or 10 µM NaD1$_{R\&A}$. In the presence of ROS, DHR123 is oxidized to the fluorescent molecule rhodamine 123. A concentration-dependent increase in fluorescence was observed in Fov hyphae following exposure to NaD1 at concentrations of NaD1 sufficient for growth inhibition. No fluorescence was observed after treatment with NaD1$_{R\&A}$ consistent with its lack of antifungal activity.

Ascorbic acid and 2,2,6,6-tetramethylpiperidine-N-oxyl (TEMPO) (Sigma-Aldrich) are both potent, cell-permeant scavengers of ROS. To explore the relevance of NaD1-induced ROS production, DHR123 oxidation by NaD1 was monitored in the presence of these two molecules. The presence of ascorbic acid or TEMPO did not alter the level of fluorescence, nor did the presence of 10 mM ascorbic acid affect growth inhibition of Fov by NaD1.

In summary, NaD1 disrupts membranes, apparently via formation of a toroidal or barrel-stave pore that allows entry of molecules between 14 and 23 Å in diameter. NaD1 does not appear to interact with artificial bilayers, including those formed with lipids isolated from the hyphae of sensitive fungi, indicating that it may not interact directly with lipids, although the temperature dependence of toxicity supports the idea that it does insert into the membrane. The kinetics of SYTOX® green uptake suggest that a receptor is involved in membrane permeabilization.

Immunogold electron microscopy was used to determine whether NaD1 could cross the cell membrane and enter the cytoplasm of treated hyphae. Hyphae treated with or without NaD1 (10 µM) for 2 h were washed, fixed and sectioned for immunogold electron microscopy using the anti-NaD1 antibody. Many, but not all, of the NaD1-treated hyphae had granulated cytoplasm with a number of aberrant vacuoles. The cytoplasm in these hyphae was heavily labeled with the anti-NaD1 antibody, although the NaD1 was not associated with particular intracellular organelles. The granulated cytoplasm in the NaD1-treated hyphae appeared to have collapsed inward, away from the cell wall. Gold labeling was also observed on the cell walls. A small number of cells were identified where only part of the cytoplasm was granulated. Gold labeling was present in these hyphae but was heaviest in the granular portion. Hyphae with normal cytoplasm were also present in the sample. These hyphae only exhibited a small amount of cytoplasmic gold labeling, however, their cell walls were labeled. No significant labeling was observed on either granular or non-granular hyphae when the NaD1-treated sample was labeled with the pre-immune antibody. Water-treated hyphae contacted with the anti-NaD1 antibody also did not show any significant labeling.

To further confirm NaD1 uptake and to exclude the possibility that the presence of NaD1 in the cytoplasm was an artifact of the fixation process, NaD1 was labeled with the fluorophore bimane (Invitrogen-Molecular Probes). This fluorophore was chosen because of its small, uncharged nature and the ability to covalently attach the molecule to carboxyl residues on NaD1, leaving the loop regions unmodified. NaD1 labeled in this manner retained full antifungal activity. In contrast, NaD1 labeled with FITC via reactive amine groups was not biologically active, probably due to the fact that the molecule carries two negative charges at physiological pH. The attachment of a single FITC molecule to a reactive amine in NaD1 would thus reduce the overall charge of the protein by three. Since a positive charge is proposed to be vital for antimicrobial activity, NaD1 may not be able to tolerate this treatment. Furthermore, two of the lysines on NaD1 which would react with FITC are located on the loop regions that have been described as essential for the antifungal activity of another plant defensin, RsAFP2 (De Samblanx et al, 1997).

The amount of NaD1 taken up into the cytoplasm of Fov hyphae was also monitored by SDS-PAGE and immunoblotting of cytoplasmic contents. These data indicated that NaD1 uptake occurred after 20 min which is consistent with the microscopy. The amount of NaD1 in the Fov cytoplasm increased up until 60 min, after which time it decreased slightly. This may be a result of cell breakdown and subsequent release of some internalized NaD1 back into the supernatant.

Evidence is now mounting that a number of antimicrobial peptides are able to enter cells and their mechanism of action involves intracellular targets. The cytoplasm of the NaD1-treated hyphae appeared 'shrunken' and contracted away from the cell wall. A similar morphology was observed in *Aspergillus nidulans* hyphae treated with the antifungal protein, AFP, from *Aspergillus giganteus*. AFP is fungistatic at low concentrations, causes membrane permeabilization and binds to the cell wall; while at high concentrations the protein is internalized and causes granulation of the hyphal cytoplasm (Theis et al, 2003; Theis et al, 2004).

A number of hyphae that had not taken up large amounts of NaD1 were also present in the NaD1-treated sample. The cytoplasm of these hyphae was not granular, suggesting that NaD1 uptake is essential to the cell killing process. In support of this, hyphae could also be identified with partially granulated cytoplasm, and NaD1 was concentrated in these areas but not in the areas of the cell that appeared normal. This is believed to represent an early stage of cell death.

The absence of NaD1 from several hyphae at a concentration that was sufficient to cause >90% growth inhibition may give some information as to the mode of uptake of NaD1. The growth inhibition assays were started with spores, so NaD1 was present through all stages of the cell cycle. In contrast, the microscopy was performed on hyphae that were likely to be at different stages of the cell cycle. Since immunoblotting analysis revealed that NaD1 remained in the supernatant after 3 h, the lack of internalization of NaD1 by some hyphae is not due to an insufficient concentration being used. It is possible that NaD1 is not able to affect cells in certain stages of the cell cycle. This is consistent with observations for the insect antifungal peptide, tenecin 3, which is taken up into cells during logarithmic phase growth but not during stationary phase (Kim et al, 2001). Hyphae that do not take up NaD1 in the microscopy assays may represent those in a stage of growth that is resistant to NaD1. This could be explained by cell wall changes that occur upon entry into stationary phase that prevent peptide uptake (Klis et al, 2002). It is noted that the antimicrobial peptide cecropin, which is able to inhibit the growth of germinating but not non-germinating *Aspergillus* hyphae, only binds to the cell surface of germinating hyphae (Ekengren and Hultmark, 1999).

NaD1-bimane was added to live hyphae, and uptake was monitored by fluorescence microscopy. Internalization was observed after 20-30 min, which is consistent with the SYTOX® green permeabilization kinetics. At this time point the hyphae that had taken up NaD1 still looked healthy, however, over time, the cytoplasm of these hyphae became granular and they appeared to die. NaD1 did not appear to interact with specific organelles upon uptake but rather demonstrated a cytoplasmic localization. This differs from the plant defensin Psd1, which is transported to the nucleus of treated *N. crassa* cells (Lobo et al, 2007). Interaction of Psd1 with a nuclear-located cell-cycle protein has been validated, and its antifungal activity is believed to be a result of cell-cycle arrest (Lobo et al, 2007). The antifungal protein from *P. chrysogenum*, PAF, on the other hand, displays cytoplasmic localization upon entry into *A. nidulans* hyphae (Oberparleiter et al, 2003). After entry, PAF induces an apoptotic phenotype, probably through G-protein signaling (Leiter et al, 2005).

As mentioned above, plant defensins form a large family of peptides that have a conserved scaffold but little sequence conservation, particularly in the solvent-exposed loops. Not all defensins have antifungal activity; defensins with antibacterial, enzyme inhibitory and protein synthesis inhibitory activities have also been identified.

The recent discovery of a large number of plant defensins and the increase in the number of these that are functionally characterized has made it clear that the classification groups proposed for defensins over 10 years ago are no longer appropriate. A phylogenetic tree of 126 plant defensin sequences was constructed and based on this, a new grouping system was proposed. In total, nine major groups (groups 1-9) were defined based on branch points from the tree. Within these groups a number of subgroups were also proposed. In some instances, defensins from a single plant species were clustered together while in other cases they were found in different regions of the tree. Functional analysis of these groups revealed that defensins which clustered displayed similar activities, while those that separated did not. This demonstrates that phylogenetic (bioinformatic) analysis may prove a useful tool for the prediction of functions of novel defensins.

In order to carry out neighbour-joining phylogenetic analysis, sequences of known defensins were downloaded from the U.S. National Library of Medicine's National Center for Biotechnology Information (NCBI) protein database using the search string 'plant defensin'. Other sequences identified in the literature but not available in the database were also added manually. A complete list of peptides including their source and accession number is provided in Table 2. A TCOFFEE (Tree based Consistency Objective Function For AlignmEnt Evaluation) (Poirot et al, 2003) alignment was performed on the mature defensin domain sequences for 126 proteins and the resulting alignment file was used to generate a neighbour-joining phylogenetic tree using MEGA-4 (Tamura et al, 2007). The integrity of the tree was estimated by 1000 bootstrap replicates with bootstrap values of above 50% indicated at individual nodes.

A neighbour-joining phylogenetic tree of aligned mature domains of 126 plant defensins is presented in FIG. 9. Based on this analysis, a new classification system that is composed of nine major groups (Groups 1-9, see below) is proposed. Group 1 was separated into five sub-groups based on branch length (in units of amino acid substitutions per residue). Groups 2 and 3 were both separated into two subgroups and groups 4, 5 and 6 were separated into three subgroups. This classification does not contradict the previously proposed groupings, except to separate HsAFP1 into a separate subgroup. This suggests classification based on both function and sequence may be complementary. In some instances (e.g. *R. sativus* and *T. kiharae*), defensins from a single plant species group together in the tree, while in others, they are separated throughout the tree (*Arabidopsis, N. alata, V. radiata*).

TABLE 2

Source and accession numbers of plant defensins used to construct phylogenetic tree

| Peptide | Source | Accession number |
|---|---|---|
| Part 1 | | |
| aainhi21 | Sorghum bicolor | Q09198 |
| AdAFP | Arachis diogoi | AAO72633 |
| AdDef | Arachis diogoi | AAP92330 |
| AFP1 | Arabidopsis thaliana | P30224 |
| AFP2B | Sinapis alba | Q10989 |
| AhAMP1 | Aesculus hippocastanum | AAB34970 |
| AhPDF1.1 | Arabidopsis halleri | AAY27736 |
| AhPDF1.2 | Arabidopsis halleri | AAY27737 |
| AhPDF1.4 | Arabidopsis halleri | AAY27739 |
| Artv1 | Artemisia vulgaris | Q84ZX5 |
| At2g26010 | Arabidopsis thaliana | O80995 |
| At2g26020 | Arabidopsis thaliana | O80994 |
| AtAFP | Arabidopsis thaliana | P30224 |
| AtAMP1 | Arabidopsis thaliana | AAM45086 |
| AtAMP1.1 | Arabidopsis thaliana | AAL36289 |
| AX1 | Beta vulgaris | P81493 |
| AX2 | Beta vulgaris | P82010 |
| BnAFP | Brassica napus | Q39313 |
| BnDef1.2 | Brassica napus | AAX35338 |
| BoDef | Brassica oleracea | CAC37558 |
| BoPCP | Brassica oleracea | CAA06465 |
| BSD1 | Brassica campestris | L47901 |
| CaDef1 | Cicer arietinum | ABC59238 |
| CaDef2 | Capsicum annuum | AAL35366 |
| CaDef3 | Cicer arietinum | ABCO2867 |
| CcDef | Cajanus cajan | AAP49847 |
| CfD1 | Cassia fistula | n/a |
| CfD2 | Cassia fistula | n/a |
| Cpthio1 | Vigna unguiculata | P83399 |
| CtAMP | Clitoria ternatea | AAB34971 |
| DmAMP1 | Dahlia merckii | AAB34972 |
| DRR39 | Pisum sativum | Q01784 |
| EGAD1 | Elaeis guineensis | AF322914 |
| Fabatin1 | Vicia faba | A58445 |
| Fabatin2 | Vicia faba | B58445 |
| FST | Nicotiana tabacum | P32026 |
| Part 2 | | |
| g1-Z | Zea mays | P81008 |
| g2-Z | Zea mays | P81009 |
| GbDef | Ginkgo biloba | AAU04859 |
| g-H1 | Hordeum vulgare | P20230 |
| GmPl | Glycine max | AAC97524 |
| g-P1 | Triticum turgidum | P20158 |
| g-P2 | Triticum turgidum | P20159 |
| g-thionin | Nicotiana paniculata | O24115 |
| HsAFP1 | Heuchera sanguinea | AAB34974 |
| HvAMP1 | Hardenbergia violavea | n/a |
| Jl-1 | Capsicum annuum | X95363 |
| Jl-2 | Capsicum annuum | X95730 |
| LCR66 | Arapidopsis thaliana | 090947 |
| LCR67 | Arapidopsis thaliana | NP_565119 |
| LCR68 | Arapidopsis thaliana | Q9ZUL7 |
| LCR69 | Arapidopsis thaliana | Q39182 |
| LCR70 | Arapidopsis thaliana | Q41914 |

TABLE 2-continued

Source and accession numbers of plant defensins used to construct phylogenetic tree

| Peptide | Source | Accession number |
|---|---|---|
| LCR72 | Arapidopsis thaliana | Q9ZUL8 |
| LCR73 | Arapidopsis thaliana | P82782 |
| LCR74 | Arapidopsis thaliana | Q9FFP8 |
| LCR77 | Arapidopsis thaliana | NP_199255 |
| LCR78 | Arapidopsis thaliana | P82787 |
| LmDef | Lepidium meyenii | AAV85992 |
| MsDef1.1 | Medicago sativa | AAV85437 |
| MsDef3.1 | Medicago sativa | AAT66095 |
| MsDef3.2 | Medicago sativa | AAT66096 |
| MtDef | Medicago truncatula | AAQ91290 |
| MtDef2 | Medicago truncatula | AY313169 |
| MsDef2.1 | Medicago sativa | AAV85438 |
| MtDef3.1 | Medicago truncatula | AAT66097 |
| MtDef3.1a | Medicago truncatula | AAT69983 |
| MtDefa | Medicago truncatula | AAQ91287 |
| NaD1 | Nicotiana alata | Q8GTMO |
| NaD2 | Nicotiana alata | none |
| NatD1 | Nicotiana attenuata | AAS13436 |
| Nethio1 | Nicotiana excelsior | BAA21114 |
| Nethio2 | Nicotiana excelsior | BAA21113 |
| Npthio1 | Nicotiana paniculata | O24115 |
| Part 3 | | |
| p322 | Solanum tuberosum | P20346 |
| PCP-A1 | Brassica oleracea | CAA06464 |
| PDF1.1 | Arabidopsis halleri | AAY27736 |
| PDF1.2 | Arabidopsis thaliana | NP_199256 |
| PDF1.3 | Arabidopsis thaliana | NP_180171 |
| PDF1.4 | Arabidopsis halleri | AAY27739 |
| PDF1.5 | Arabidopsis thaliana | NP_175899 |
| PgD1 | Picea glauca | AY494051 |
| PhD1 | Petunia hybrida | Q8H6Q1 |
| PhD2 | Petunia hybrida | Q8H6Q0 |
| PmDef | Plantago major | CAH58740 |
| PpDLP1 | Pyrus pyrifolia | BAB64930 |
| PpDLP2 | Pyrus pyrifolia | BAB64929 |
| PPT | Petunia inflata | L27173 |
| PsD1 | Pisum sativum | P81929 |
| PsD2 | Pisum sativum | P81930 |
| RsAFP1 | Raphanus sativus | P69241 |
| RsAFP2 | Raphanus sativus | P30230 |
| RsAFP3 | Raphanus sativus | CAA65984 |
| RsAFP4 | Raphanus sativus | O24331 |
| SaAFP1 | Sinapis alba | P30231 |
| SaAFP2a | Sinapis alba | P30232 |
| SD2 | Helianthus annuus | AF178634 |
| Sla1 | Sorghum bicolor | P21923 |
| Sla2 | Sorghum bicolor | P21924 |
| Sla3 | Sorghum bicolor | P21925 |
| SoD2 | Spinacia oleracea | P81571 |
| SPl1B | Picea abies | AAN40688 |
| TaDef | Triticum aestivum | AB089942 |
| TfAFP | Trigonella foenum-graecum | AAO72632 |
| TkAMPD1 | Triticum kiharae | P84963 |
| TkAMPD1.1 | Triticum kiharae | P84965 |
| TkAMPD1.2 | Triticum kiharae | P84964 |
| TkAMPD2 | Triticum kiharae | P84968 |
| TkAMPD3 | Triticum kiharae | P84970 |
| TkAMPD4 | Triticum kiharae | P84971 |
| TkAMPD5 | Triticum kiharae | P84966 |
| TkAMPD6 | Triticum kiharae | P84967 |
| TkAMPD6.1 | Triticum kiharae | P84969 |
| TpDef | Tephrosia platycarpa | AAX86993 |
| Part 4 | | |
| VaD1 | Vigna angularis | n/a |
| VrD1 | Vigna radiata | AAR08912 |
| VrD2 | Vigna radiata | 2GL1_A |
| WT1 | Wasabi japonica | BAB19054 |
| ZmES1 | Zea mays | AAK08132 |
| ZmES2 | Zea mays | AAK08133 |
| ZmES3 | Zea mays | AAK08134 |
| ZmES4 | Zea mays | AAK08135 |
| ZmESR6 | Zea mays | CAH61275 |

Proposed Classification of Plant Defensins

Neighbour-joining phylogenetic tree of plant defensin mature domains were constructed using MEGA 4.0. Bootstrap replicates greater than 50% are indicated. Defensins were separated into groups and subgroups (indicated on right) based on branch length. Branch scale=substitutions per residue. NaD1 is indicated by an arrow.

Known functions of defensins were mapped onto the phylogenetic tree with individual functions indicated by various symbols. The defensins of group 1 display the largest variety of activities including trypsin inhibition (Cpthio1, NaD2), α-amylase inhibition (SIα2-3, aainhi21), protein synthesis inhibition (γ-purothionins, γ-hordothionins) and sodium channel blocking (γ-Z1). Antifungal (EGAD1, SD2, JI-2, PgD1) and antibacterial (TaDef) activities have also been reported for some members of this group.

All group 2 defensins that have been functionally characterized display antibacterial activity, and some also possess α-amylase activity (VaD1, VrD1) or antifungal activity (VaD1, VrD1, SoD2). Defensins from groups 3 to 6 generally display antifungal activity, although CfD2, the only representative of group 4.1 is a trypsin inhibitor. An Arabidopsis plant defensin from group 5.3 (PDF1.3) is also involved in zinc tolerance, although its effect on fungal growth has not been investigated.

Group 7, which consists of only one member (ZmESR6), displays antifungal and antibacterial activities. Group 8 contains a defensin with α-amylase inhibitory (SIα1) activity and a sodium channel inhibitor (γ-Z2). Interestingly, these separate into distinct groups from their functional homologues in group 1.5 (SIα2-3 and γ-Z1), despite originating from the same plant species. The final group is composed of two defensins from Brassica species (BoPCP, PCP-A1) that have been implicated in pollen recognition.

In instances where defensins from a single species cluster together (for example, RsAFP1-4) these peptides are also found to have similar functions. When peptides from a single plant species are separated into different groups, such as NaD1 and NaD2 as well as VrD1 and VrD2, these defensins display different activities.

A circular view of the phylogenetic tree is shown in FIG. 10. Branches representing different groups are indicated on the outer circle. Known functions of individual peptides are indicated by symbols according to biological activity, as provided by the key.

The identification of over 300 defensin-like genes was recently reported for both Medicago and Arabidopsis (Graham et al, 2004; Silverstein et al, 2005). This suggests that plant defensins are members of large gene families with a variety of activities. The phylogenetic analysis undertaken here revealed defensins with similar activities often cluster together. This method of analysis may, therefore, prove useful in determining the activities of as yet uncharacterized defensins; however, real trends will only become apparent when the functions of more defensins have been established. Another limiting factor in the prediction of defensin function is that many of the defensins reported on to date have only been tested for one or two activities. In some instances, the reported activity of a peptide may not reflect its primary function.

All references throughout this application, for example, patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification reflect the level of skill of those skilled in the art to which the invention pertains. References cited herein indicate the state of the art, in some cases as of their filing dates, and it is intended that this information can be employed herein, if needed, to exclude (for example, to disclaim) specific embodiments that may be in the prior art.

When a group of substituents is disclosed herein, it is understood that all individual members of those groups and all subgroups, including any isomers and enantiomers of the group members with the same biological activity, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every combination of components described or exemplified or referenced can be used to practice the invention, unless otherwise stated. Specific names of compounds are intended to be exemplary, as it is known that one of ordinary skill in the art can name the same compounds differently. One of ordinary skill in the art will appreciate that methods, starting materials, synthetic methods and recombinant methodology other than those specifically exemplified can be employed in the practice of the invention without resort to undue experimentation. All art-known functional equivalents, of any such methods, starting materials, synthetic methods, and recombinant methodology are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition, method or system, is understood to encompass those compositions, methods and systems consisting essentially of and consisting of the recited components or elements or steps. The invention illustratively described herein suitably may be practiced in the absence of any element or elements, limitation or limitations which is not specifically disclosed herein.

One skilled in the art readily appreciates that the present invention is well adapted to carry out the objects and obtain the ends and advantages mentioned, as well as those inherent in the present invention. The methods, components, materials and dimensions described herein as currently representative of preferred embodiments are provided as examples and are not intended as limitations on the scope of the invention. Changes therein and other uses which are encompassed within the spirit of the invention will occur to those skilled in the art, are included within the scope of the claims.

Although the description herein contains certain specific information and examples, these should not be construed as limiting the scope of the invention, but as merely providing illustrations of some of the embodiments of the invention. Thus, additional embodiments are within the scope of the invention and within the following claims.

It should be noted that the crop scientist, agriculturist or botanist would know how to and when to terminate, interrupt, or adjust administration due to toxicity or a deleterious effect on performance of the plant to be protected. Conversely, the artisan would also know to adjust treatment to higher levels if the response were not adequate (precluding toxicity). The magnitude of an administered dose of fungicide and/or defensin or the level of expression of a recombinantly expressed defensin can be adjusted by means known to one of skill in the relevant arts, or the administration means or formulation for the fungicide and/or defensin, if applied to the plant or seed, can be changed to improve protection of the plant from fungal pathogens. The severity of the condition may, for example, be evaluated, in part, by standard prognostic evaluation methods. Further, the dose and perhaps dose frequency, will also vary according to the age, size, soil and/or climatic conditions and response of the individual plant.

Use of agronomically acceptable carriers to formulate the compound(s) herein disclosed for the practice of the invention into dosages suitable for systemic and surface administration is within the scope of the invention and within the ordinary level of skill in the art. With proper choice of carrier and suitable manufacturing practice, the compositions of the present invention, in particular those formulated as solutions, may be administered to plant surfaces including above-ground parts and/or roots, or as a coating applied to the surfaces of seeds.

Agronomically useful compositions suitable for use in the system disclosed herein include compositions wherein the active ingredient(s) are contained in an effective amount to achieve the intended purpose. Determination of the effective amounts is well within the capability of those skilled in the art, especially in light of the disclosure provided herein.

In addition to the active ingredients, these compositions for use in the antifungal method may contain suitable agronomically acceptable carriers comprising excipients and auxiliaries which facilitate processing of the active compounds into preparations which can be used in the field, in greenhouses or in the laboratory setting.

Antifungal formulations include aqueous solutions of the active compounds in water-soluble form. Additionally, suspensions of the active compounds may be prepared as appropriate oily suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Further components can include viscosifiers, gels, wetting agents, ultraviolet protectants, among others.

Preparations for surface application can be obtained by combining the active compounds with solid excipient, optionally grinding a resulting mixture, and processing the mixture of granules, after adding suitable auxiliaries, if desired, to obtain powders for direct application or for dissolution prior to spraying on the plants to be protected. Suitable excipients are, in particular, fillers such as sugars, including lactose, sucrose, mannitol, or sorbitol; cellulose or starch preparations, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention is further described in the following details.

Purification of NaD1 from *Pichia pastoris* and from *Nicotiana alata*

The *Pichia pastoris* expression system is well-known and commercially available from Invitrogen (Carlsbad, Calif.; see the supplier's *Pichia* Expression Manual disclosing the sequence of the pPIC9 expression vector).

A single pPIC9-NaD1 *P. pastoris* GS115 colony was used to inoculate 10 mL of BMG medium (described in the Invitrogen *Pichia* Expression Manual) in a 100 mL flask and was incubated overnight in a 30° C. shaking incubator (140 rpm). The culture was used to inoculate 500 mL of BMG in a 2 L baffled flask which was placed in a 30° C. shaking incubator (140 rpm). Once the $OD_{600}$ reached 2.0 (~18 h), cells were harvested by centrifugation (2,500×g, 10 min) and resuspended into 1 L of BMM medium ($OD_{600}$=1.0) in a 5 L baffled flask and incubated in a 28° C. shaking incubator for 3 days. The expression medium was separated from cells by centrifugation (4750 rpm, 20 min) and diluted with an equal volume of 20 mM potassium phosphate buffer (pH 6.0). The medium was adjusted to pH 6.0 with NaOH before it was applied to an SP Sepharose column (1 cm×1 cm, Amersham Biosciences) pre-equilibrated with 10 mM potassium phosphate buffer, pH 6.0. The column was then washed with 100 mL of 10 mM potassium phosphate buffer, pH 6.0 and bound protein was eluted in 10 mL of 10 mM potassium phosphate buffer containing 500 mM NaCl. Eluted proteins were subjected to RP-HPLC using a 40 minute linear gradient as described herein below. Protein peaks were collected and analyzed by SDS-PAGE and immunoblotting with the anti-NaD1 antibody. Fractions containing NaD1 were lyophilized and resuspended in sterile milli Q ultrapure water. The protein concentration of *Pichia*-expressed NaD1 was determined using the bicinchoninic acid (BCA) protein assay (Pierce Chemical Co.) with bovine serum albumin (BSA) as the protein standard.

To isolate NaD1 from its natural source, whole *N. alata* flowers up to the petal coloration stage of flower development were ground to a fine powder and extracted in dilute sulphuric acid as described previously (Lay et al, 2003). Briefly, flowers (760 g wet weight) were frozen in liquid nitrogen, ground to a fine powder in a mortar and pestle, and homogenized in 50 mM sulfuric acid (3 mL per g fresh weight) for 5 min using an Ultra-Turrax homogenizer (Janke and Kunkel). After stirring for 1 h at 4° C., cellular debris was removed by filtration through Miracloth (Calbiochem, San Diego, Calif.) and centrifugation (25,000×g, 15 min, 4° C.). The pH was then adjusted to 7.0 by addition of 10 M NaOH and the extract was stirred for 1 h at 4° C. before centrifugation (25,000×g, 15 min, 4° C.) to remove precipitated proteins. The supernatant (1.8 L) was applied to an SP Sepharose™ Fast Flow (GE Healthcare Bio-Sciences) column (2.5×2.5 cm) pre-equilibrated with 10 mM sodium phosphate buffer. Unbound proteins were removed by washing with 20 column volumes of 10 mM sodium phosphate buffer (pH 6.0) and bound proteins were eluted in 3×10 mL fractions with 10 mM sodium phosphate buffer (pH 6.0) containing 500 mM NaCl. Samples from each purification step were analyzed by SDS-polyacrylamide gel electrophoresis (SDS-PAGE) and immunoblotting with the anti-NaD1 antibodies. Fractions from the SP Sepharose column containing NaD1 were subjected to reverse-phase high performance liquid chromatography (RP-HPLC).

Reverse-Phase High Performance Liquid Chromatography

Reverse-phase high performance liquid chromatography (RP-HPLC) was performed on a System Gold HPLC (Beckman) coupled to a detector (model 166, Beckman) using a preparative C8 column (22×250 mm, Vydac) with a guard column attached. Protein samples were loaded in buffer A (0.1% [v/v] trifluoroacetic acid) and eluted with a linear gradient of 1-100% (v/v) buffer B (60% [v/v] acetonitrile in 0.089% [v/v] trifluoroacetic acid) at a flow rate of 10 mL/min over 40 min. Proteins were detected by monitoring absorbance at 215 nm. Protein peaks were collected and analyzed by SDS-PAGE.

Samples from each stage of NaD1 purification (30 μL) were added to NuPAGE® (Registered Trademark) LDS sample loading buffer (10 μL, Invitrogen) and heated to 70° C. for 10 min. The samples were then loaded onto NuPAGE® precast 4-12% Bis-Tris polyacrylamide gels (Invitrogen) and the proteins were separated using an XCell-Surelock electrophoresis apparatus (Invitrogen) run at 200 V. Proteins were visualized by Coomassie Blue staining or transferred onto nitrocellulose for immunoblotting with the anti-NaD1 antibodies.

Preparation of Reduced and Alkylated NaD1

Lyophilized NaD1 (500 μg) was dissolved in 400 μL of stock buffer (200 mM Tris-HCl pH 8.0, 2 mM EDTA, 6 M guanidine-HCl, 0.02% [v/v] Tween®-20). Reduction buffer (stock buffer with 15 mM dithiothreitol [DTT]) was added (44 μL) followed by a 4.5 h incubation at 40° C. The reaction mixture was cooled to RT before iodoacetic acid (0.5 M in 1 M NaOH, 55 μL) was added and the incubation continued in the dark for 30 min at RT. A Nanosep Omega® (Registered Trademark) spin column (3K molecular weight cut off, PALL Life Sciences) was used to remove salts, DTT and iodoacetic acid and the protein concentration was determined using the BCA protein assay (Pierce). The effect of reduced and alkylated NaD1 ($NaD1_{R\&A}$) on the growth of *Fusarium oxysporum* (Fov) was measured as described herein.

Immunoblot Analysis

For immunoblot analysis, proteins were transferred to nitrocellulose and probed with protein A-purified anti-NaD1 antibodies (1:3000 dilution of 7.5 mg/mL) followed by goat anti-rabbit IgG conjugated to horseradish peroxidase (1:3500 dilution; Amersham Pharmacia Biotech). Enhanced chemiluminescence (ECL) detection reagents (Amersham Pharmacia Biotech) were used to visualize bound antibodies with a ChemiGenius™ bioimaging system (Syngene).

To produce anti-NAD1 antiserum, purified NaD1 (1.5 mg) was conjugated to Keyhole Limpet Hemocyanin (0.5 mg, Sigma) with glutaraldehyde as described by Harlow and Lane (1988). A rabbit was injected with 1.5 mL of protein (150 µg NaD1) in an equal volume of Freund's complete adjuvant (Sigma). Booster immunizations of conjugated protein (100 µg NaD1) and Freund's incomplete adjuvant (Sigma-Aldrich) were administered four and eight weeks later. Pre-immune serum was collected before injection and immune serum was collected 14 d after the third and fourth immunizations. The IgG fraction from both pre-immune and immune serum was purified using Protein-A Sepharose CL-4B (Amersham Pharmacia Biotech) and was stored at −80° C. at concentrations of 3.4 mg/mL and 7.5 mg/mL, respectively.

Analysis of Activity Against Filamentous Fungi, Yeast, Bacteria and Human Cells

Antifungal activity against *Fusarium oxysporum* f. sp. *vasinfectum* (Fov, Australian isolate VCG01111 isolated from cotton; from Wayne O'Neill, Farming Systems Institute, DPI, Queensland, Australia), *Fusarium graminearum* (Australian isolate CS3005 isolated from wheat; from CSIRO, University of Queensland, Queensland, Australia), *Thielaviopsis basicola* (gift from David Nehl, NSW DPI, Narrabri, Australia), *Verticillium dahliae* (from Wayne O'Neill, Farming Systems Institute, DPI, Queensland, Australia), *Leptosphaeria maculans* (from Barbara Howlett, The University of Melbourne, Victoria, Australia) and *Aspergillus nidulans* (from Michael Hynes, The University of Melbourne) was assessed essentially as described in Broekaert et al (1990). Spores were isolated from sporulating cultures growing in either half-strength potato dextrose broth (PDB) (Fov and *T. basicola*), Czapeck-Dox Broth (*V. dahliae*) (Difco Laboratories) or 10% (v/v) clarified V8 medium (*L. maculans* and *A. nidulans*) by filtration through sterile muslin. Spore concentrations were determined using a hemocytometer and adjusted to $5 \times 10^4$ spores/mL in the appropriate growth medium. Spore suspensions (80 µL) were added to the wells of sterile 96-well flat-bottomed microtitre plates along with 20 µL of filter-sterilized (0.22 µm syringe filter; Millipore) NaD1, or water to give final protein concentrations of 0-10 µM. The plates were shaken briefly and placed in the dark at 25° C. without shaking until the optical density at 595 nm of the water control reached approximately 0.2 (24-72 h depending on growth rate). Hyphal growth was estimated by measuring the optical density at 595 nm using a microtitre plate reader (SpectraMax Pro M2; Molecular Devices). Each test was performed in quadruplicate.

The effect of NaD1 on the growth of the yeast strains *Candida albicans*, *Pichia pastoris* and *Saccharomyces cerevisiae* (from Department of Microbiology, La Trobe University) was assayed in microtitre plates. Cells were grown in YPD for 48 h, then counted using a haemocytometer and diluted to a concentration of $5 \times 10^4$ cells/mL in fresh YPD. Cell suspension (100 µL) containing 0-10 µM NaD1 was added to the wells of a 96-well microtitre plate and incubated for 48 h at 30° C. Growth was determined by measuring the optical density at 595 nm using a microtitre plate reader. Each test was performed in quadruplicate.

The effect of NaD1 on bacterial growth, as determined using strains of *Escherichia coli*, *Pseudomonas aeruginosa*, *Staphylococcus aureus* and *Bacillus cereus* (Department of Microbiology, La Trobe University) was assayed in microtitre plates. Cells were grown overnight in Luria-Bertani broth and diluted to a concentration of $1 \times 10^4$ cells/mL. Ten µL of the diluted overnight culture was then added to 190 µL of LB containing 0-10 µM NaD1. Plates were incubated at 37° C. without shaking for 24 h. Growth was determined by measuring the optical density at 595 nm using a microtitre plate reader. Each sample was performed in quadruplicate.

To examine the effect of NaD1 on mammalian cell growth, HeLa cells were seeded at 50% in Dulbecco's modified Eagle's medium (Gibco™-BRL) containing 10% (v/v) fetal calf serum with or without NaD1 (10 µM) at 37° C. under an atmosphere of 5% $CO_2$ and 95% air in a 60 mm Petri dish. Cells were incubated for 48 h at 37° C. before they were stained with trypan blue to check viability and counted using a haemocytometer.

The effect of NaD1 on the growth of Insect cells was determined as follows. *Spodoptera frugiperda* (Sf21) insect cells were grown to ~90% confluency in Sf-900 II serum free media (Gibco™, 20 mL) in a 75 $cm^2$ tissue culture flask with a vented cap (Nunc). Cells were then split one in two with fresh media. Cell suspension was added to 96-well flat-bottomed microtitre plate wells (190 µL/well) and the cells were allowed to settle for 30 min prior to addition of NaD1 (10 µL) to give a final concentration of 0-10 µM. Growth was monitored until the cells reached confluency (~48 h).

Effect of Metal Ions on NaD1 Activity

The activity of NaD1 against Fov was examined as described with varying concentrations of $CaCl_2$ (0.1, 0.2, 0.5, 1.0 and 2.0 µM) or $MgCl_2$ (1.0, 2.0, 10, 20 and 50 µM) present in the medium to determine the effects of divalent cations on NaD1 activity.

NaD1 and Membrane Permeabilization

Fov hyphae were grown in half-strength PDB (10 mL in a 50 mL tube) from a starting concentration of $5 \times 10^4$ spores/mL for 18 h at 25° C. with constant shaking. Samples (1 mL) were then removed and NaD1 (final concentration 2 µM), $NaD1_{R\&A}$ (final concentration 2 µM) or an equivalent volume of water was added before incubation for 2 h at RT with gentle agitation. SYTOX® green (Invitrogen-Molecular Probes, Eugene, Oreg.) was added to a final concentration of 0.5 µM and the hyphae were allowed to stand for 10 min. Hyphae (20 µL) were then transferred to microscope slides (SuperFrost® Plus, Menzel-Glaser) and glass coverslips were mounted on the slides for visualization of the hyphae by fluorescence microscopy using an Olympus BX51 fluorescence microscope. SYTOX® green fluorescence was detected using an MWIB filter (excitation wavelength 460-490 nm). Images were captured using a SPOT RT 3CCD digital camera (Diagnostic Instruments) and processed using Adobe Photoshop. SYTOX® green uptake was quantitated by measuring fluorescence of hyphae in microtitre trays using a fluorimeter (SpectraMax M2; Molecular Devices) with excitation and emission wavelengths of 488 nm and 538 nm, respectively.

The uptake of FITC-labeled dextran with NaD1 treatment of fungal hyphae was also studied. Fov hyphae were grown as described above and incubated with NaD1 (final concentration 0.1, 2, 10 or 50 µM) or an equivalent volume of water for 2 h at RT with gentle agitation. Hyphae were washed twice for 10 min with half-strength PDB to remove excess NaD1 before FITC dextrans of either 4 kDa (FD-4, Sigma-Aldrich) or 10 kDa (FD-10, Sigma-Aldrich) were added to a final concentration of 1 mg/mL. Hyphae were incubated for a further 30 min at RT and then washed twice with half strength PDB to remove excess dextrans. Fluorescence microscopy was used to visualize hyphae as described for SYTOX® green. A second assay was performed under the same conditions except the dextrans were added at the same time as NaD1.

The effect of temperature on membrane permeabilization of Fov hyphae by NaD1 was monitored as described, except hyphae were pre-equilibrated for 60 min at either 10°, 4° or 0° C. before addition of NaD1 and all subsequent steps were carried out at these temperatures.

The kinetics of membrane permeabilization by NaD1 were studied. Fov hyphae were grown in half-strength PDB from a starting concentration of $5 \times 10^4$ spores/mL for 18 h at 25° C. Hyphae (80 μL) were then transferred to 96-well microtitre plates and incubated with SYTOX® green (0.5 μM) for 10 min prior to the addition of 20 μL of peptide solution to give final protein concentrations of 0.2, 0.4, 0.8, 1.6, 3.12, 6.25, 12.5, 25, 50 or 100 μM. Fluorescence readings (Ex; 488 nm, Em; 538 nm) were then taken every 2 min for 3 h using a fluorimeter (SpectraMax M2).

Isolation of NaD1 from Treated Hyphae

Fov hyphae were grown as described above prior to the addition of NaD1 (10 μM final concentration) to 1 mL of the culture. Samples (100 μL) were collected after 0, 5, 10, 30, 60, 90 and 120 min. Hyphae were collected by centrifugation (10 min, 10,000×g) and the supernatant was stored at −20° C. for analysis. Hyphae were washed (2×10 min) with KCl (0.6 M) to remove any ionically bound protein before they were resuspended in 50 mM CAPS buffer (pH 10.0) containing 10 mM DTT for 20 min. Hyphae were collected by centrifugation and the supernatant, containing cell wall proteins, was collected for analysis. The pellet (containing cells) was resuspended in water and the cells were lysed using glass beads (Sigma, 60 mg) and vortexing (3×10 min). Cellular debris was removed by centrifugation (16,000×g, 10 min) and the supernatant collected for analysis. All samples were then analyzed by SDS-PAGE and immunoblotting.

Electron Microscopy

Fov hyphae were grown for 18 h in half-strength PDB (5 mL) with vigorous shaking at 25° C. from a starting spore suspension of $5 \times 10^4$/mL. Hyphae were then treated with 2 μM NaD1 or an equivalent volume of water for 2 h at RT with gentle agitation, washed twice in 0.6 M KCl were washed three times in PBS before fixation in 4% (w/v) paraformaldehyde in PBS for 1 h at 4° C. Hyphae were again washed three times in PBS before dehydration in a standard ethanol series (15 min each, 50%, 70% and 90% ethanol, 3×15 min 100% ethanol). Hyphae were then infiltrated with LR White resin (ProSciTech) for 1 h at RT, followed by 18 h at 4° C., 1 h at RT and 24 h at 60° C. Fresh LR White resin was used at each step. Ultrathin sections were cut and placed on Formvar coated gold grids.

Grids were blocked with PBS containing 8% (w/v) BSA and 1% (v/v) Triton X-100 for 1 h and labeled with anti-NaD1 antibodies (2 μg/mL in blocking buffer) for 1 h. Grids were washed in blocking buffer (3×10 min) and labeled with 15 nm gold particle labeled goat anti-rabbit antibodies (ProSciTech) for 1 h. Grids were washed again in blocking solution (3×10 min) followed by water (15 min) before being air-dried. A JEOL JEM2010HC×e80 KV transmission electron microscope was used to examine labeled grids. Pictures were taken on Kodak EM film (ProSciTech) and developed in a dark room before scanning on a Hewlett Packard Scanjet 5P scanner.

Monitoring Uptake of Fluorescently Labeled NaD1

Fluorescein isothiocyanate (FITC) was conjugated to NaD1 using the EZ-Label™ FITC protein labeling kit (Pierce) as described by the manufacturer.

To produce bimane amine labeled NaD1, lyophilized NaD1 was dissolved in 0.1 M MES buffer (pH 5.0) to a final concentration of 2 mM. The fluorescent tag bimane amine (Invitrogen-Molecular Probes) was added to a final concentration of 10 mM along with 1-ethyl-3-(3-dimethylaminopropyl)-carbodiimide (EDC, final concentration of 2 mM). The reaction was incubated at RT for 2 h with gentle stirring before centrifugation (13,000 rpm, 10 min) to remove any precipitated protein. A Nanosep omega 3K spin column (PALL life sciences) was used to remove salts, unbound bimane amine and EDC. The bimane-labeled NaD1 was resuspended in water and the protein concentration was determined using the BCA protein assay (Pierce).

Hyphae grown for 18 h as described were treated with NaD1-bimane (2 μM) for between 10 min and 6 h. Hyphae were then visualized by fluorescence microscopy using an MWU filter (excitation wavelength of 330-385 nm).

Detection of Reactive Oxygen Species in Response to NaD1 Treatment

Fov hyphae were grown as described herein and incubated with 5 μg/mL dihydrorhodamine 123 (Sigma-Aldrich) for 2 h followed by extensive washing with growth medium. Hyphae were then treated with NaD1 (2 μM) or water for 1 h before being washed with 0.6 M KCl. Fluorescence was then measured on a fluorimeter with excitation and emission wavelengths of 488 nm and 538 nm respectively or visualized by fluorescence microscopy. The experiment was repeated either in the presence of ascorbic acid (10 mM) or 2,2,6,6-tetramethylpiperidine-N-oxyl (TEMPO, 3 mM).

Production of Transgenic Plant Cells and/or Tissue

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al (1988).

Techniques for genetically engineering plant cells and/or tissue with an expression cassette comprising an inducible promoter or chimeric promoter fused to a heterologous coding sequence and a transcription termination sequence are to be introduced into the plant cell or tissue by *Agrobacterium*-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamicin, or bleomycin.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art. Suitable plant transformation vectors include those derived from a Ti plasmid of *Agrobacterium tumefaciens*, such as those disclosed by Herrera-Estrella (1983), Bevan et al (1983), Klee et al (1985) and EPO publication 120,516 (Schilperoort et al). In addition to plant transformation vectors derived from the Ti or root-inducing (Ri)

plasmids of *Agrobacterium*, alternative methods can be used to insert the DNA constructs of this invention into plant cells.

The choice of vector in which the DNA of interest is operatively linked depends directly, as is well known in the art, on the functional properties desired, e.g., replication, protein expression, and the host cell to be transformed, these being limitations inherent in the art of constructing recombinant DNA molecules. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector may also be a Lambda phage vector including those Lambda vectors described in Molecular Cloning: A Laboratory Manual, Second Edition, Sambrook et al, eds., Cold Spring Harbor Press (1989) and the Lambda ZAP vectors available from Stratagene (La Jolla, Calif.). Another vector includes, for example, pCMU (Nilsson et al (1989)). Other appropriate vectors may also be synthesized, according to known methods; for example, vectors pCMU/Kb and pCMUII used in various applications herein are modifications of pCMUIV (Nilson et al, supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens*.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al (1989); Walden and Schjell (1990); Joersbo and Burnstedt (1991); Potrykus (1991); Gasser and Fraley (1989); Leemans (1993); Beck et al (1993); Koziel et al (1993); and Vasil et al (1993)). Techniques are well-known to the art for the introduction of DNA into monocots as well as dicots, as are the techniques for culturing such plant tissues and regenerating those tissues.

Monoclonal or polyclonal antibodies, preferably monoclonal, specifically reacting with a polypeptide or protein of interest may be made by methods known in the art. See, e.g., Harlow and Lane (1988); Goding (1986); and Ausubel et al (1993). Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al (1989); and Ausubel et al (1993). Abbreviations and nomenclature, where employed, are deemed standard in the field and commonly used in professional journals such as those cited herein.

Example 1

Inhibition of the Growth of *Fusarium graminearum* in the Presence of NaD1 and Chemical Fungicides In Vitro The inhibitory effects of defensin (NaD1) and chemical fungicides on the growth of *Fusarium graminearum* (Australian isolate CS3005 provided by CSIRO Plant Industry, St. Lucia, Queensland, Australia) were measured essentially as described by Broekaert, W. F. et al (1990). Spores were isolated from sporulating cultures growing in synthetic nutrient poor broth (SNPB). The cultures were grown in half strength potato dextrose broth (PDB) for 1-2 weeks at room temperature, before spores were collected by passing the culture through sterile tissue paper to remove hyphal matter. Spore concentrations were measured using a hemocytometer.

NaD1, prepared as described in the detailed descriptions, was diluted to provide a series of 10× stock solutions of the final concentrations shown in FIG. 1. The fungicides propiconazole (Cat No. 45642, 98.96% purity), tebuconazole (Cat No. 36565, 99.6% purity), flusilazole (Cat No. 45753, 99.8% purity), azoxystrobin, (Cat No. 46160, 99.9% purity) and picoxystrobin (Cat No. 33658, 99.9% purity) were obtained from Sigma Chemical Co., St. Louis. Mo. Stock solutions were prepared in 100% methanol at 100× final concentration.

Antifungal assays were conducted in 96 well microtiter trays essentially as described in the detailed description (analysis of antifungal activity). Wells were loaded with 10 uL of filter sterilized (0.22 μm syringe filter, Millipore) NaD1 (10× stock for each final concentration) or water, 1 uL fungicide (100× stock for each final concentration) and 90 uL $5\times10^4$ spores/mL in ½ strength PDB. The plates were incubated at 25° C. for 44 or 45 hours. Fungal growth was assayed by measuring optical density at 595 nm ($A_{595}$) using a microtitre plate reader (SpectraMax Pro M2; Molecular Devices). Each test was performed in quadruplicate.

Results

Defensin enhanced the antifungal activity of several fungicides in a synergistic manner when assessed in in vitro assays with *F. graminearum* (FIG. 1).

Synergism between NaD1 and propiconazole (FIG. 1A) was most evident when comparing the growth curves obtained with 0 and 0.5 μM defensin. 0.5 μM defensin (alone) inhibited fungal growth by about 13% and 0.06 mg/L propiconazole (alone) also inhibited fungal growth by about 13%. However the combination of 0.5 μM defensin and 0.06 mg/L propiconazole inhibited fungal growth by about 78%. Similar synergism was observed with combinations of NaD1 with tebuconazole (FIG. 1B), flusilazole (FIG. 1C), azoxystrobin (FIG. 1D) and picoxystrobin (FIG. 1E). The experiments shown in FIGS. 1G and 1H were repeated (results shown in FIG. 1A) to obtain more accurate measurements of inhibition in the critical range of 0-0.25 mg/L propiconazole in order to more accurately assess synergy according to the Limpel formula.

Synergy calculations from the data presented on FIGS. 1A-1E are set forth in FIG. 1F wherein Ee is the expected effect from the additive response according to Limpel's formula (Richer, 1987) expressed as percent inhibition and Io is the percent inhibition observed. One concentration of NaD1 (0.5 µM) and two concentrations of each fungicide were used for the synergy calculations. Synergy, that is, Io values higher than Ee values was obtained with the two strobilurins and the three triazoles that were tested in combination with 0.5 µM NaD1.

Example 2

Inhibition of the Growth of *Fusarium oxysporum* in the Presence of NaD1 and Chemical Fungicides In Vitro The inhibitory effects of defensin (NaD1) and chemical fungicides on the growth of *Fusarium oxysporum* f. sp. *vasinfectum* (Fov) (Australian isolate VCG01111 isolated from cotton and provided by Farming Systems Institute, DPI, Queensland, Australia) were measured essentially as described by Broekaert, et al (1990). Spores were isolated from sporulating cultures growing in ½ strength potato dextrose broth (PDB). The Fov culture was grown in ½ PDB for 1-2 weeks at room temperature, before spores were separated from hyphal matter by filtration through sterile tissue paper. The concentration of spores in the filtrate was measured using a hemocytometer. NaD1 and the fungicides were prepared as described in Example 1. The conditions used for the fungal growth assay were the same as those described in Example 1.

Results

Defensin enhanced the antifungal activity of several fungicides in a synergistic manner when assessed in in vitro assays with Fov (FIG. 2). Defensin had a synergistic effect on the inhibitory activity of azoxystrobin against *Fusarium oxysporum* (FIG. 2A). The synergism between the two compounds was most obvious when comparing the growth curves obtained with 0 and 0.24 µM defensin and 0-1 mg/L azoxystrobin (FIGS. 2A and 2B). Synergy could not be assessed at higher concentrations of defensin and azoxystrobin where the toxicity of the individual components was too high.

Figure 2A:
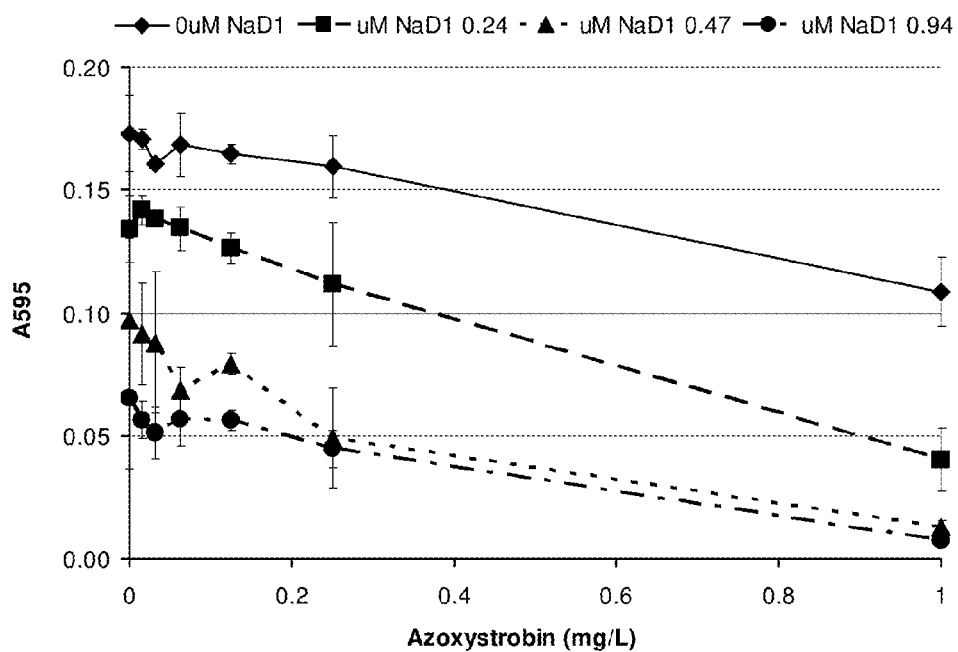
Figure 2B:
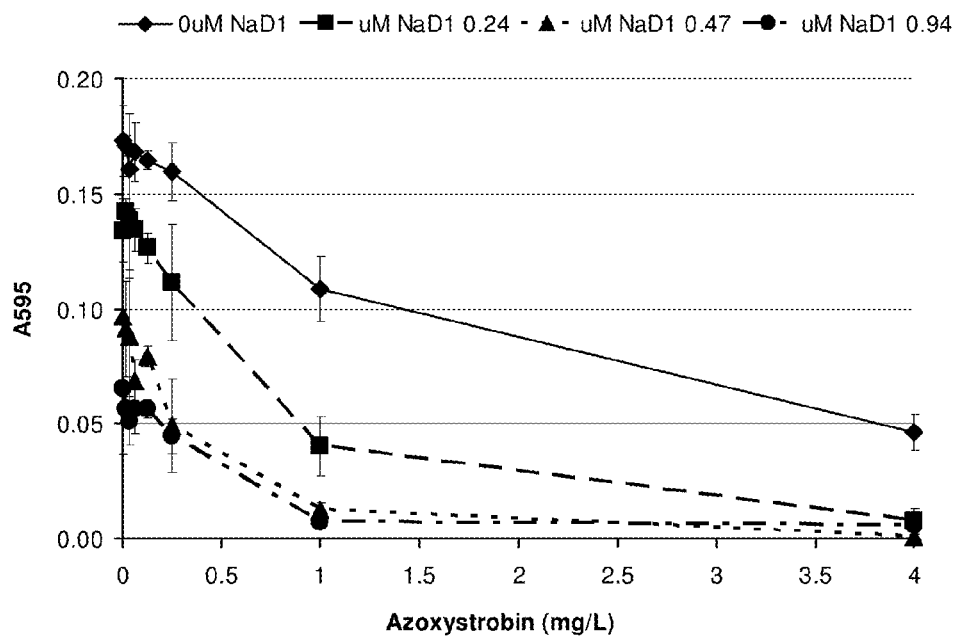
Figure 2C:
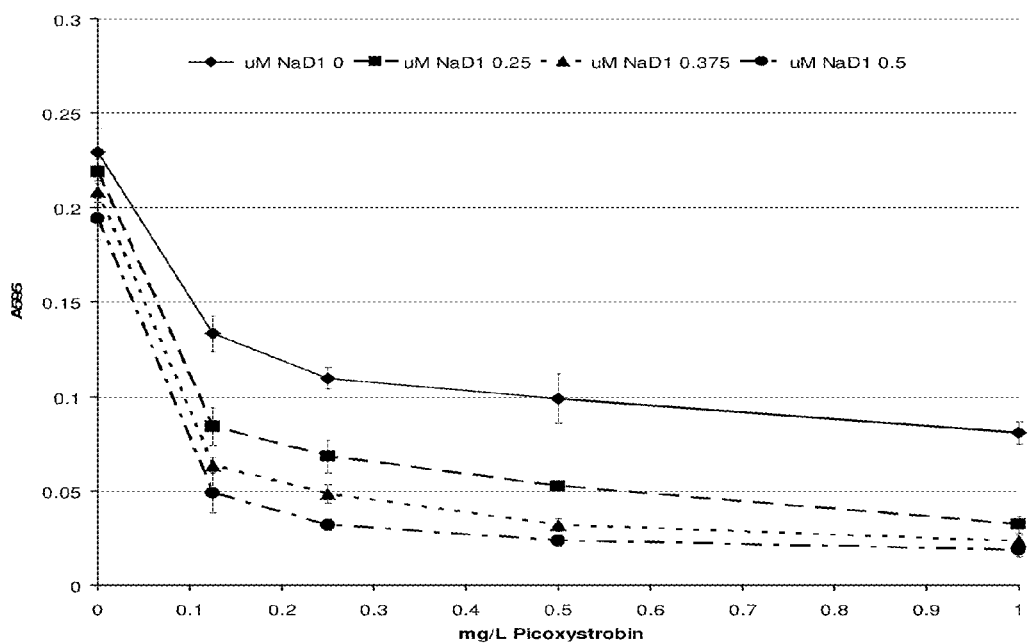
Figure 2D:
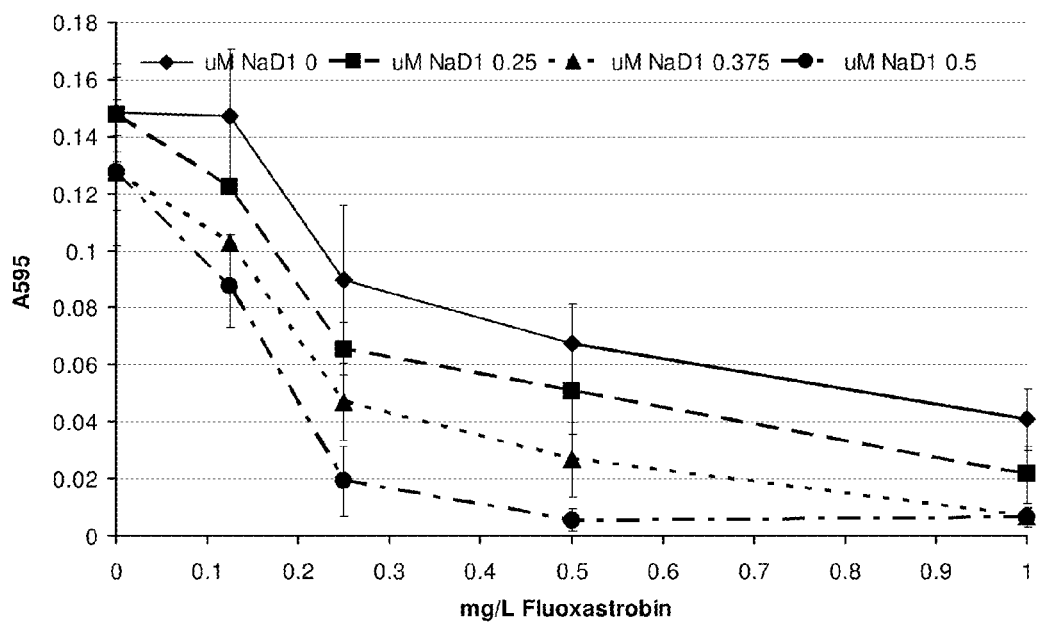
Figure 2E:
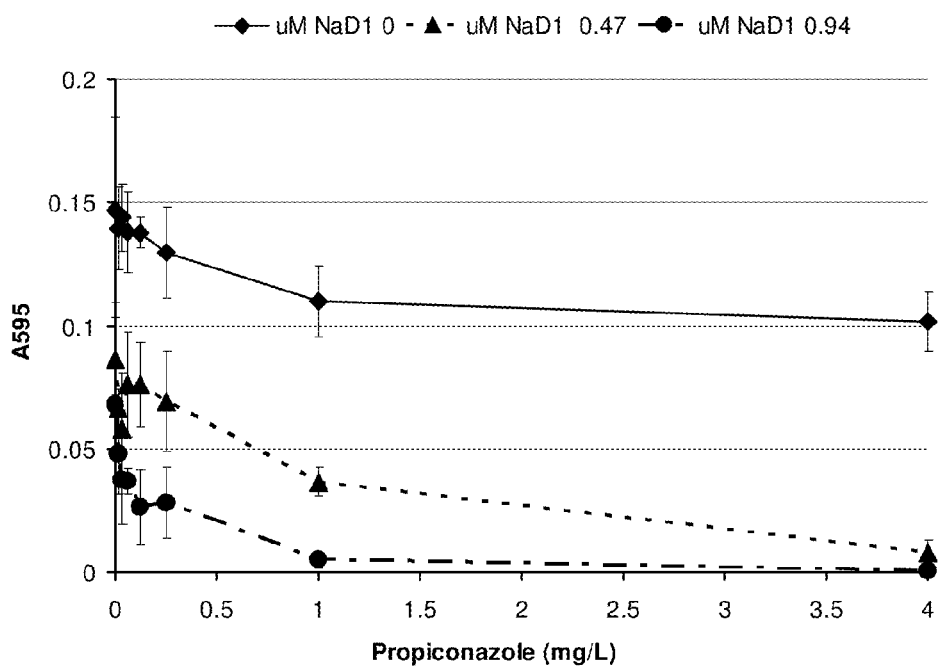
Figure 2F:
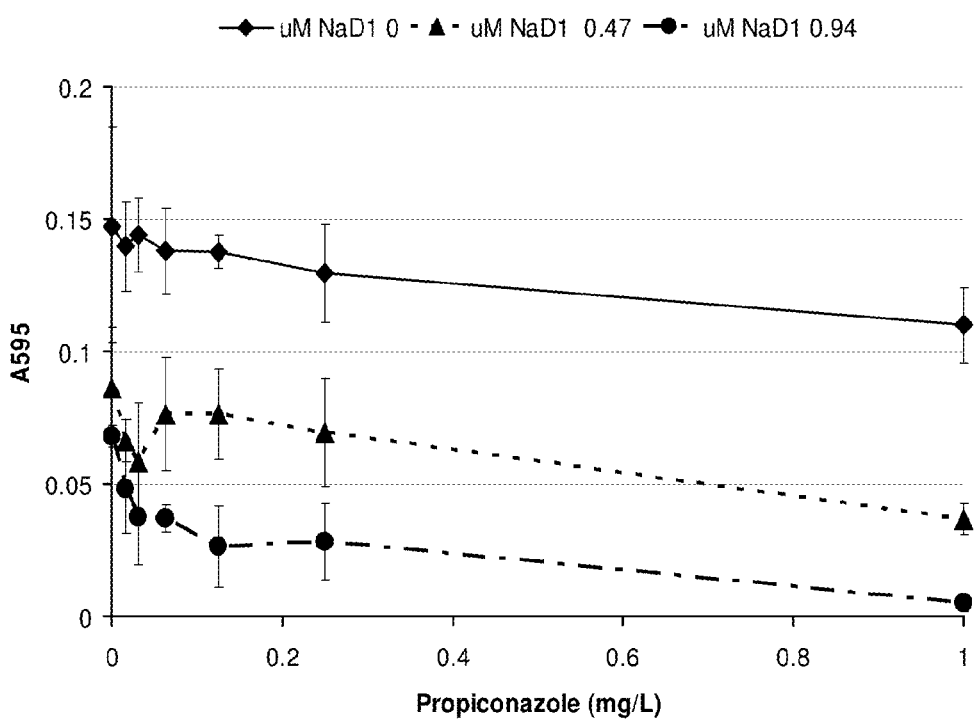

FIG. 2C illustrates the synergy between picoxystrobin and defensin. FIG. 2D illustrates the synergy between fluoxastrobin and defensin. Synergism between propiconazole and defensin was also evident when growth curves in the presence of 0 and 0.47 µM defensin and 0.125-4 mg/L propiconazole were compared (FIGS. 2E and 2F). The experiments shown in FIGS. 2H and 2I were repeated (results shown in FIG. 2C) to obtain more accurate measurements of inhibition in the critical range of 0-1 mg/L picoxystrobin in order to more accurately assess synergy according to the Limpel formula.

Figures 2G, 2H:
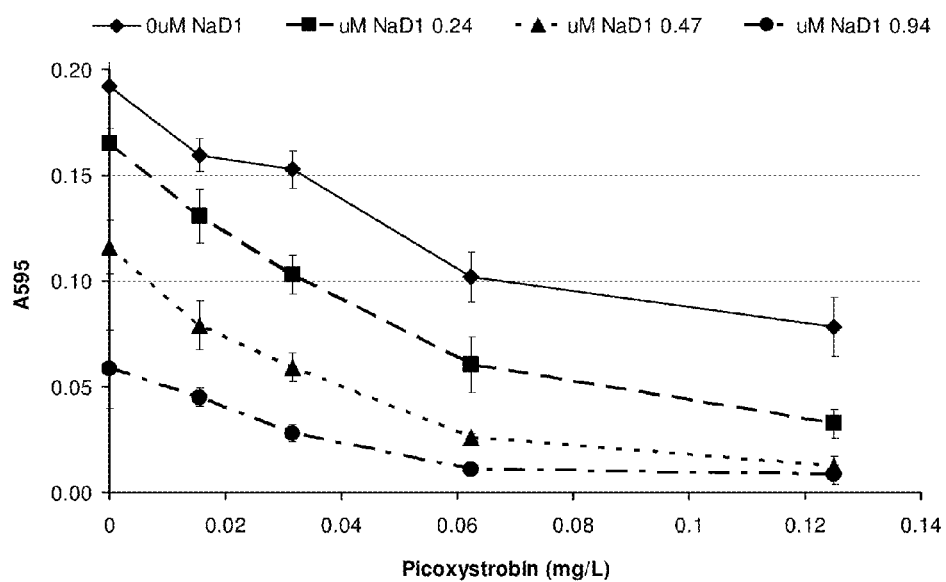
Figure 2I:
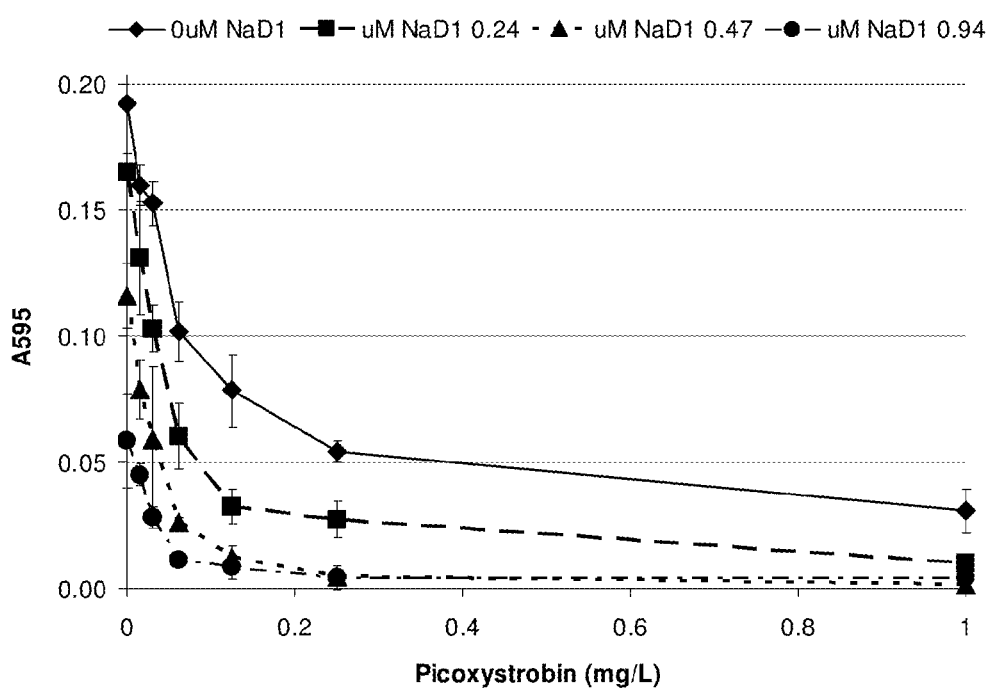

Synergy calculations are set forth in FIG. 2G wherein Ee is the expected effect from the additive response according to Limpel's formula (Richer, 1987) expressed as percent inhibition and Io is the percent inhibition observed. One concentration of NaD1 (0.5 µM) and two concentrations of each fungicide were used for the synergy calculations. Synergy, that is, Io values higher than Ee values was obtained with all the strobilurins and the triazole that were tested in combination with 0.5 µM NaD1.

Comparison of the results described in Examples 1 and 2 illustrates that the extent of synergy between defensin and a particular antifungal molecule varies from one pathogen to another. That is, for *Fusarium graminearum* the best synergy was obtained with the combination of triazoles and defensin whereas better synergy was obtained with strobilurins and defensin in the *Fusarium oxysporum* bioassays.

Example 3

Inhibition of *Fusarium oxysporum* f.Sp. *Vasinfectum* (Fov) Infection in Transgenic Cotton Seedlings Expressing NaD1. Effect of Seed Coating with Chemical Fungicides Transgenic cotton line 35.125.1 was previously described in U.S. Pat. No. 7,041,877, incorporated herein by reference. Line 35.125.1 was transformed with full length nucleic acid encoding the defensin NaD1.

Glasshouse Bioassay of Transgenic and Non-Transgenic Cotton Seed Coated with Fungicide in *Fusarium oxysporum* f.Sp. *Vasinfectum* Infected Soil.

A glasshouse bioassay with infected soil was used to assess the level of resistance to Fov in non-transgenic Coker 315 and transgenic Coker 315 expressing NaD1 (line 35.125.1, U.S. patent application Ser. No. 12/105,956). Cultures of Fov (isolate #24500 VCG 01111) were prepared in millet and incorporated into a soil mix. The infected soil was used to grow line 35.125.1 and non-transgenic Coker 315. The culture of Fov was prepared in ½ strength PDB (12 g/L potato dextrose) and grown for approximately one week at 26° C. The culture (5 to 10 mL) was used to infect autoclaved hulled millet which was then grown for 2 to 3 weeks at room temperature. The infected millet was incorporated into a pasteurized peat based soil mix at 1% (v/v), by vigorous mixing in a 200 L compost tumbler. The infected soil was transferred to plastic containers (10 L of mix per 13.5 L container).

The cotton seed was either non-coated or coated with the fungicide HEC5725 (active ingredient Fluoxastrobin, Bayer Crop Science, batch number 06529/0022) at a rate of 1 mL/kg of seed and allowed to dry prior to sowing. Water was added to facilitate even coating of the seed (62.5 mL/kg of seed). Untreated samples were treated with water only.

Forty eight seeds were planted for each test (transgenic and non-transgenic, coated and non-coated seed). Seed was sown directly into the containers, 12 seed per box in a 3×4 array. Three seed for each test were sown randomly in each box.

Plants were grown for 7 weeks. Foliar symptom development was measured throughout the trial and disease score was determined by destructive sampling at the end of the trial. The following rating was used to determine the disease score: 0=no symptoms, 1=vascular browning to base of stem, 2=vascular browning to cotyledons, 3=vascular browning past cotyledons, 4=vascular browning to true leaves, 5=dead. The average disease score was an average for all seeds that germinated.

Results

The results of the Fov bioassay with coated and non-coated seeds of non-transgenic Coker and Coker expressing NaD1 are presented in FIG. 3A. Fifteen percent of non-transgenic Coker plants that had not been treated with fungicide died from Fov infection. Treatment of the non-transgenic seed with the fungicide did not enhance survival or improve the disease score.

In contrast, transgenic Coker expressing NaD1 had approximately half the mortality of the non-transgenic plants, even when the seeds had not been coated with fungicide. Significantly, no mortality was obtained when the transgenic seeds had been coated with fungicide. This demonstrates that the fungicide which had not protected the non-transgenic plants from Fov infection did enhance protection against Fov infection in plants expressing defensin. Furthermore, the combination of fungicide with transgenic expression of the NaD1 defensin resulted in a large decrease in disease score relative to coated transgenic seed and an even larger decrease in disease score relative to plants that were not expressing defensin.

Growth Cabinet Bioassay of Transgenic and Non-Transgenic Cotton Seed Coated with Fungicide in *Fusarium oxysporum* f.Sp. *Vasinfectum* Infected Soil.

A growth cabinet bioassay with infected soil was used to assess the level of resistance to Fov in non-transgenic Coker 315 and transgenic Coker 315 expressing NaD1 (line 35.125.1). The assay was conducted as described for the glasshouse assay except for the following modifications.

Thirty seeds were planted for each test (transgenic and non-transgenic, coated and non-coated seed). Seed was sown directly into the containers, 24 seed per box in a 4×6 array. Six seed for each test were sown randomly in each box. Seeds were germinated for 7 days, conditions were 16 hours light at 30° C. and 8 hours dark at 15° C., with a ramp of 2° C. per hour. For the remainder of the experiment the conditions were 16 hours light at 25° C. and 8 hours dark at 10° C. with a ramp of 2° C. per hour.

Plants were grown for 4 weeks. Foliar symptom development was measured throughout the trial and disease score was determined by destructive sampling at the end of the trial. The following rating was used to determine the disease score: 0=no symptoms, 1=vascular browning to base of stem, 2=vascular browning to cotyledons, 3=vascular browning past cotyledons, 4=vascular browning to true leaves, 5=dead. The average disease score was an average for all seeds that germinated.

Results

The results of the Fov bioassay with coated and non-coated seeds of non-transgenic Coker and Coker expressing NaD1 are presented in FIG. 3B. Eighteen percent of non-transgenic Coker plants that had not been treated with fungicide died from Fov infection. Non-transgenic Coker plants that had been treated with fungicide showed some reduction in mortality (13%) and slight improvement of the disease score (1.7 to 1.6).

In contrast, transgenic Coker expressing NaD1 had less than half the mortality of the non-transgenic plants (7% instead of 18%), even when the seeds had not been coated with fungicide. Significantly, no mortality was obtained when the transgenic seeds had been coated with fungicide. This demonstrates that the fungicide which had only weakly protected the non-transgenic plants from Fov infection did enhance protection against Fov infection in plants expressing defensin. Furthermore, the combination of fungicide with transgenic expression of the NaD1 defensin resulted in a large decrease in disease score relative to coated transgenic seed and an even larger decrease in disease score relative to plants that were not expressing defensin.

Field Trial of Transgenic and Non-Transgenic Cotton Seed Coated with Fungicide in *Fusarium oxysporum* f.Sp. *Vasinfectum* Infected Soil.

Transgenic cotton line 35.125.1 (D1) (U.S. Pat. No. 7,041,877) expressing the defensin NaD1 and untransformed Coker 315 were assessed in a small scale field trial in the Australian cotton season. Seed of the two lines were either not coated with fungicide or were coated with the fungicide HEC5725 (active ingredient fluoxastrobin, Bayer CropScience, batch number 06529/0022) at a rate of 1 mL/kg of seed, or with the commercial seed coat fungicides Dynasty® (Registered Trademark) (active ingredients 75 g/L azoxystrobin, 37.5 g/L metalaxyl-m, 12.5 g/L fludioxonil, Syngenta) at a rate of 2 mL/kg of seed, Jockey® (Registered Trademark) (active ingredient 167 g/L fluquinconazole, Bayer CropScience) at a rate of 20 mL/kg of seed or Redigo® (Registered Trademark) (active ingredient 100 g/L prothioconazole, Bayer CropScience) at a rate of 1 mL/kg of seed. All seed (coated and uncoated with fungicide) was coated with the insecticide Gaucho® (Registered Trademark) (600 g/L imidacloprid, Bayer CropScience) to control early season *thrips* and *aphids*. Seed was prepared to ensure even coating of fungicide and insecticide and allowed to dry prior to sowing.

Plants were grown at a farm in the Darling Downs region of Queensland, Australia. Seed was mechanically planted into soil known to be infected with *Fusarium oxysporum* f.sp. *vasinfectum*. A total of about 1450 seed per variety/treatment were planted in eight replicate plots, each containing about 180 seeds per variety/treatment.

Emergence and plant survival were recorded. About 1100-1400 seeds germinated. Statistical significance of the interaction of plant line and mortality was calculated using a Pearson's chi-square test.

Boll yield, lint yield and lint quality is assessed at the end of the trial.

Results

FIGS. 3C-3F illustrate the level of mortality up to 57 days after sowing of seeds that had been coated or non-coated with chemical fungicides.

FIG. 3C is a graphical representation of the results obtained with Jockey®. Seedlings from non-transgenic Coker seed that had been coated with the fungicide exhibited increased mortality relative to the non-coated seed although the difference was not significant (P=0.07). In contrast, seedlings from Jockey® coated seed of transgenic line 35.125.1 expressing NaD1 exhibited significantly less mortality (p 0.004) than seedlings from the same line that had not been coated. Overall at day 57 mortality of the seedlings from the fungicide coated 35.125.1 seeds was 31.6% compared to 50.2% mortality of the seedlings from coated non-transgenic Coker.

FIG. 3D is a graphical representation of the results obtained with Dynasty®. Seedlings from non-transgenic Coker seed that had been coated with the fungicide exhibited increased mortality relative to the non-coated seed and this difference was significant (P=0.000). Once again seed of the transgenic line 35.125.1 expressing NaD1 was more resistant to fungal infection than the non-transgenic lines whether coated with fungicide or uncoated. At 57 days post-germination seedlings from the fungicide coated seeds of line 35.125.1 exhibited significantly less mortality (p 0.012) than seeds from the same line that had not been coated. At day 57 mortality of the seedlings from the fungicide coated 35.125.1 seeds was 32.3% compared to 54.2% mortality of seedlings from coated non-transgenic Coker.

FIGS. 3E and F display the results obtained with Redigo® and HEC5725. In both cases seedlings from non-transgenic Coker seed that had been coated with the fungicides were more susceptible to infection than seedlings from non-coated seed (P=0.044 and P=0.001 respectively). Seedlings from non-coated and coated line 35.125.1 exhibited significantly less mortality than non-transgenic Coker. The survival of HEC5725 (FIG. 3F) coated 35.125.1 seeds appeared slightly higher than the non-coated 35.125.1 seeds but this difference was not significant (P=0.493). Similarly there was no significant difference in mortality between seedlings produced from Redigo® coated or non-coated seeds (P=0.755).

Figure 3C:
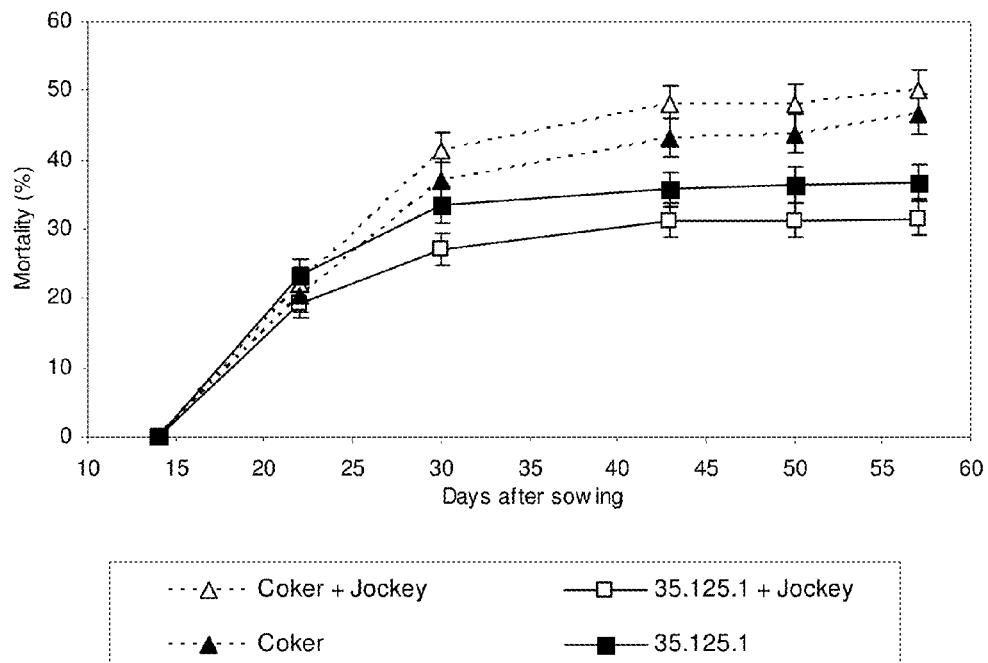
Figure 3D:
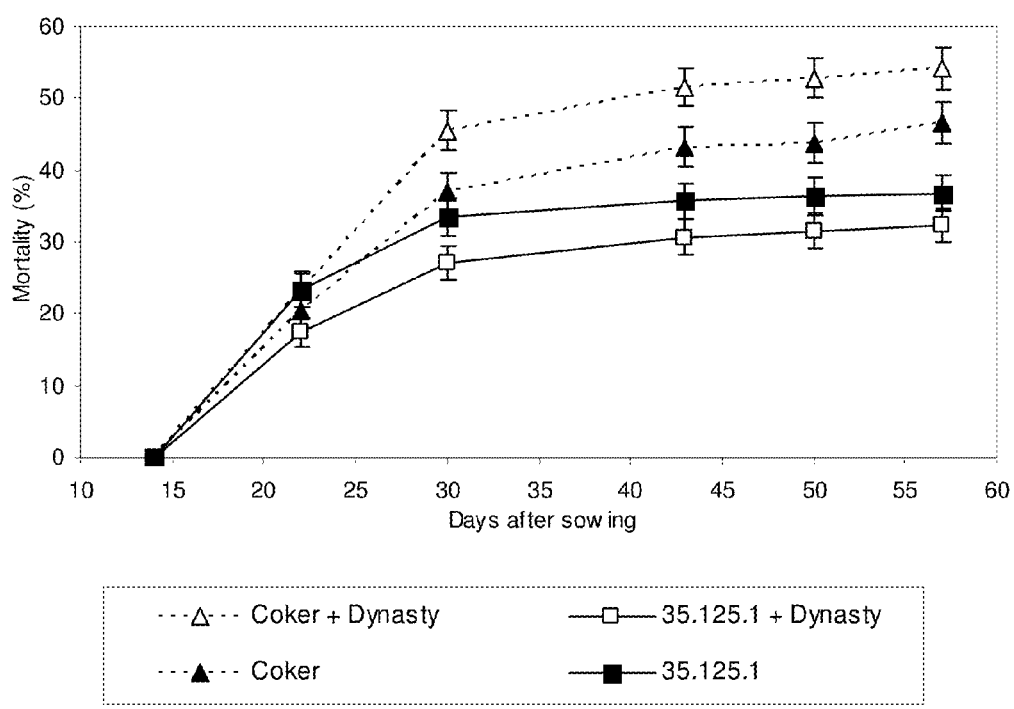
Figure 3E:
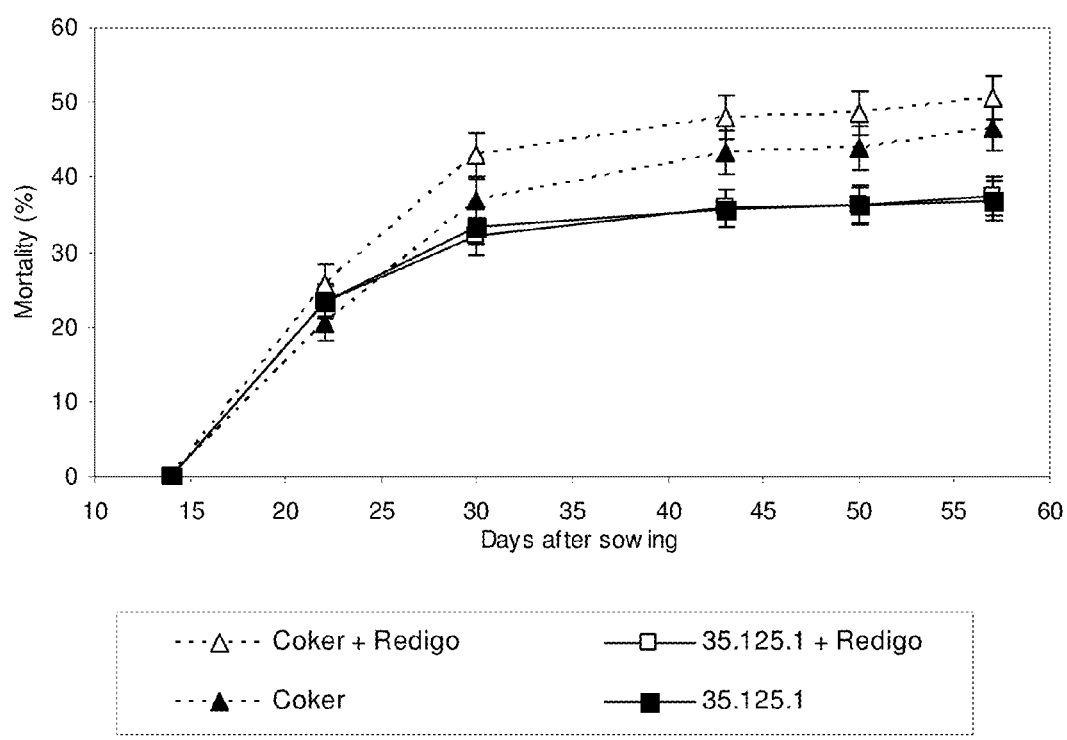
Figure 3F:
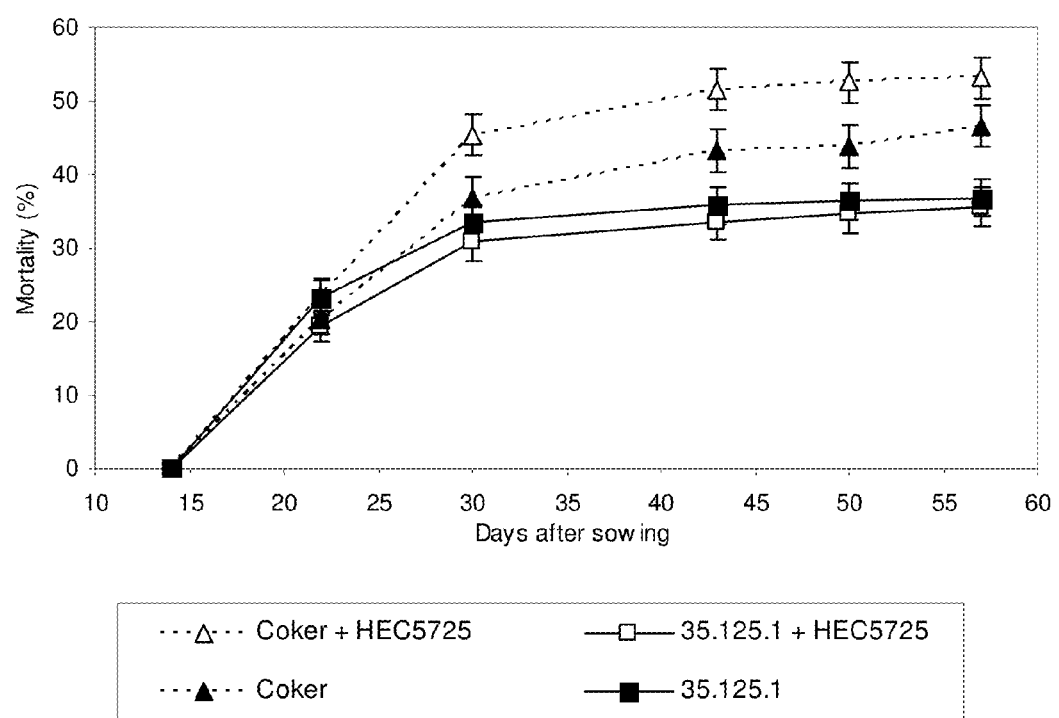

Synergy calculations from the data presented in FIGS. 3C-F are set forth in FIG. 3G wherein Ee is the expected effect from the additive response according to Limpel's formula (Richer, 1987) expressed as percent improved survival and Io is the percent improved survival observed. The calculations were based on the percentage differences relative to the Coker non-treated control. Synergy, that is, Io values higher than Ee values were obtained when seeds of the transgenic line 35.125.1 were coated with Jockey®, Dynasty®, Redigo® or HEC5725.

Example 4

Inhibition of the Growth of *Verticillium Dahlia* in the Presence of NaD1 and Chemical Fungicides In Vitro The inhibitory effects of defensin (NaD1) and chemical fungicides were assayed on growth of *Verticillium dahliae* (Australian isolate VCG-4B, Dr. Stephen Allen, Cotton Seed Distributors, Narrabri, NSW, Australia) in vitro.

Spores of *V. dahliae* were isolated from sporulating cultures growing in Czapek-Dox broth (Difco) for 1-2 weeks at room temperature. Spores were separated from hyphal matter by filtration through sterile tissue paper and the concentration of spores in the filtrate was measured using a hemocytometer. NaD1 and the fungicides were prepared as described in Example 1. The conditions used for the fungal growth assay were the same as those described in Example 1 except that Czapek-Dox broth was used in place of PDB.

Results

Figure 4A:
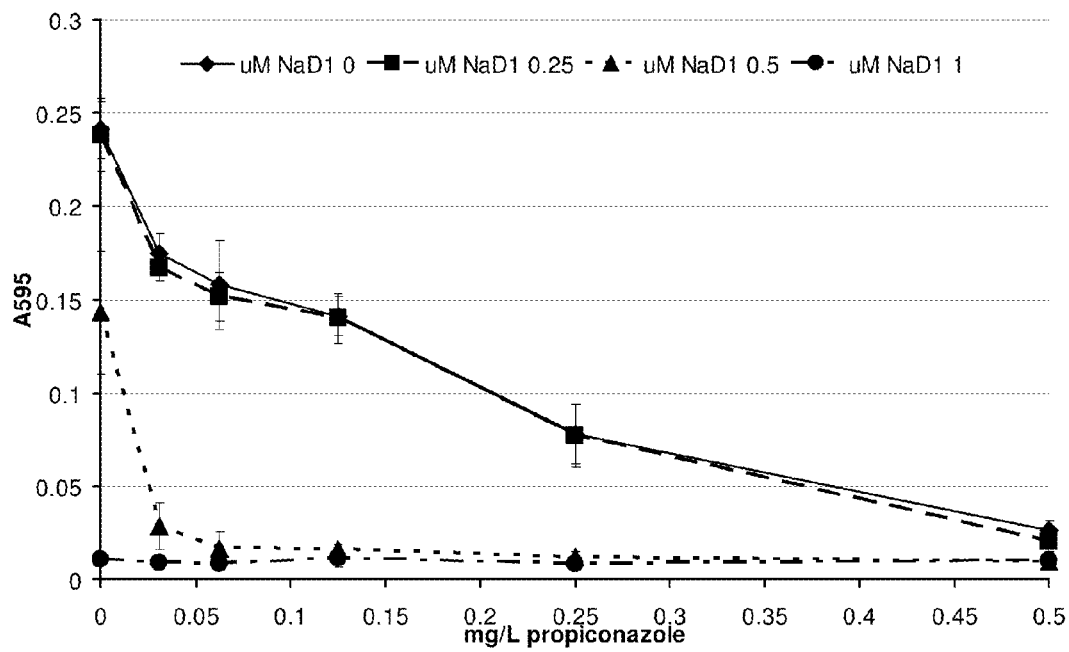
Figure 4B:
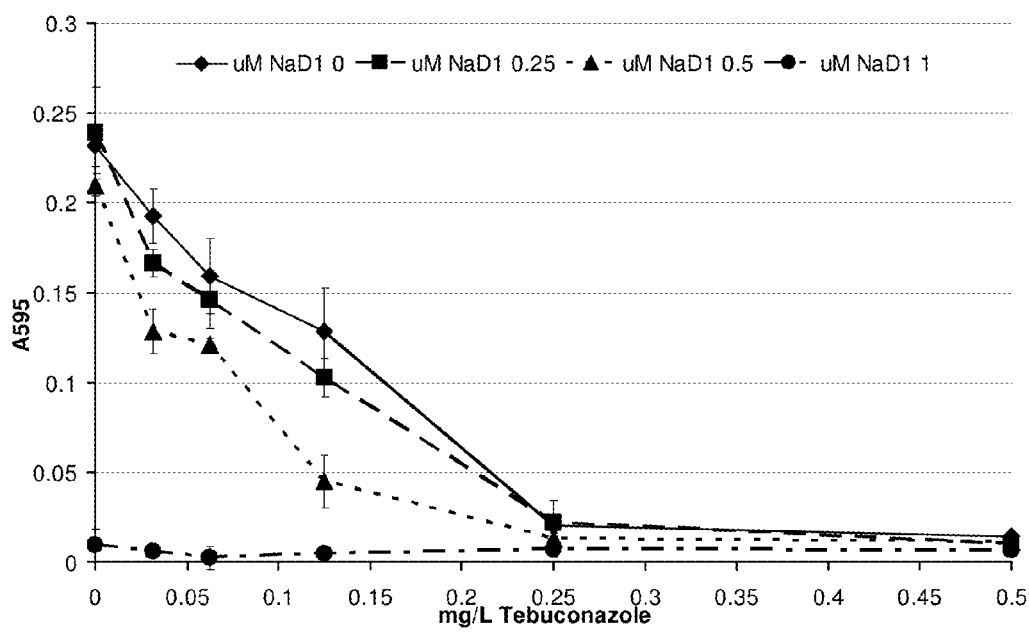
Figures 4C, 4D:
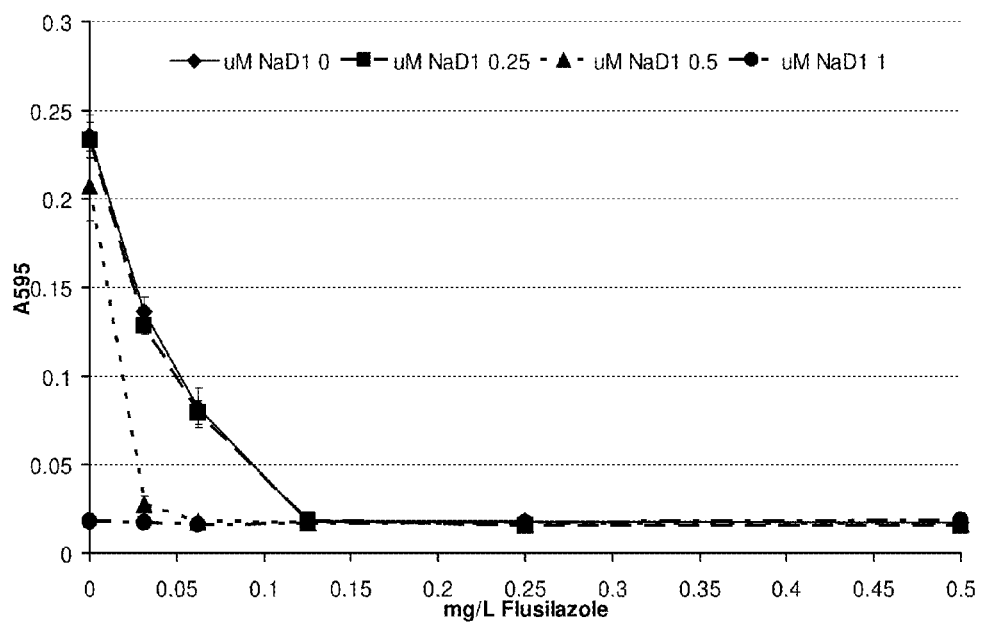

Synergism between NaD1 and propiconazole (FIG. 4A), NaD1 and tebuconazole (FIG. 4B) and NaD1 and flusilazole (FIG. 4C) was obvious when the growth curves with no added NaD1 were compared to those obtained with 0.5M NaD1 particularly in the range of 0-0.06 mg/L propiconazole and flusilazole and 0-0.125M tebuconazole. Synergy results are also set forth in FIG. 4D wherein Ee is the expected effect from the additive response according to Limpel's formula (Richer, 1987) expressed as percent inhibition and Io is the percent inhibition observed. One concentration of NaD1 (0.5 µM) and two concentrations of each fungicide were used for the synergy calculations. Synergy, that is, Io values higher than Ee values was obtained with all three triazoles that were tested in combination with 0.5 µM NaD1.

Example 5

Inhibition of *Verticillium dahliae* Infection in Transgenic Cotton Seedlings Expressing NaD1
Effect of Seed Coating with Chemical Fungicides Transgenic cotton line 35.125.1 was previously described in U.S. Pat. No. 7,041,877. Line 35.125.1 was transformed with full length nucleic acid encoding the defensin NaD1. Sicala V2 was obtained from Cotton Seed Distributors, Wee Waa, New South Wales, Australia 2388.
Field Trial of Transgenic and Non-Transgenic Cotton Seed Coated with Fungicide in *Verticillium dahliae* Infected Soil.

Transgenic cotton line 35.125.1 (U.S. Pat. No. 7,041,877) expressing the defensin NaD1, untransformed Coker 315 and the commercial variety Sicala V2, which is less susceptible to *V. dahliae* infection (Australian Industry Standard), were assessed in a small scale field trial in the Australian cotton season. Seed of the three lines were either not coated with fungicide or were coated with the commercial seed coat fungicide Dynasty® (Registered Trademark) (Syngenta, 2 mL/kg). Dynasty contains the following fungicides: 75 g/L azoxystrobin, 37.5 g/L metalaxyl-m and 12.5 g/L fludioxonil. Dynasty® (Registered Trademark) is registered for the control of seedling damping-off diseases of cotton caused by *Pythium* spp and *Rhizoctonia solani*. All seed (coated and uncoated with fungicide) were coated with the insecticide Gaucho (Bayer, 600 g/L imidacloprid) to control early season *thrips* and *aphids*.

Plants were grown at a farm near Merah North, NSW, Australia. Seed was hand planted into soil known to be infected with *V. dahliae*. A total of 500 seed per variety/treatment were planted in five replicate plots, each containing 100 seeds per variety/treatment.

Emergence, plant survival and incidence of *Verticillium* foliar symptoms were recorded. At the end of the trial, the plants were assessed for disease by measuring the vascular discoloration visible in a cross section of the main stem cut as close as practicable to ground level. The number of plants with an absence of vascular discoloration was determined and this information was used to calculate a *Verticillium* Rank as follows. The proportion of plants with an absence of vascular discoloration (denoted T) was calculated by dividing the number of plants with no vascular discoloration by the number of plants in the initial plant stand. This calculation was also performed for the industry standard plant line Sicala V2 and was denoted S. If the value of T was less than the value of S the following formula was used to determine the *Verticillium* Rank: 100×T/S. If the value of T was more than the value of S then the formula 100+[(T–S)/(100–S)×100] was used. The standard plant Sicala V2 is given a *Verticillium* Rank of 100. Boll yield, lint yield and lint quality were also assessed at the end of the trial. Every plant was assessed for all the measurements taken.

Results

Germination with the Dynasty® (Registered Trademark) seed coat treatment was 72 to 80%, while germination was only 60 to 62% for non-coated seeds. This confirms that the Dynasty® (Registered Trademark) seed coat protected some of the emerging plants from seedling diseases such as *Pythium* spp and *Rhizoctonia solani*. After 4 weeks there was no significant difference in survival of transgenic and non-transgenic Coker plants with and without the seed treatments (FIG. 5A).

At the end of the trial there was no difference in the level of *Verticillium* infection in non-transgenic plants from the coated (0.4% uninfected) and non-coated (1.0% uninfected) seeds. The level of infection was lower in the transgenic line expressing NaD1 than the non-transgenic lines. In addition, the highest number of uninfected plants was obtained with the combination of transgenically expressed NaD1 with fungicide seed coating (5.1% uninfected for coated seeds versus 3.6% uninfected for non-coated seeds). The *Verticillium* disease rank of the NaD1 transgenic line (35.125.1) that had been treated with the seed coat was equivalent to the *Verticillium* disease rank of the industry standard Sicala V2, and was 10 times higher than the *Verticillium* disease rank of the non-transgenic parent line Coker that had also been seed coated.

The synergy between NaD1 and the fungicide seed coat was most apparent when yield of bolls and lint was examined.

Although anti-*Verticillium* activity of the NaD1 was evident from lowered level of infection and from prior in vitro assays, yield was not significantly different between the transgenic line 35.125.1 and the untransformed Coker control when the Dynasty® (Registered Trademark) seed coat was not used (FIG. 5B) in this experiment. In contrast, boll yield was significantly enhanced when seed from the transgenic line 35.125.1 had been coated with Dynasty® (Registered Trademark) (FIG. 5B). This result suggests that there was a synergistic effect between NaD1 expressed in the transgenic plants and at least one component of the Dynasty® (Registered Trademark) fungicide.

Example 6

Inhibition of the Growth of *Leptosphaeria maculans* in the Presence of NaD1 and Chemical Fungicides In Vitro The defensin (NaD1) and the chemical fungicides prothioconazole (Sigma-Aldrich Cat #34232, 99.9% pure) and fluquinconazole (Nova Chem, Cat #C13805000, 98.5% pure) were assessed for their individual and combined inhibitory effects on the growth of *Leptosphaeria maculans* (Australian isolate IBCN18, Prof. B. Howlett) in vitro.

Figure 6A:
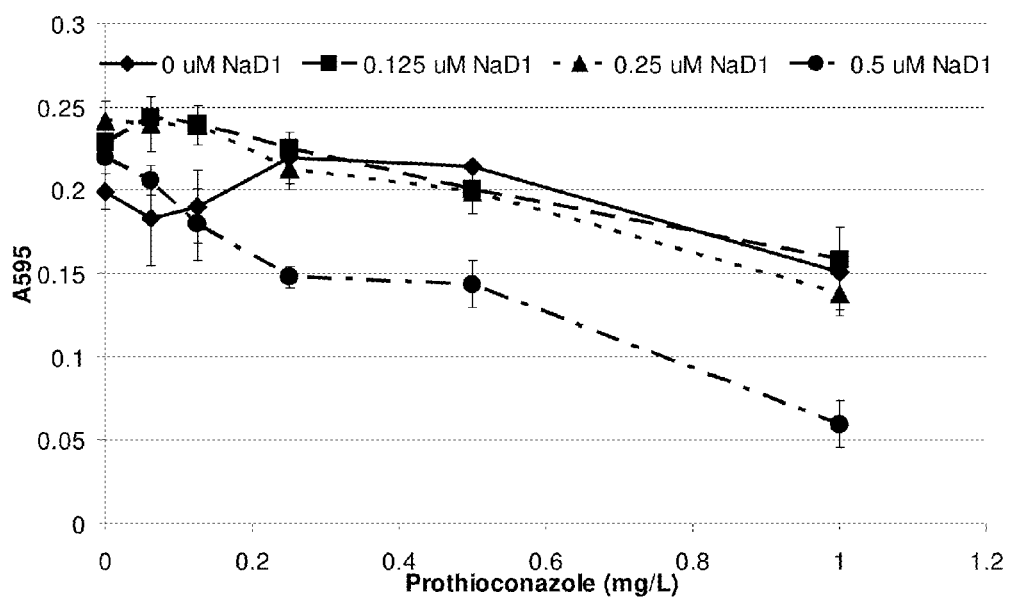
Figure 6B:
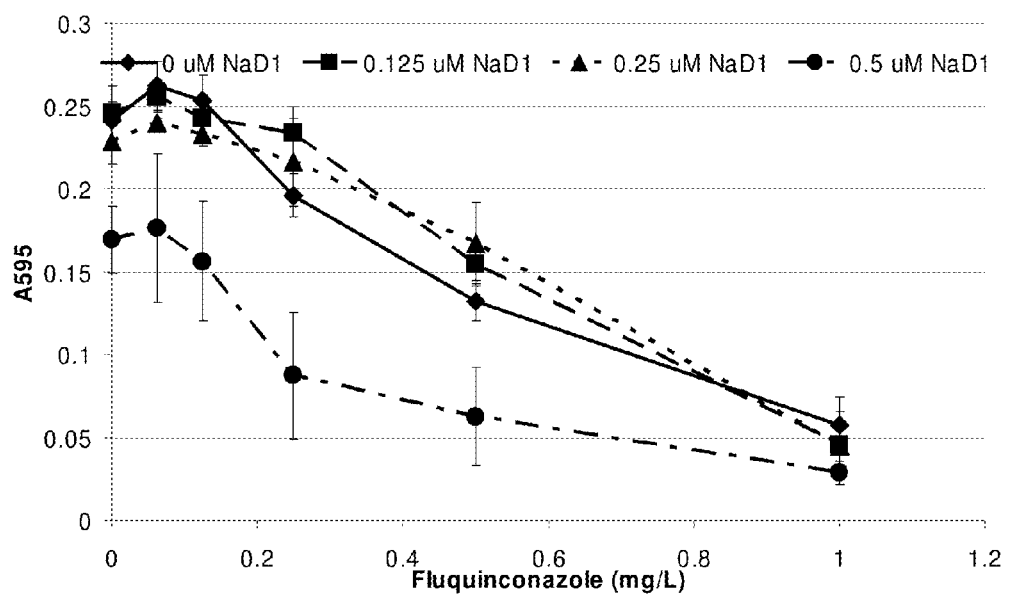

*Leptosphaeria maculans* was grown in 10% (v/v) V8 medium for about 2 weeks. Spores were collected by filtration through sterile muslin and adjusted to a final concentration of $5 \times 10^4$ spores/mL. The conditions used for the fungal growth assay were the same as those described in Example 1 except 10% (v/v) V8 medium was used.
Results Defensin enhanced the activity of the prothioconazole and fluquinconazole fungicides in a synergistic manner when assessed in in vitro assays with *L. maculans* (FIG. 6A prothioconazole, FIG. 6B fluquinconazole).

Results are also set forth in FIG. 6C wherein Ee is the expected effect from the additive response according to Limpel's formula (Richer (1987)) expressed as percent inhibition and Io is the percent inhibition observed.

Example 7

Inhibition of *Leptosphaeria maculans* Infection in Transgenic Canola Seedlings Expressing NaD1. Effect of Seed Coating with Chemical Fungicides
Production of Transgenic Canola Transgenic canola expressing NaD1 was produced from canola (*Brassica napus*) line RI64 by *Agrobacterium tumefaciens* mediated transformation. The DNA construct (pHEX3) used for the transformation is described in U.S. Pat. No. 7,041,877, incorporated herein by reference. The binary vector pHEX3 was transferred into *Agrobacterium tumefaciens* strain AGL 1 by electroporation and the presence of the plasmid confirmed by gel electrophoresis. Cultures of *Agrobacterium* were used to infect hypocotyl sections of canola cv RI64. Transgenic shoots were selected on the antibiotic kanamycin at 25 mg/L. Transgenic plants expressing NaD1 were selected by ELISA using an NaD1 specific antibody.
Method Used for ELISA Assay to Detect NaD1

ELISA plates (Nunc Maxisorp™ (In Vitro, Noble Park VIC 3174) #442404) were coated with 100 μL/well of primary antibody in PBS (50 ng/well protein A purified polyclonal rabbit antibody raised in response to the mature NaD1 domain (SEQ ID NO: 1, residues 26-72, RECK-TESNTFPGICITKPPCRKACISEKFTDGHCSKILR-RCLCTKPC, U.S. patent application Ser. No. 12/105,956) by a standard method) and incubated overnight at 4° C. in a humid box.

The next day, the plates were washed with PBS/0.05% (v/v) Tween® 20 for 2 min×4. Plates were then blocked with 200 μL/well 3% (w/v) BSA (Sigma (Castle Hill, NSW Australia 1765) A-7030: 98% ELISA grade) in PBS and incubated for 2 h at 25° C. and then washed with PBS/0.05% (v/v) Tween® 20, 2 min×4.

For preparation of leaf samples, 100 mg of frozen canola leaf tissue was ground in liquid nitrogen using a mixer mill for 2×10 sec at frequency 30. One mL of 2% (w/v) insoluble PVP (Polyclar)/PBS/0.05% (v/v) Tween® 20 was added to each sample and the mixture vortexed, centrifuged for 10 min and the supernatant collected. Dilutions of the canola protein extracts were prepared in PBS/0.05% (v/v) Tween® 20, applied to each well (100 μL/well) and incubated for 2 h at 25° C.

Plates were washed with PBS/0.05% (v/v) Tween® 20, 2 min×4. Secondary antibody in PBS (50 ng/well biotin-labelled anti-NaD1, raised to mature defensin domain) was applied to each well at 100 μL/well and incubated for 1 h at 25° C.

Plates were washed with PBS/0.05% (v/v) Tween® 20, 2 min×4. NeutriAvidin HRP-conjugate (Pierce, Rockford, Ill. 61105) #31001; 1:1000 dilution; 0.1 μL/well) in PBS was applied to each well at 100 μL/well and incubated for 1 h at 25° C.

Plates were washed with PBS/0.05% Tween® 20, 2 min×4 then with $H_2O$, 2 min×2. Fresh substrate was prepared by dissolving one ImmunoPure OPD (peroxidase substrate) tablet (Pierce, Rockford, Ill. 61105 #34006) in 9 mL water, then adding 1 mL stable peroxide buffer (10×, Pierce, Rockford, Ill. 61105 #34062). Substrate (100 μL/well) was added to each well and incubated at 25° C. The reaction was stopped with 50 μL of 2.5 M sulfuric acid and the absorbance measured at 490 nm in a plate reader.
Fungal Glasshouse Bioassay The pathogen *Leptosphaeria maculans* (Australian isolate ICBN18) was grown on 10% (v/v) V8 agar plates for 1-2 weeks at room temperature. Pycnidiospores were isolated by covering the plate with sterilized water (5 mL) and scraping the surface of the agar to dislodge the spores. Spores were separated from the hyphal matter by filtration through sterile tissues (eg Kleenex). The concentration of the spores in the filtrate was measured using a haemocytometer and the final concentration was adjusted to $10^6$ pycnidiospores/mL with water.

Seedlings (30 seeds per test) were grown in the glasshouse in small planting trays at 22° C. Ten days after sowing, the two cotyledons of each seedling were punctured twice with a 26 gauge needle (once in each of the 2 lobes) and the wounded area was inoculated with a droplet of spores (5 μL, $10^6$ spores/mL). Controls were inoculated with water. The plants were maintained under high humidity conditions for 3 days to facilitate spore germination.

Disease symptoms were assessed at 10, 14 and 17 days after inoculation. The diameter of each lesion was measured and the disease scored based on a system described by Williams and Delwiche (1979). Wounds with no darkening were scored as 0, lesions of diameter 0.5-1.5 mm were scored as 1, lesions of diameter 1.5-3.0 mm were scored as 3, lesions of diameter 3.0-6.0 were scored as 5, lesions greater than 6 mm in diameter or which had complete cotyledon necrosis were scored as 7. The disease scores were statistically analyzed by ordinal regression. Lesion size was quantified using computer software analysis (ImageJ) of digital images in $mm^2$. The average lesion size data was statistically analyzed by transforming the data (log 10) and performing the t-test.

To test for synergy between chemical fungicides and defensin expressed in transgenic canola plants seeds from the non-transgenic line RI64 and the NaD1 transformant CAT13.26 are either non-coated or are coated with the fungicides such as Jockey® (Registered Trademark) (active ingredient fluquinconazole, Bayer Crop Science) or fluoxastrobin (Bayer Crop Science). The seeds are coated with solutions containing the fungicide and air dried. The seeds are then germinated and infected with *L. maculans* as described above. Alternatively, 48 hours prior to inoculation with the pathogen, various concentrations of fungicide are applied to the surface of the cotyledons. Controls are treated with water. Disease symptoms are assessed as described above.

Results

Figure 7A:
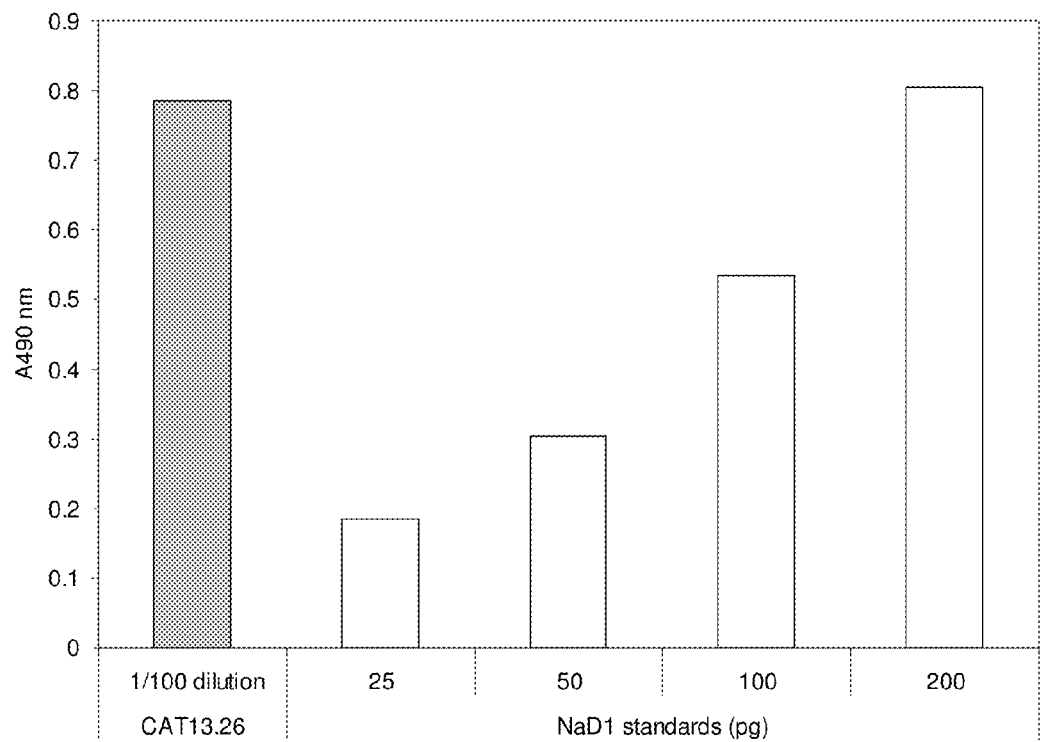

Several transgenic canola lines were produced and assessed for NaD1 expression by ELISA. Line CAT13.26 had detectable levels of protein expression (FIG. 7A) and was used for subsequent bioassays.

Figure 7B:
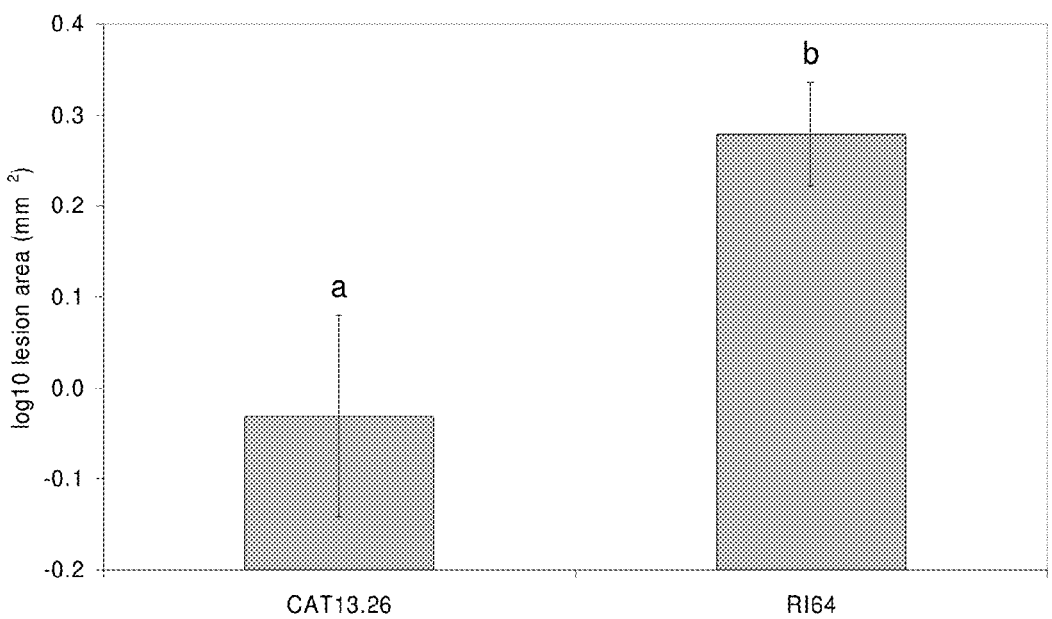
Figure 7C:
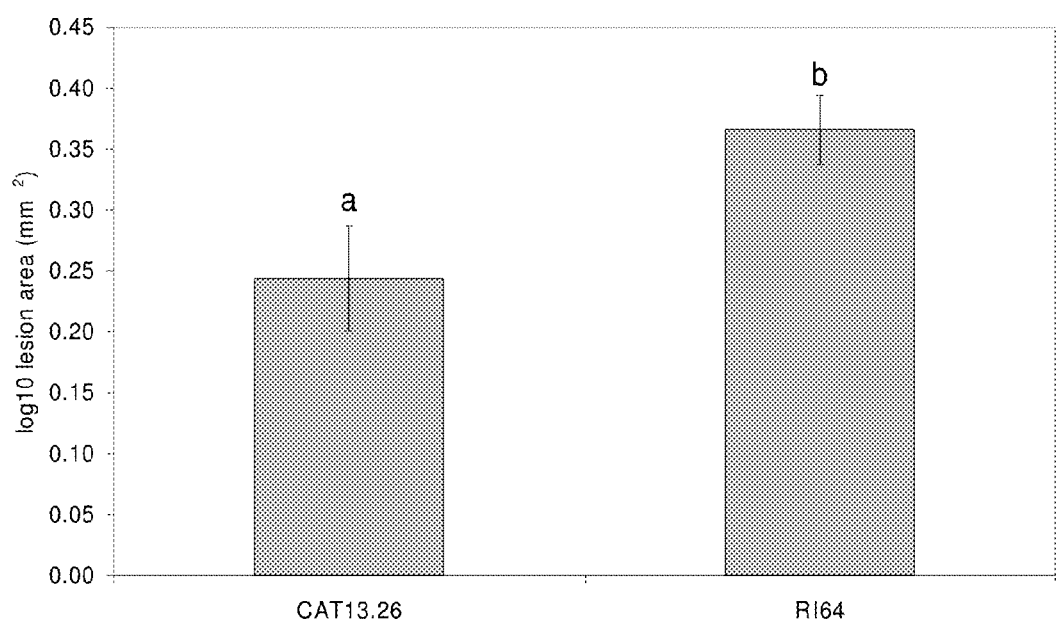

Non-transgenic RI64 plants and transgenic CAT13.26 plants expressing NaD1 were compared for their susceptibility to *L. maculans* infection in the glasshouse. Disease symptoms were assessed as described above. The CAT13.26 seedlings had significantly lower disease scores than the RI64 line at Days 10, 14 and 17 (P-values 0.010, 0.011 and 0.005, respectively). The average lesion size of the CAT13.26 seedlings expressing NaD1 was also significantly smaller than those on the non-transgenic plants at 10, 14 and 17 days after inoculation (P-values <0.001, 0.001 and <0.001, respectively). The results for days 10 and 17 are presented in FIGS. 7B and 7C.

Example 8

Inhibition of the Growth of *Fusarium graminearum* in the Presence of Other Defensins and Chemical Fungicides In Vitro Defensins were isolated from seeds or flowers using the procedure outlined in the detailed descriptions for purification of NaD1 from *Nicotiana alata* flowers. Briefly, seeds (500 g) were placed in an Ultra-Turrax homogenizer (Janke and Kunkel) and ground to a fine powder before addition of 50 mM sulfuric acid (4 mL per g fresh weight). Flowers were ground to a fine powder in liquid nitrogen before the addition of 50 mM sulphuric acid (3 mL per g fresh weight). Homogenisation was continued for 5 min before the homogenate was transferred to a beaker and stirred for 1 h at 4° C. Cellular debris was removed by filtration through Miracloth (Calbiochem, San Diego, Calif.) and centrifugation (25,000×g, 15 min, 4° C.). The pH was then adjusted to 7.0 by addition of 10 M NaOH and the extract was stirred for 1 h at 4° C. before centrifugation (25,000×g, 15 min, 4° C.) to remove precipitated proteins. The supernatant was applied to an SP-Sepharose™ Fast Flow (GE Healthcare Bio-Sciences) column (2.5×2.5 cm) pre-equilibrated with 10 mM sodium phosphate buffer. Unbound proteins were removed by washing with 20 column volumes of 10 mM sodium phosphate buffer (pH 6.0) and bound proteins were eluted in 3×10 mL fractions with 10 mM sodium phosphate buffer (pH 6.0) containing 500 mM NaCl.

Fractions from the SP Sepharose column were subjected to reverse-phase high performance liquid chromatography (RP-HPLC) using either an analytical Zorbax 300SB-C8 RP-HPLC column and an Agilent Technologies 1200 series system or a preparative Vydac C8 RP-HPLC column on a Beckman Coulter System Gold HPLC. Protein samples were loaded in buffer A (0.1% (v/v) trifluoroacetic acid) and eluted with a linear gradient of 0-100% (v/v) buffer B (60% (v/v) acetonitrile in 0.089% (v/v) trifluoroacetic acid. Eluted proteins were detected by monitoring absorbance at 215 nm. Protein peaks were collected and defensins were identified using SDS-PAGE and mass spectrometry.

The inhibitory effects of the plant defensins and chemical fungicides on the growth of *Fusarium graminearum* were measured as described for the NaD1 defensin in example 1.

Measurement of Relative Permeability Index of Various Plant Defensins on *F. graminearum* Hyphae.

i) SYTOX Green Uptake Assay

Hyphae (50 μL) that had been grown for 16 h in ½ PDB from a starting spore concentration of $5 \times 10^4$/mL were treated with 0.125, 0.25, 0.5, 1.25, 2.5, 5 or 10 μM NaD1 in the presence of 0.5 μM SYTOX green (Molecular Probes) in a final volume of 100 μL ½ PDB in black microtitre trays (Corning). SYTOX green fluorescence was monitored after 1 h using a fluorimeter (SpectraMax M5; Molecular Devices) with excitation and emission wavelengths of 485 nm and 538 nm respectively.

ii) ATP Release Assay

Permeabilization of hyphae was also measured by monitoring the release of ATP from the cells. Hyphae (40 μL) that had been grown for 16 h in ½ PDB from a starting spore concentration of $5 \times 10^4$/mL were treated with 0.125, 0.25, 0.5, 1.25, 2.5, 5 or 10 μM NaD1 in the presence of luciferase reagent (50 μL; Roche). The luciferase (from *Photinus pyralis*) catalyses the conversion of luciferin to oxyluciferin in the presence of ATP with a subsequent release of light. The light output is directly proportional to the ATP concentration. Luminescence was quantitated using a SpectraMax M5 spectrophotometer (Molecular Devices). A concentration dependant release of ATP was observed upon the addition of NaD1 to the hyphae indicating that the hyphal membrane had been compromised by the defensins and that ATP had been released into the medium.

Results

The SP-Sepharose bound proteins from the tomato and *N. alata* flower extracts were fractionated further by RP-HPLC and their elution profiles are shown in FIGS. 8A and 8B respectively. The proteins that were collected and used in the bioassays are labelled and their mass is provided in FIG. 8C.

The defensins that were isolated from the seeds or floral tissues of various plants are listed in FIG. 8C together with their mass.

FIG. 8D illustrates the relative amount of SYTOX green that enters *F. graminearum* hyphae in the presence of various concentrations of NaD1. SYTOX green uptake increases with increasing concentrations of NaD1. The effect of the defensins on membrane permeability was also assessed using an ATP-release assay. This assay confirmed that ATP release increased as the NaD1 concentration was raised from 0.125 to 10 μM NaD1 (FIG. 8E).

FIG. 8F illustrates the difference in permeabilization activity between the various plant defensins on *F. graminearum* hyphae growing in liquid culture as assessed by ATP release. The defensins with the highest permeabilization activity (NaD1, Tomdef2, Tomdef3 and NaD4), were all floral defensins from solanaceous plants. The amount of luminescence observed in the presence of 1 μM defensin correlated with the amount of growth inhibitory activity observed at the same defensin concentration.

Synergism between the various plant defensins and the triazole tebuconazole was most evident with the defensins that had the highest permeabilization and antifungal activity (FIG. 8F). FIGS. 8G-8L illustrate the growth curves obtained with various concentrations of the defensins NaD1 (FIG. 8G), Tomdef3 (FIG. 8H), NaD4 (FIG. 8I), Tomdef2 (FIG. 8J), NaD2 (FIG. 8K) and SFSH4 (FIG. 8L) with tebuconazole.

Synergy calculations from the data presented on FIGS. 8G-8L are set forth in FIG. 8M wherein Ee is the expected effect from the additive response according to Limpels's formula (Richer, 1987) expressed as percent inhibition and Io is the percent inhibition observed. Synergy, that is, Io values higher that Ee values was obtained with the triazole tebuconazole and the floral defensins NaD1, NaD4 and tomdef3.

The relationship between the relative permeability index of each of the defensins on *F. graminearum* and their antifungal activity is tabulated in FIG. 8N. Permeability index (PI) was defined as the relative amount of luminescence units obtained in 10 min with 1 µM defensin compared to the luminescence obtained with 1 µM NaD1 which was given a PI of 1.

Example 9

Inhibition of the Growth of *Sclerotinia sclerotiorum* in the Presence of NaD1 and Chemical Fungicides In Vitro The inhibitory effects of defensin (NaD1) and chemical fungicides are assayed on growth of *Sclerotinia sclerotiorum* (Australian isolate UQ1280 from Prof. B. Howlett, School of Botany University of Melbourne, Victoria, Australia).

*Sclerotinia sclerotiorum* is grown for one week in PDB until the culture produces a large hyphal cluster and no asexual spores. A large piece of hyphal matter (about 5 cm$^2$) is excised and placed in 30 mL of ½ strength PDB. A suspension of hyphal fragments is prepared by homogenization with a Polytron (Ystral, Germany) (3×30 sec, speed 6). The homogenate is diluted with ½ strength PDB until it has an absorbance at 590 nm of 0.1. The conditions used for the fungal growth assay are the same as those described in Example 1 except that 90 µL of hyphal suspension is used to inoculate the wells of the microtitre plate instead of the spore suspension.

Example 10

Inhibition of *Sclerotinia sclerotiorum* Infection in Transgenic Canola Seedlings Expressing NaD1. Effect of Seed Coating with Chemical Fungicides Transgenic canola expressing NaD1 is produced by *Agrobacterium tumefaciens* mediated transformation as described in Example 7.

The pathogen *Sclerotinia sclerotiorum* is grown on 10% (v/v) V8 agar plates for 3-5 days at 25° C. Adult leaves from canola plants expressing NaD1 are removed and placed in petri dishes with moist filter paper. The leaves are inoculated by placing agar plugs from the growing front of the *S. sclerotiorum* culture face down onto the leaf surface (4 agar plugs per leaf). The inoculated leaves are incubated at 25° C. and the height and diameter of the lesions are measured 24, 48 and 72 hours after placing the agar plugs on the leaves.

BIBLIOGRAPHY

Abad et al. *Plant Sci* 118:11-23, 1996
Alexander et al, *Proc Natl Acad Sci* 90:7327-7331, 1993
Ausubel et al, *Current Protocols in Molecular Biology*, Wiley Interscience, New York, N.Y., 1993
Beck et al, *Bio/Technology.* 11:1524, 1993
Bartlett et al, *Pest Manag Sci* 58:649-662), 2002
Bevan et al, *Nucl Acids Res* 11(2):369-385, 1993
Broekaert et al, *FEMS Microbiol Lett* 69:55-59, 1990
Davey et al, *Plant Mol Biol* 13:275, 1989
De Samblanx et al, *J Biol Chem* 272:1171-1179, 1997
de Vos et al, *Proc Natl Acad Sci USA* 82:1406-1409, 1985
Ekengren et al, *Insect Biochem Mol Biol* 29:965-972, 1999
Epand et al, *Biochim Biophys Acta* 1758:1343-1350, 2006
Gasser and Fraley, *Science* 244:1293, 1989
Goding, *Monoclonal Antibodies*: Principles and Practice, 2d ed., Academic Press, New York, 1986
Gorlach et al, *Plant Cell* 8:629-643, 1996
Graham et al, *Plant Physiol* 135:1179-1197, 2004
Greco et al, *Pharmacol Rev.* 47:331-385, 1995
Harlow and Lane, *Antibodies*: A Laboratory Manual, Cold Spring Harbor Laboratories, 1988
Herrera-Estrella et al, *EMBO J.* 2:987-995, 1983
Joersbo and Burnstedt, *Physiol. Plant.* 81:256, 1991
Kim et al, *Eur J Biochem* 268:4449-4458, 2001
Klee et al, *Bio/Technology.* 3:637-642, 1985
Klis et al, *FEMS Microbiol Rev* 26:239-256, 2002
Koziel et al, *Bio/Technology.* 11:194, 1993
Ladokhin and White, *Biochim Biophy Acta* 1514:253-260, 2001
Ladokhin et al, *Biophysical Journal* 72:1762-1766, 1997
Lay, Structure and function of floral defensins from *Nicotiana alata* and *Petunia hybrida*. (PhD thesis). In Department of Biochemistry (La Trobe University), 2003
Lay and Anderson, *Curr Protein Peptide Sci* 6:80-101, 2005
Lay et al, *Plant Physiol* 131:1283-1293, 2003
Leemans, *Bio/Technology.* 11:522, 1993
Leiter et al, *Antimicrob Agents Chemother* 49:2445-2453, 2005
Lobo et al, *Biochemistry* 46: 987-996, 2007
Matsuzaki, *Biochim Biophys Acta* 1462:1-10, 1999
Matsuzaki et al, *Biochemistry* 34:3423-3429, 1995
Nilsson et al, *Cell* 58:707, 1989
Oberparleiter et al, *Antimicrob Agents Chemother* 47:3598-3601, 2003
Oerke and Dehne, *Crop Protection* 23:275-285, 2003
Potrykus, *Annu. Rev. Plant Physiol. Plant Mol Biol* 42:205, 1991
Poirot et al, *Nucl Acids Res* 31:3503-3506, 2003
Potter et al, *Mol Plant Microbe Interact* 6:680-685, 1993
Ramamoorthy et al, *Molecular Microbiology* 66:771-786, 2007
Richer, *Pestic. Sci.* 19:309-315, 1987
Rogers et al, *Methods for Plant Molecular Biology*, 1998
Sambrook et al, *Molecular Cloning*, Second Edition, Cold Spring Harbor Laboratory, Plainview, N.Y., 1989
Salzman et al, *Mol Plant Microbe Interact* 17:780-788, 2004
Schilperoort et al, EPO publication 120, 516
Silverstein et al, *Plant Physiol* 138, 600-610, 2005
Tamura et al, *Molec Biol Evol* 24:1596-1599, 2007
Theis et al, *Antimicrob Agents Chemother* 47:588-593, 2003
Theis and Stahl, *Cell Mol Life Sci* 61: 437-455, 2004
Thevissen et al, *Mol Plant Microbe Interact* 13:54-61, 2000a
Thevissen et al, *Proc Natl Acad Sci USA* 97:9531-9536, 2000b
Thevissen et al, *J Biol Chem* 279:3900-3905, 2004
Thevissen et al, *Curr Drug Targets* 6:923-928, 2005
Vasil et al, *Bio/Technology.* 11:1533, 1993
Walden and Schjell, *Eur J Biochem* 192:563, 1990
Williams and Delwiche, In: *Proceedings of Eucarpia Cruciferae Conference*, 1979, Wageningen, The Netherlands, 164-70, 1979

The invention claimed is:

1. A method for protecting a plant or plant seed from a disease caused by a given susceptible fungus, comprising applying said plant, plant seed or a soil surrounding the plant seed with a floral defensin which exhibits a relative permeability index of greater than 0.4 in contact with the given susceptible fungus on a scale where the permeability index of defensin NaD1 is set as 1.0 and a chemical fungicide, wherein the defensin and the chemical fungicide in combination being synergistic with respect to inhibition of the fungus, wherein the chemical fungicide is a strobilurin and/or a triazole.

2. The method of claim 1, wherein the defensin is a defensin of a solanaceous plant.

3. The method of claim 1, wherein the contacting of the plant is to a leaf or stem of the plant.

4. The method of claim 1, wherein the contacting of the plant seed is by topically coating the seed.

5. The method of claim 1, wherein the defensin is NaD1.

6. The method of claim 1, wherein the chemical fungicide is a strobilurin fungicide selected from the group consisting of azoxystrobin, picoxystrobin and fluoxastrobin.

7. The method of claim 1, wherein the chemical fungicide is a triazole fungicide selected from the group consisting of propiconazole, tebuconazole, flusilazole, fluquinconazole and prothioconazole.

8. The method of claim 1, wherein the susceptible fungus is a filamentous fungus.

9. The method of claim 8, wherein the filamentous fungus is selected from the group consisting of *Fusarium, Sclerotinia, Leptosphaeria* and *Verticillium*.

10. The method of claim 1, wherein the plant seed is from a plant genetically modified to express a plant defensin.

11. The method of claim 1, wherein the defensin is a recombinant defensin.

12. The method of claim 1, wherein the permeability index is measured using a green fluorescent nucleic acid-binding dye or propidium iodide.

13. The method of claim 1, wherein the permeability index is measured using an ATP release assay wherein the ATP release assay measures conversion of luciferin to oxyluciferin by luciferase in the presence of ATP released by the fungus with concomitant release of light.

14. The method of claim 1, wherein the defensin and the fungicide are provided in the form of a spray.

15. The method of claim 1, wherein the defensin and the fungicide are admixed prior to application to the plant or seed or surrounding soil.

16. A composition having antifungal properties, for contacting a plants a plant seed or a soil surrounding the plant seed, comprising a floral defensin and a chemical fungicide, wherein said defensin exhibits a relative permeability index of greater than 0.4 in contact with a given susceptible fungus on a scale where the permeability index of defensin NaD1 is set as 1.0, wherein the chemical fungicide is a strobilurin and/or a triazole, and wherein the defensin and the chemical fungicide in combination being synergistic with respect to inhibition of the fungus.

17. The composition of claim 16 in the form of a spray or a formulation for delivery to soil.

18. The composition of claim 16 in the form of a coating for a plant seed.

19. A kit comprising a floral defensin and a chemical fungicide wherein said defensin exhibits a relative permeability index of greater than 0.4 in contact with a given susceptible fungus on a scale where the permeability index of defensin NaD1 is set as 1.0, wherein the defensin and the chemical fungicide are admixed prior to application to a plant or plant seed, wherein the chemical fungicide is a strobilurin and/or a triazole, and wherein the defensin and the chemical fungicide in combination being synergistic with respect to inhibition of the fungus.

* * * * *